US011952431B2

(12) United States Patent
Granot et al.

(10) Patent No.: US 11,952,431 B2
(45) Date of Patent: Apr. 9, 2024

(54) NEUTROPHIL-BINDING PEPTIDES

(71) Applicants: YISSUM RESEARCH DEVELOPMENT COMPANY OF THE HEBREW UNIVERSITY OF JERUSALEM LTD., Jerusalem (IL); HADASIT MEDICAL RESEARCH SERVICES & DEVELOPMENT LTD., Jerusalem (IL)

(72) Inventors: Zvika Granot, Jerusalem (IL); Zvi Gregorio Fridlender, Zur-Hadassah, IL (US); Sandra Vols, Moshav Mata (IL)

(73) Assignees: YISSUM RESEARCH DEVELOPMENT COMPANY OF THE HEBREW UNIVERSITY OF JERUSALEM LTD., Jerusalem (IL); HADASIT MEIDCAL RESEARCH SERVICES & DEVELOPMENT LTD., Jerusalem (IL)

( * ) Notice: Subject to any disclaimer, the term of this patent is extended or adjusted under 35 U.S.C. 154(b) by 0 days.

(21) Appl. No.: 18/089,067

(22) Filed: Dec. 27, 2022

(65) Prior Publication Data

US 2023/0203203 A1 Jun. 29, 2023

Related U.S. Application Data

(63) Continuation of application No. PCT/IL2021/050783, filed on Jun. 27, 2021.

(60) Provisional application No. 63/045,107, filed on Jun. 28, 2020.

(51) Int. Cl.
| | |
|---|---|
| A61K 9/14 | (2006.01) |
| A61K 31/03 | (2006.01) |
| A61K 31/4196 | (2006.01) |
| A61K 31/4439 | (2006.01) |
| A61K 47/64 | (2017.01) |
| A61K 47/69 | (2017.01) |
| A61P 11/00 | (2006.01) |
| B82Y 5/00 | (2011.01) |
| B82Y 30/00 | (2011.01) |
| C07K 5/12 | (2006.01) |
| C07K 7/06 | (2006.01) |
| C07K 7/08 | (2006.01) |
| C07K 14/00 | (2006.01) |
| C07K 17/08 | (2006.01) |
| C12N 5/16 | (2006.01) |

(52) U.S. Cl.
CPC ............ *C07K 17/08* (2013.01); *A61K 31/03* (2013.01); *A61K 31/4196* (2013.01); *A61K 31/4439* (2013.01); *A61K 47/6937* (2017.08); *C07K 7/06* (2013.01); *C07K 7/08* (2013.01); *B82Y 5/00* (2013.01); *B82Y 30/00* (2013.01)

(58) Field of Classification Search
None
See application file for complete search history.

(56) References Cited

U.S. PATENT DOCUMENTS 9,603,948 B2 * 3/2017 Santamaria ........ A61K 47/6923

OTHER PUBLICATIONS

Hendrick and Malachi (Nature Rev. Immunol. 2022, 22: 173-187) (Year: 2022).*
Bershtyn et al (J. Contr. Rel. 2012, 157: 354-365) (Year: 2012).*
Lee and Roller (Cur. Topics in Med. Chem., 2002, 2: 325-341) (Year: 2002).*
Neuner P, Gallo P, Orsatti L, Fontana L, Monaci P. An efficient and versatile synthesis of bisPNA-peptide conjugates based on chemoselective oxime formation. Bioconjug Chem. Mar.-Apr. 2003;14(2):276-81. doi: 10.1021/bc020060p. PMID: 12643736.
Scientific Program. The Joint Meeting of the Israeli Immunological Society (IIS) and the Israeli Society for Cancer Research (ISCR). Sep. 23-25, 2019. Tel Aviv, Israel, pp. 1-289.
Daley JM, Thomay AA, Connolly MD, Reichner JS, Albina JE. Use of Ly6G-specific monoclonal antibody to deplete neutrophils in mice. J Leukoc Biol. Jan. 2008;83(1):64-70. doi: 10.1189/jlb.0407247. Epub Sep. 20, 2007. PMID: 17884993.
Mazzucchelli L, Burritt JB, Jesaitis AJ, Nusrat A, Liang TW, Gewirtz AT, Schnell FJ, Parkos CA. Cell-specific peptide binding by human neutrophils. Blood. Mar. 1, 1999;93(5):1738-48. PMID: 10029604.
Fridlender ZG, Sun J, Kim S, Kapoor V, Cheng G, Ling L, Worthen GS, Albelda SM. Polarization of tumor-associated neutrophil phenotype by TGF-beta: "N1" versus "N2" TAN. Cancer Cell. Sep. 8, 2009;16(3):183-94. doi: 10.1016/j.ccr.2009.06.017. PMID: 19732719; PMCID: PMC2754404.
Laping NJ, Grygielko E, Mathur A, Butter S, Bomberger J, Tweed C, Martin W, Fornwald J, Lehr R, Harling J, Gaster L, Callahan JF, Olson BA. Inhibition of transforming growth factor (TGF)-beta1-induced extracellular matrix with a novel inhibitor of the TGF-beta type I receptor kinase activity: SB-431542. Mol Pharmacol. Jul. 2002;62(1):58-64. doi: 10.1124/mol.62.1.58. PMID: 12065755.

(Continued)

*Primary Examiner* — Michael Szperka
*Assistant Examiner* — Marianne Dibrino
(74) *Attorney, Agent, or Firm* — The Roy Gross Law Firm, LLC; Roy Gross

(57) ABSTRACT

Disclosed are peptides that specifically bind to neutrophils and uses thereof for neutrophil-targeted delivery of drugs or diagnostic agents in medical conditions including cancer as well as infectious, inflammatory and autoimmune diseases or disorders.

20 Claims, 49 Drawing Sheets
(19 of 49 Drawing Sheet(s) Filed in Color)
Specification includes a Sequence Listing.

(56) References Cited

OTHER PUBLICATIONS

Li S, McGuire MJ, Lin M, Liu YH, Oyama T, Sun X, Brown KC. Synthesis and characterization of a high-affinity {alpha} v{beta}6-specific ligand for in vitro and in vivo applications. Mol Cancer Ther. May 2009;8(5):1239-49. doi: 10.1158/1535-7163.MCT-08-1098. Epub May 12, 2009. PMID: 19435868; PMCID: PMC4053473.
Johnson JL, Ramadass M, He J, Brown SJ, Zhang J, Abgaryan L, Biris N, Gavathiotis E, Rosen H, Catz SD. Identification of Neutrophil Exocytosis Inhibitors (Nexinhibs), Small Molecule Inhibitors of Neutrophil Exocytosis and Inflammation: Druggability of the Small GTPase Rab27a. J Biol Chem. Dec. 9, 2016;291(50):25965-25982. doi: 10.1074/jbc.M116.741884. Epub Oct. 4, 2016. PMID: 27702998; PMCID: PMC5207069.
Bai M, Grieshaber-Bouyer R, Wang J, Schmider AB, Wilson ZS, Zeng L, Halyabar O, Godin MD, Nguyen HN, evescot A, Cunin P, Lefort CT, Soberman RJ, Nigrovic PA. CD177 modulates human neutrophil migration through activation-mediated integrin and chemoreceptor regulation. Blood. Nov. 9, 2017;130(19):2092-2100. doi: 10.1182/blood-2017-03-768507. Epub Aug. 14, 2017. PMID: 28807980; PMCID: PMC5680608.

PCT International Search Report for International Application No. PCT/IL2021/050783, dated Oct. 13, 2021, 4pp.
PCT Written Opinion for International Application No. PCT/IL2021/050783, dated Oct. 13, 2021, 6pp.
PCT International Preliminary Report on Patentability for International Application No. PCT/IL2021/050783, dated Dec. 13, 2022, 7pp.
Simon Tazzyman et al. "Neutrophils: key mediators or tumour angiogenesis." International Journal of Experimental Pathology 2009, vol. 90, Issue 3, pp. 222-231.
Miettinen HM, Gripentrog JM, Lord CI, Nagy JO. CD177-mediated nanoparticle targeting of human and mouse neutrophils. PLOS One. Jul. 10, 2018; 13(7):e0200444, pp. 1-23. doi: 10.1371/journal.pone.0200444. PMID: 29990379; PMCID: PMC6039027.
Ryvkin A, Ashkenazy H, Weiss-Ottolenghi Y, Piller C, Pupko T, Gershoni JM. Phage display peptide libraries: deviations from randomness and correctives. Nucleic Acids Res. May 18, 2018;46(9):e52, pp. 1-10. doi: 10.1093/nar/gky077. PMID: 29420788; PMCID: PMC5961013.
Granot Z. Neutrophils as a Therapeutic Target in Cancer. Front Immunol. Jul. 19, 2019;10:1710, pp. 1-6. doi:10.3389/fimmu.2019.01710. PMID: 31379884; PMCID: PMC6659000.

* cited by examiner

Doa = 8-Amino-3,6-dioxaoctanoic acid (increases solubility) MW: 7600 kDa
Mpa = 3-Maleimidopropionic acid (linker)

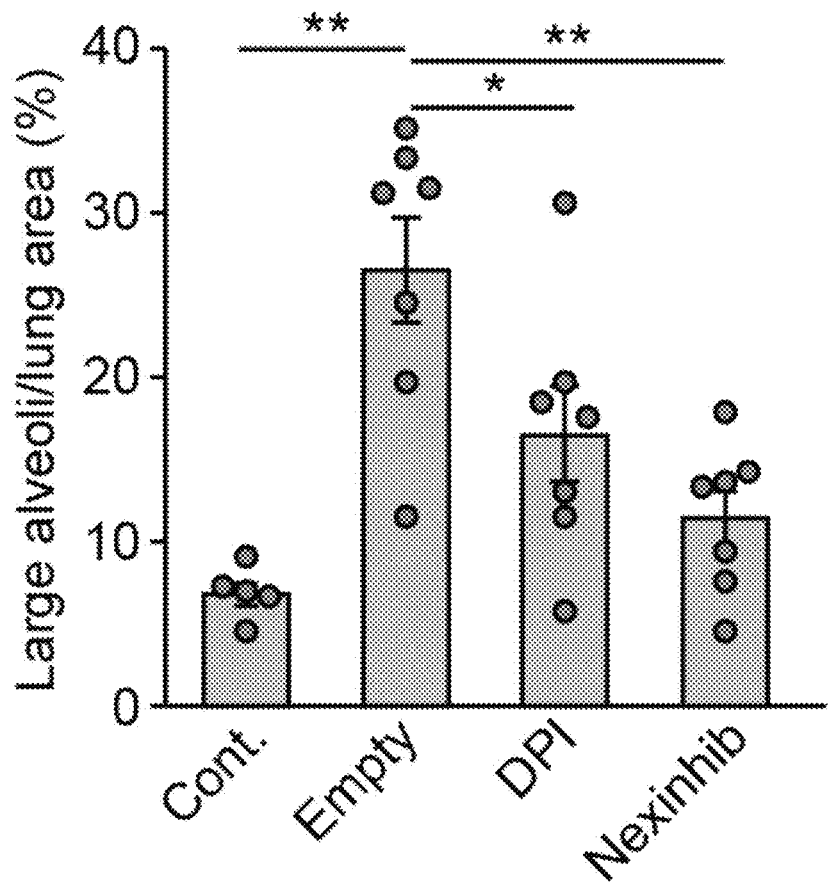

| Rank | Description | ΣCoverage |
|---|---|---|
| 1 | CD177 | 21.91 |
| 2 | Myoblastin | 15.08 |
| 3 | Hspa8 | 18.11 |
| 4 | Glipr2 | 22.08 |
| 5 | MCG1050941 | 11.05 |

NEUTROPHIL-BINDING PEPTIDES

CROSS REFERENCE TO RELATED APPLICATIONS

This application claims the benefit of priority of U.S. Provisional Patent Application No. 63/045,107, Jun. 28, 2020, the content of which is incorporated herein by reference in its entirety.

REFERENCE TO AN ELECTRONIC SEQUENCE LISTING

The contents of the electronic sequence listing (IMUX-P-001-US_SQL.xml; Size: 23,082 bytes; and Date of Creation: Dec. 27, 2022) is herein incorporated by reference in its entirety.

FIELD OF THE INVENTION

The present invention relates to neutrophil-targeted delivery of therapeutic or diagnostic agents in medical conditions including cancer as well as infectious, inflammatory and autoimmune diseases or disorders.

BACKGROUND OF THE INVENTION

Malignant cells are basically recognizable to the immune system. However, tumors have evolved mechanisms to create a complex immunosuppressive network that paralyzes the effector arm of the immune response. Tumor immunosuppression is directed by inhibitory cytokines and more importantly, specific cellular populations. Key parts of this immunosuppressive network are myeloid cells, in particular neutrophils and macrophages, "re-educated" by the tumor microenvironment to support tumor growth.

The role of neutrophil in cancer has been studied much less extensively than other cells of the immune system, such as T-cells and macrophages. Yet, there is increasing evidence suggesting that neutrophils contribute to tumorigenesis by supporting angiogenesis and tumor cell growth. On the other hand, along with having pro-tumor functionality, neutrophils have also been shown to have anti-tumor properties and ability to kill tumor cells directly, for example by release of reactive oxygen species, proteases, membrane-perforating agents, or cytokines such as TNFα and interleukin-1β (Tazzyman S, et al. International journal of experimental pathology, 2009, 90(3), 222-231).

In addition to their anti-cancer potential, neutrophils are potent effector cells in a wide range of infectious, inflammatory and autoimmune conditions. Modulation of neutrophil functions in patients afflicted with these conditions as well as in cancer patients may have significant therapeutic benefits and effects on disease progression. However, the remarkably short lifetime of neutrophils poses a major challenge for ex vivo manipulation and subsequent transplantation of these cells.

In vivo manipulation of neutrophil function requires targeting of an active agent specifically to the neutrophil population in order to minimize off-target effects. Antibodies specific to mouse neutrophils are available (Daley, J Leukoc Biol. 2008, 83(1), 64-70), but they deplete neutrophils when administered in vivo.

Mazzucchelli L et al. (Blood, 1999, 93(5), 1738-1748) disclose peptides specifically binding to human neutrophils and monocytes. The peptide sequences were identified using phage display libraries.

CD177 is a neutrophil-specific extracellular surface protein that belongs to a gene superfamily which as common feature possesses at least one LU domain (Ly/uPAR) having 80 amino-acids including 10 cysteines. Human CD177 is 50% conserved when aligned to C-terminus of mouse CD177. The human CD177 contains 2 direct repeats of the LU domain, while the mouse CD177 has 4. Miettinen et al. 2018 (PLoS ONE 13(7): e0200444) discloses CD177-mediated nanoparticle targeting of human and mouse neutrophils by binding peptides identified from a phage display library.

There remains an unmet need for a safe, versatile and non-expensive platform for highly specific antibody-independent neutrophil targeting for therapeutic and diagnostic applications.

SUMMARY OF THE INVENTION

The present invention provides novel peptide sequences that specifically bind to neutrophils, peptide conjugates and multimeric molecules comprising said peptide sequences. The peptides, peptide conjugates and their multimeric forms can be used as targeting agents for specific in vivo delivery of therapeutic and/or diagnostic agents to neutrophils and are useful in particular in patients afflicted with cancer, infectious diseases, inflammatory diseases or disorders or inflammatory autoimmune diseases or disorders.

According to a first aspect, there is provided a peptide comprising an amino acid sequence selected from the group consisting of:

KFPDLDSRRLPHMSL; (SEQ ID NO: 1)

LATTHMVFSPDH; (SEQ ID NO: 2)

PSSNLESTPLSLL; (SEQ ID NO: 3)

SSLMTTQLIATSI; (SEQ ID NO: 4)

PELDSKPYFPPL; (SEQ ID NO: 5)

ELVTASMPRPNN; (SEQ ID NO: 6)

SLESSPMAQLPQ; (SEQ ID NO: 7)

SELRSTPLLVPS; (SEQ ID NO: 8)

LQIQSWSSSP; (SEQ ID NO: 9)

STMTILGTGS; (SEQ ID NO: 10)

TETSLRIVSTNP; (SEQ ID NO: 11)

LSIVSGSALNHL; (SEQ ID NO: 12)
and

LTLVSERPMI. (SEQ ID NO: 13)

According to some embodiments, the peptide comprises 6-30 amino acids.

According to some embodiments, the peptide comprises 10-20 amino acids.

According to some embodiments, the peptide consists of an amino acid sequence selected from the group consisting of: SEQ ID NO: 1-13.

According to some embodiments, the peptide comprises at least one cyclization.

According to some embodiments, the peptide comprises an amino acid sequence selected from the group consisting of: SEQ ID NO: 1-8.

According to some embodiments, the peptide comprises an amino acid sequence selected from the group consisting of SEQ ID NO: 9-13.

According to some embodiments, the peptide is conjugated to at least one moiety capable of increasing solubility and optionally to at least one linker or spacer.

According to some embodiments, the at least one moiety capable of increasing solubility is an 8-amino-3,6-dioxaoctanoic acid (Doa) residue.

According to some embodiments, peptide has a structure according to Formula III:

Peptide-Doa-Doa-C          (Formula III)

wherein the C is a Cysteine residue, and the Peptide denotes a peptide of the invention.

According to some embodiments, the linker comprises a 3-maleimidopropionic acid (Mpa) residue.

According to another aspect, there is provided a peptide multimer comprising a plurality of identical or different peptides of the invention.

According to some embodiments, the peptide multimer comprises 2-20 identical or different peptides.

According to some embodiments, the peptide multimer comprises 2-4 identical or different peptides.

According to some embodiments, the peptide multimer comprises 4 identical or different peptides.

According to some embodiments, the peptides are covalently linked to each other or to a scaffold directly or through a linker or spacer.

According to some embodiments, the peptide multimer comprises a branched scaffold.

According to some embodiments, the branched scaffold comprises at least one Lys residue linked to the peptides directly or through a spacer or linker.

According to some embodiments, the peptide multimer further comprises a biotin moiety covalently attached to the peptide multimer.

According to some embodiments, the peptide multimer has a structure according to Formula I:

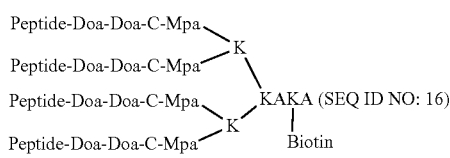

Formula I wherein each Peptide independently denotes a peptide of the invention.

According to some embodiments, the peptide multimer has a structure according to Formula II:

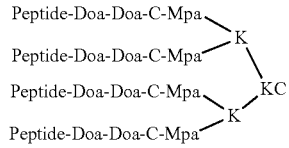

Formula II wherein each Peptide independently denotes a peptide of the invention.

According to some embodiments, the peptide multimer comprises at least two different peptides.

According to some embodiments, the peptide multimer comprises four identical peptides.

According to another aspect, there is provided a peptide complex comprising at least two peptide multimers of the invention.

According to some embodiments, the peptide of the invention, the peptide multimer of the invention, or the peptide complex of the invention, comprises an amino acid sequence selected from the group consisting of SEQ ID NO: 1 to 8, for use in targeting to human neutrophils.

According to some embodiments, the peptide of the invention, the peptide multimer of the invention, or the peptide complex of the invention, comprises an amino acid sequence selected from the group consisting of SEQ ID NO: 9 to 13, for use in targeting to murine neutrophils.

According to another aspect, there is provided a composition comprising a peptide of the invention, a peptide multimer of the invention, or a peptide complex of the invention attached to a therapeutic or diagnostic agent directly or through a carrier or linker.

According to another aspect, there is provided a composition comprising a nanoparticle comprising a core particle and a peptide of the invention, a peptide multimer of the invention, or a peptide complex of the invention attached to an outer surface of the core particle.

According to some embodiments, the composition further comprises a therapeutic or diagnostic agent.

According to some embodiments, the therapeutic agent is a neutrophil modifying therapeutic agent.

According to some embodiments, the neutrophil modifying therapeutic agent is a neutrophil cytotoxic agent.

According to some embodiments, the therapeutic agent is selected from the group consisting of a TGF-β inhibitor, an exocytosis inhibitor and a flavoenzyme inhibitor.

According to some embodiments, the TGF-β inhibitor is SB431542, the exocytosis inhibitor is Nexinhib-20 and the flavoenzyme inhibitor is diphenyleneiodonium chloride (DPI).

According to another aspect, there is provided a pharmaceutical composition comprising a peptide of the invention, a peptide multimer of the invention, a peptide complex of the invention or a composition of the invention and a pharmaceutically acceptable carrier, excipient or adjuvant.

According to some embodiments, the pharmaceutical composition is formulated for systemic administration or administration to a site of inflammation.

According to some embodiments, the pharmaceutical composition is for use in treating a neutrophil-associated disease or condition.

According to some embodiments, the pharmaceutical composition is for use in treating a disease or condition associated with accumulation of neutrophils to a diseased or injured tissue or site.

According to some embodiments, the disease or condition is selected from the group consisting of: a cancer, an inflammatory disease or condition and an inflammatory autoimmune disease or condition.

According to some embodiments, the disease or condition is an inflammatory disease or condition.

According to some embodiments, the inflammatory disease or condition is selected from chronic obstructive pulmonary disease (COPD), inflammatory bowel disease (IBD) and peritonitis.

According to another aspect, there is provided a method of treating a neutrophil-associated disease or condition in a subject in need thereof, the method comprising administering to the subject a pharmaceutical composition of the invention.

According to some embodiments, the disease or condition is selected from the group consisting of: a cancer, an inflammatory disease or condition and an inflammatory autoimmune disease or condition.

According to some embodiments, the disease or condition is an inflammatory disease or condition.

According to some embodiments, the inflammatory disease or condition is selected from chronic obstructive pulmonary disease (COPD), inflammatory bowel disease (IBD) and peritonitis.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIGS. 20A-K: Neutrophil Specific Targeting of Degranulation and ROS Production Attenuates the Development of COPD. (20A) Schematic of the experimental timeline. (20B-E) Combination plots showing quantification of (20B) total cells, (20C) Ly6G+neutrophils, (20D) CD3+T cells and (20E) F4/80 BALF of healthy PBS treated, COPD empty NP treated, COPD DPI-NP treated, and COPD Nexinhib-20-NP treated mice. (20F) Line graph of average pressure-volume loops of healthy PBS treated (blue), COPD empty NP treated (red), COPD DPI-NP treated (green) and COPD Nexinhib-20 NP treated mice (violet). (20G-H) Mixed plots of (20G) forced vital capacity (FVC) and (20H) forced expiration volume 0.05 (FEV0.05) to FVC ratio of healthy PBS treated, COPD empty NP treated, COPD DPI-NP treated and COPD Nexinhib-20-NP treated mice. (20I) Representative images showing large (emphysematous) alveoli in lungs from healthy mice (Healthy Control) and mice with COPD treated with empty NP (COPD Empty NP), DPI-containing NP (COPD DPI NP) or Nexinhib-20-containing NP (COPD Nexinhib-20 NP). (20J) Mixed plot of average frequency of large (emphysematous, highlighted in blue in 20I) alveoli per lung area in control mice (Cont.) or mice with COPD treated with empty NP (Empty), DPI-containing NP (DPI) or Nexinhib-20-containing NP. (20K) Representative H&E staining of whole lungs from healthy mice (Healthy Control) and mice with COPD treated with empty NP (COPD Empty NP), DPI-containing NPs (COPD DPI-NP) or Nexinhib-20-containing NPs (COPD Nexinhib-20-NPs).

DETAILED DESCRIPTION OF THE INVENTION

Figure 1A:
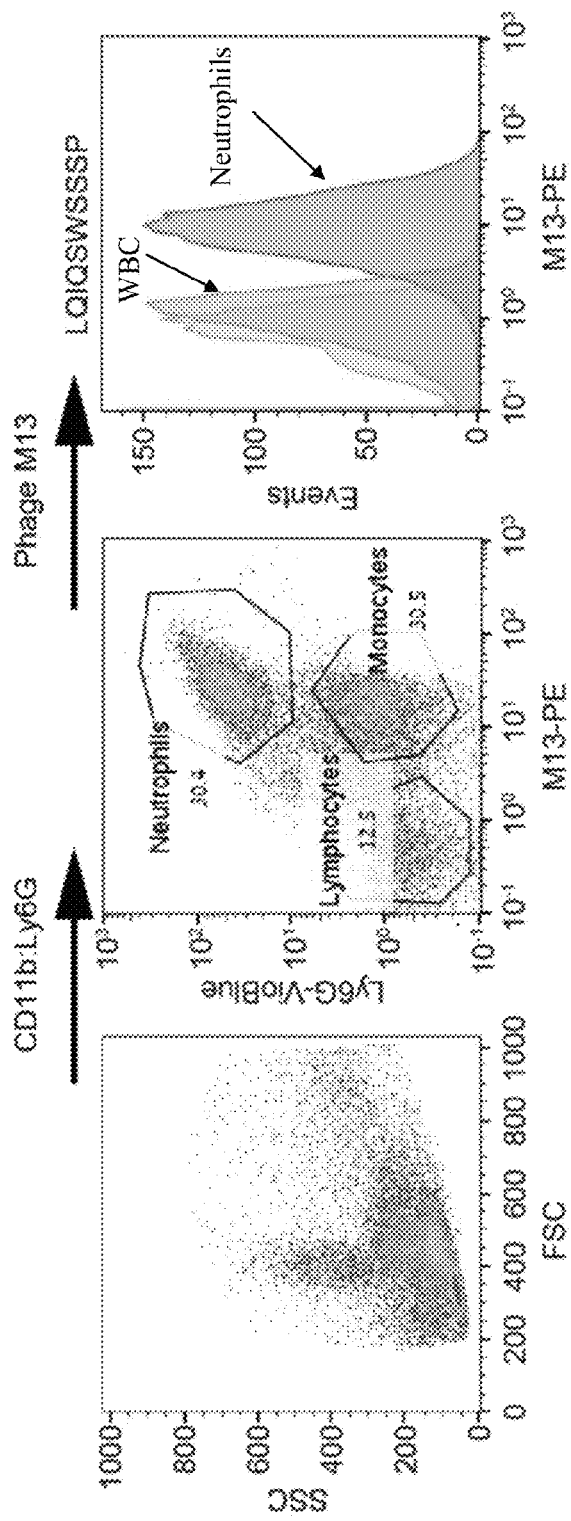
FIGS. 1A-D: Validation of Phage Binding of Highest-Ranking Peptides Sequences Selected on Mouse Neutrophils. (1A-B) WBC were isolated from 4T1 tumor bearing mice and binding of phage presenting the LQIQSWSSSP (SEQ ID NO: 9) peptide to neutrophils (Ly6G+CD11b+, red histogram) and other WBC (Ly6G−CD11b−, blue histogram) was evaluated using anti-M13 PE-labelled antibody and (1A) flow cytometry analysis or (1B) microscopy. (1C) Overview of LQI peptide constructs—the LQI peptide sequence on the phage is inserted within the protein VIII coat protein of the phage (LQI peptide in orange) and neighboring amino acid residues are depicted (recombinant LQI pVIII). An unlabeled, Cy5-labeled, biotin-labeled and the LQI peptide construct including neighboring amino acids from coat protein VIII as well as a glycine linker and fluorescein, were generated and tested for binding. (1D) Competition assay of LQI phage binding and LQI peptide constructs. Neutrophils were incubated with the LQI-presenting phage (black line) alone or with the LQI-presenting phage and different LQI peptide constructs at the same time (blue line). Phage binding to neutrophils was quantified using anti-M13-PE antibody (only M13-PE=dotted line).

The present invention provides peptide sequences that specifically bind to neutrophils, molecules comprising said peptide sequences, in monomeric or multimeric forms, and complexes comprising them. The peptides in their various forms can be used for targeted in vivo delivery of therapeutic and/or diagnostic agents to neutrophils, in patients afflicted with cancer as well as infectious disease, inflammatory disease or disorder or inflammatory autoimmune disease or disorder associated with accumulation of neutrophils to a diseased or injured tissue or site. Neutrophils have a significant role in the overall immune response against these diseases or disorders and their modulation is a heretofore unexplored therapeutic avenue.

The present invention is based in part on the finding of several specific short peptide sequences that show highly specific binding to neutrophils. Tetramers and higher-level conjugations of the peptides showed ex vivo and in vivo binding to circulating neutrophils of healthy as well as diseased mice and humans, and was found to accumulate in the site of disease. It was also shown that the peptides do not affect neutrophil viability and function.

The present invention is further based in part on the discovery that after systemic TGFβ blockade, the phenotype of tumor-associated neutrophils (TANs) changes from a tumor-supportive phenotype into a pro-inflammatory tumor-suppressive phenotype, and that nanoparticles containing TGFβ inhibitor completely block TGFβ signaling in high-density mature neutrophils (High Density Neutrophils—HDNs). Without being bound to any theory or mechanism, it is hypothesized that the combination of a TGFβ inhibitor (e.g. SB-431542) with the peptide or peptides of the present invention can significantly strengthen the anti-tumor response of neutrophils in vivo and reduce systemic side effects.

It should be noted that Fridlender, Z. G., et al. (Cancer cell, 2009, 16(3) 183-194) showed that systemic blockade of TGFβ resulted in alteration of neutrophil phenotype from N2 TAN into N1 TAN. Targeting of the TGFβ inhibitor to neutrophils, using specific peptides and nanoparticles as carriers, can efficiently block TGFβ signaling in vivo in a targeted manner without other undesirable side effects.

In particular, the present invention provides peptides that bind to human or murine neutrophils, and uses thereof in treatment or diagnosis of a neutrophil-associated medical condition. In some embodiments, the medical condition is selected from the group consisting of cancer, infectious disease, inflammatory disease or disorder and autoimmune disease or disorder. Each possibility represents a separate embodiment of the present invention.

The term "neutrophils" as used herein refers to the type of leucocyte most numerous in mammals, which forms an important part of the innate immune system. Neutrophils form part of a family of polymorphonuclear cells (PMN) with basophils and eosinophils. Neutrophils are normally found in the bloodstream. During the starting (acute) phase of inflammation, particularly as a result of bacterial infection, and certain forms of cancer, neutrophils are among the first immune cells migrating towards the site of inflammation/tumor. They migrate through the blood vessels, then through interstitial tissue, following chemical signals, such as interleukin-8 (IL-8) and C5a. The term "neutrophils" as used herein encompasses all types of neutrophils, either mature, immature, high-density or low-density, including but not limited to High Density Neutrophils—HDNs and Low Density Neutrophils (LDNs).

The term "peptide" refers to a short chain of amino acid residues linked by peptide bonds, i.e., a covalent bond formed between the carboxyl group of one amino acid and an amino group of an adjacent amino acid. The term "peptide" refers to short sequences having up to 50 amino acids. A chain of amino acids monomers longer than 50 amino acid is referred as a "polypeptide". Such polypeptides, when having more than 50 amino acid residues, can also be classified as proteins, more particularly, proteins of low or medium molecular weight.

The term "peptide" encompasses also the term "peptide analog". The term "peptide analog" and "analog" are used herein interchangeably and refer to an analog of a peptide having at least 80% identity with the original peptide, wherein the analog retains the activity of the original peptide. Thus, the terms "analog" and "active analog" may be used interchangeably. The term "analog" refers to a peptide which contains substitutions, rearrangements, deletions, additions and/or chemical modifications in the amino acid sequence of the parent peptide. According to some embodiments, the peptide analog has at least 80%, at least 90% or at least 95% sequence identity to the original peptide. According to one embodiment, the analog has about 70% to about 95%, about 80% to about 90% or about 85% to about 95% sequence identity to the original peptide. According to some embodiments, the analog of the present invention comprises the sequence of the original peptide in which 1 or 2 deletions, additions and/or substitutions were made.

The term "peptide" encompasses also the term "peptide fragment". The term "fragment" refers to a fragment of the original peptide or of an analog thereof in which 1 or 2 amino acid residues have been deleted, wherein said fragment retains the activity of the original peptide or analog. Thus, the terms "fragment" and "active fragment" may be used interchangeably.

The substitutions of the amino acids may be conservative or non-conservative substitution. The non-conservative substitution encompasses substitution of one amino acid by any other amino acid. In one particular embodiment, the amino acid is substituted by a non-natural amino acid.

The term "analog" encompasses also the term "conservative analog". Conservative substitutions of amino acids as known to those skilled in the art are within the scope of the present invention. Conservative amino acid substitutions include replacement of one amino acid with another having the same type of functional group or side chain, e.g., aliphatic, aromatic, positively charged, negatively charged. One of skill will recognize that individual substitutions, is a "conservatively modified analog" where the alteration results in the substitution of an amino acid with a chemically similar amino acid. Conservative substitution tables providing functionally similar amino acids are well known in the art. One typical example of conservative substitution is provided below.

The following six groups each contain amino acids that are conservative substitutions for one another: (1) Alanine (A), Serine (S), Threonine (T); (2) Aspartic acid (D), Glutamic acid (E); (3) Asparagine (N), Glutamine (Q); (4) Arginine (R), Lysine (K); (5) Isoleucine (I), Leucine (L), Methionine (M), Valine (V); and (6) Phenylalanine (F), Tyrosine (Y), Tryptophan (W). In other embodiments, the conservative substitution encompass substitution with a chemically similar non-natural amino acid.

Thus, in some embodiments, the analog is a conservative analog of the peptide. According to some embodiments, the conservative analog of the present invention comprises the sequence of the original peptide in which 1 or 2 conservative substitutions were made. According to another embodiment, the analog consists of the amino acid sequence of the original peptide in which 1 or 2 conservative substitutions were made. Thus, the analog consists of the amino acid sequence of the original peptide with 1 or 2 conservative substitutions.

The term "amino acid" as used herein refers to an organic compound comprising both amine and carboxylic acid functional groups, which may be either a natural or non-natural amino acid. The twenty two natural amino acids are aspartic acid (Asp), tyrosine (Tyr), leucine (Leu), tryptophan (Trp), arginine (Arg), valine (Val), glutamic acid (Glu), methionine (Met), phenylalanine (Phe), serine (Ser), alanine (Ala), glutamine (Gln), glycine (Gly), proline (Pro), threonine (Thr), asparagine (Asn), lysine (Lys), histidine (His), isoleucine (Ile), cysteine (Cys), selenocysteine (Sec), and pyrrolysine (Pyl). Non-limiting examples of non-natural amino acids include diaminopropionic acid (Dap), diaminobutyric acid (Dab), ornithine (Orn), aminoadipic acid, β-alanine, 1-naphthylalanine, 3-(1-naphthyl)alanine, 3-(2-naphthyl)alanine, γ-aminobutiric acid (GABA), 3-(aminomethyl) benzoic acid, p-ethynyl-phenylalanine, p-propargly-oxy-phenylalanine, m-ethynyl-phenylalanine, p-bromophenylalanine, p-iodophenylalanine, p-azidophenylalanine, p-acetylphenylalanine, azidonorleucine, 6-ethynyl-tryptophan, 5-ethynyl-tryptophan, 3-(6-chloroindolyl)alanine, 3-(6-bromoindolyl)alanine, 3-(5-bromoindolyl)alanine, azidohomoalanine, p-chlorophenylalanine, α-aminocaprylic acid, O-methyl-L-tyrosine, N-acetylgalactosamine-α-threonine, and N-acetylgalactosamine-α-serine.

According to one embodiment, the substitution is substitution with a non-natural amino acid.

According to one aspect, the present invention provides a peptide comprising an amino acid sequence selected from the group consisting of:

KFPDLDSRRLPHMSL; (SEQ ID NO: 1)

LATTHMVFSPDH; (SEQ ID NO: 2)

PSSNLESTPLSLL; (SEQ ID NO: 3)

SSLMTTQLIATSI; (SEQ ID NO: 4)

PELDSKPYFPPL; (SEQ ID NO: 5)

ELVTASMPRPNN; (SEQ ID NO: 6)

SLESSPMAQLPQ; (SEQ ID NO: 7)

SELRSTPLLVPS; (SEQ ID NO: 8)

LQIQSWSSSP; (SEQ ID NO: 9)

STMTILGTGS; (SEQ ID NO: 10)

TETSLRIVSTNP; (SEQ ID NO: 11)

LSIVSGSALNHL; (SEQ ID NO: 12)
and

LTLVSERPMI; (SEQ ID NO: 13)

or a salt thereof.

According to another aspect, the present invention provides a peptide of up to 30 amino acids, wherein the peptide comprises an amino acid sequence selected from the group consisting of SEQ ID NO: 1 to 9 or a salt thereof.

According to another aspect, the present invention provides a peptide of up to 30 amino acids, wherein the peptide comprises an amino acid sequence selected from the group consisting of SEQ ID NO: 10 to 13 or a salt thereof.

According to another aspect, the present invention provides a peptide of up to 30 amino acids for use in targeting to neutrophils, wherein the peptide comprises an amino acid sequence selected from the group consisting of SEQ ID NO: 1 to 13 or a salt thereof.

According to one aspect, the present invention provides a peptide of up to 30 amino acids that binds to human neutrophils, said peptide comprising an amino acid sequence selected from the group consisting of: SEQ ID NO: 1 to 8.

According to another aspect, the present invention provides a peptide for use in targeting to human neutrophils, wherein the peptide comprises an amino acid sequence selected from the group consisting of SEQ ID NO: 1 to 8 or a salt thereof.

According to another aspect, the present invention provides a peptide that binds to murine neutrophils, said peptide comprising an amino acid sequence selected from the group consisting of SEQ ID NO: 9 to 13 or a salt thereof.

According to yet another aspect, the present invention provides a peptide of up to 30 amino acids for use in targeting to murine neutrophils, wherein the peptide comprises an amino acid sequence selected from the group consisting of SEQ ID NO: 9 to 13 or a salt thereof.

According to some embodiments, the peptide that binds to murine neutrophils consists of the amino acid sequence LQIQSWSSSP (SEQ ID NO: 9) or a salt thereof.

As used herein the term "salts" refers to both salts of carboxyl groups and to acid addition salts of amino or guanidino groups of the peptide molecule. Salts of carboxyl groups may be formed by means known in the art and include inorganic salts, for example sodium, calcium, ammonium, ferric or zinc salts, and the like, and salts with organic bases such as salts formed for example with amines such as triethanolamine, piperidine, procaine, and the like. Acid addition salts include, for example, salts with mineral acids such as, for example, acetic acid or oxalic acid. Salts describe here also ionic components added to the peptide solution to enhance hydrogel formation and/or mineralization of calcium minerals.

Without being bound to any theory or mechanism, it is proposed that the human- and the murine-neutrophil-binding peptides bind to the neutrophils via the human and mouse CD177, respectively.

According to some embodiments, the present invention provides a peptide binding to mouse CD177, said peptide comprising the amino acid sequence selected from SEQ ID NO: 9 to 13 or an analog or salt thereof.

According to other embodiments, the present invention provides a peptide binding to human CD177, said peptide comprising an amino acid sequence selected from SEQ ID NO: 1 to 8, or an analog or salt thereof.

Without being bound to any theory or mechanism, it is hypothesized that binding of different peptides to human vs. murine neutrophils results from the different structure of human and mouse CD177.

The peptides, analogs and salts of the present invention may be produced by any method known in the art, including recombinant and synthetic methods. Synthetic methods include exclusive solid phase synthesis, partial solid phase synthesis, fragment condensation, or classical solution synthesis. Solid phase peptide synthesis procedures are well known to one skilled in the art. Synthetic methods to produce peptides include but are not limited to FMOC solid phase peptide synthesis described, for example in Fields G. B., Noble R., Int. J. Pept. Protein Res., 35: 161-214, 1990.

In some embodiments, synthetic peptides are purified by preparative high-performance liquid chromatography and the peptide sequence is confirmed via amino acid sequencing by methods known to one skilled in the art.

In some embodiments, recombinant protein techniques, well known in the art, are used to generate peptides and peptide multimers (consisting of non-branched structures) of the present invention.

According to some embodiments, the peptide is a neutrophil binding peptide. According to some embodiments, the neutrophils are mammalian neutrophils. According to some embodiments, the neutrophils are rodent neutrophils. According to some embodiments, the neutrophils are murine neutrophils. According to some embodiments, the neutrophils are human neutrophils. According to some embodiments, the peptide is a neutrophil targeting peptide. According to some embodiments, the peptide is a CD177 binding peptide. According to some embodiments, the peptide is a CD177 targeting peptide. According to some embodiments, CD177 is mammalian CD177. According to some embodiments, CD177 is rodent CD177. According to some embodiments, CD177 is murine CD177. According to some embodiments, CD177 is human CD177.

According to some embodiments, the peptide comprises at most 500, 450, 400, 350, 300, 250, 200, 150, 100, 90, 80, 70, 60, 50, 45, 40, 35, 30, 25, 20, 15 or 10 amino acids. Each possibility represents a separate embodiment of the invention. In some embodiments, the peptide comprises at most 100 amino acids. In some embodiments, the peptide comprises at most 50 amino acids. In some embodiments, the peptide comprises at most 30 amino acids. In some embodiments, the peptide comprises up to 30 amino acids. In some embodiments, the peptide comprises at most 20 amino acids. In some embodiments, the peptide comprises at most 15 amino acids.

According to some embodiments, the peptide comprises 6-100, 6-50, 6-40, 6-30, 6-25, 6-20, 6-15, 5-12, 6-10, 10-100, 10-50, 10-40, 10-30, 10-25, 10-20, 10-15, 10-12, 12-100, 12-50, 12-40, 12-30, 12-25, 12-20, 12-15, 15-100, 15-50, 15-40, 15-30, 15-25, or 15-20, amino acids. Each possibility represents a separate embodiment of the present invention. According to some embodiments, the peptide comprises at least 6 amino acids. According to some embodiments, the peptide comprises at least 8 amino acids. According to some embodiments, the peptide comprises at least 10 amino acids. According to some embodiments, the peptide comprises at least 12 amino acids. According to some embodiments, the peptide comprises at least 15 amino acids.

According to some embodiments, the peptide comprises SEQ ID NO: 1. According to some embodiments, the peptide consists of SEQ ID NO: 1. According to some embodiments, the peptide comprises SEQ ID NO: 2. According to some embodiments, the peptide consists of SEQ ID NO: 2. According to some embodiments, the peptide comprises SEQ ID NO: 3. According to some embodiments, the peptide consists of SEQ ID NO: 3. According to some embodiments, the peptide comprises SEQ ID NO: 4. According to some embodiments, the peptide consists of SEQ ID NO: 4. According to some embodiments, the peptide comprises SEQ ID NO: 5. According to some embodiments, the peptide consists of SEQ ID NO: 5. According to some embodiments, the peptide comprises SEQ ID NO: 6. According to some embodiments, the peptide consists of SEQ ID NO: 6. According to some embodiments, the peptide comprises SEQ ID NO: 7. According to some embodiments, the peptide consists of SEQ ID NO: 7. According to some embodiments, the peptide comprises SEQ ID NO: 8. According to some embodiments, the peptide consists of SEQ ID NO: 8. According to some embodiments, the peptide comprises an amino acids sequence selected from the group consisting of SEQ ID NO: 1-8. According to some embodiments, the peptide consists of an amino acids sequence selected from the group consisting of SEQ ID NO: 1-8. In some embodiments, the peptide binds to human neutrophils and/or human CD177 and the peptide comprises or consists of an amino acids sequence selected from the group consisting of SEQ ID NO: 1-8. According to some embodiments, the peptide comprises an amino acids sequence selected from the group consisting of SEQ ID NO: 1-9. According to some embodiments, the peptide consists of an amino acids sequence selected from the group consisting of SEQ ID NO: 1-9.

According to some embodiments, the peptide comprises SEQ ID NO: 9. According to some embodiments, the peptide consists of SEQ ID NO: 9. According to some embodiments, the peptide comprises SEQ ID NO: 10. According to some embodiments, the peptide consists of SEQ ID NO: 10. According to some embodiments, the peptide comprises SEQ ID NO: 11. According to some embodiments, the peptide consists of SEQ ID NO: 11. According to some embodiments, the peptide comprises SEQ ID NO: 12. According to some embodiments, the peptide consists of SEQ ID NO: 12. According to some embodiments, the peptide comprises SEQ ID NO: 13. According to some embodiments, the peptide consists of SEQ ID NO: 13. According to some embodiments, the peptide comprises an amino acids sequence selected from the group consisting of SEQ ID NO: 9-13. According to some embodiments, the peptide consists of an amino acids sequence selected from the group consisting of SEQ ID NO: 9-13. In some embodiments, the peptide binds to human neutrophils and/or human CD177 and the peptide comprises or consists of an amino acids sequence selected from the group consisting of SEQ ID NO: 9-13.

According to some embodiments, the peptides comprise at least one cyclization. According to some embodiments, the peptides of the present invention are cyclic peptides. The term "cyclization" as used herein refers to an intramolecular bond between two non-adjacent amino acids. The terms "cyclic peptide" and "cyclopeptide" are used herein interchangeably and refer to a peptide having an intramolecular bond between two non-adjacent amino acids. The cyclization can be made through a covalent or non-covalent bond. Intramolecular bonds include, but are not limited to, backbone to backbone, side-chain to backbone and side-chain to side-chain bonds. According to some embodiments, the cyclization occurs between the N-terminal and C-terminal amino acids. According to some embodiments, the cyclization occurs via a spacer. According to some embodiments, the peptides are linear peptides.

According to some embodiments, the peptides of the present invention are conjugated to at least one moiety capable of increasing solubility. According to some embodiments, the peptides of the present invention are conjugated to at least one moiety capable of increasing permeability. According to some embodiments, the peptides of the present invention are conjugated at least one moiety capable of increasing solubility or permeability. According to some embodiments, at least one is a plurality of moieties. In some embodiments, a plurality is 2. In some embodiments, a plurality is at least 2, 3, 4, 5, 6, 7, 8, 9, or 10. Each possibility represents a separate embodiment of the invention.

According to other embodiments, the peptides of the present invention are conjugated to at least one linker or spacer. According to further embodiments, the peptides of the present invention are conjugated to at least one moiety capable of increasing solubility or permeability and optionally to at least one linker or spacer. According to yet further embodiments, the peptides of the present invention are conjugated to at least one moiety capable of increasing solubility or permeability and to at least one linker or spacer. According to yet further embodiments, the peptides of the present invention are conjugated to at least one moiety capable of increasing solubility or permeability and to at least one linker or spacer, wherein the at least one moiety capable of increasing solubility or permeability and the at least one linker or spacer are covalently linked to each other.

In some embodiments, the linker is an amino acid linker. In some embodiments, the linker is a chemical linker. In some embodiments, the linker is a bond. In some embodiments, the bond is a covalent bond. In some embodiments, the bond is a peptide bond. In some embodiments, the spacer is an amino acid spacer. In some embodiments, the linker or spacer comprises at least 1, 2, 3, 4, 5, 6, 7, 8, 9 or 10 amino acids. Each possibility represents a separate embodiment of the invention. In some embodiments, the linker or spacer is a single amino acid. In some embodiments, the linker or spacer comprises at most 1, 2, 3, 4, 5, 6, 7, 8, 9, 10, 11, 12, 13, 14, 15, 20, 25, 30, 35, 40, 45, 50, 60, 70, 75, 80, 90, or 100 amino acids. Each possibility represents a separate embodiment of the invention. In some embodiments, the linker or spacer comprises at most 1 amino acid. In some embodiments, the linker or spacer comprises at most 10 amino acids.

In some embodiments, the linker is a cysteine residue. In some embodiments, the linker is a lysine residue. In some embodiments, the linker is at least one repeat of the dipeptide lysine-alanine. In some embodiments, the linker is at least two repeats of the dipeptide KA. In some embodiments, the linker is two repeats of the dipeptide KA. In some embodiments, the linker comprises or consists of KAKA (SEQ ID NO: 16).

In some embodiments, a first peptide is separated from a second peptide by a spacer. In some embodiments, a first peptide is linked to a second peptide by a linker. In some embodiments, a peptide is separated from a moiety by a spacer. In some embodiments, a peptide is linked to a moiety by a linker. In some embodiments, a first moiety and a second moiety are separated by a spacer. In some embodiments, a first moiety and a second moiety are linked by a linker. In some embodiments, the linkage is a C-terminal linkage. In some embodiments, the linkage is an N-terminal linkage. In some embodiments, the linkage is not an N-terminal linkage. In some embodiments, there is no linkage to the N-terminus of the peptide. In some embodiments, the peptide comprises a free N-terminus.

According to some embodiments, the peptide is conjugated to at least one moiety via the peptide's C-terminus. According to some embodiments, the peptide is conjugated to the at least one linker or spacer via the peptide's C-terminus. According to some embodiments, the N-terminus of the peptide is not modified. According to other embodiments, the peptide has a free amine group on its N-terminus. Without being bound to any theory or mechanism, it is speculated that the amine group in the N-terminus of the peptides may be involved in the binding to neutrophils.

Moieties capable of increasing solubility are well known in the art and any such moiety may be employed for the peptide of the invention. Moieties that are capable of increasing solubility include but are not limited to: 8-amino-3,6-dioxaoctanoic acid (Doa) residues, polyethylene-glycol (PEG) in any length and peptides comprising the amino acid sequence GGGS (SEQ ID NO: 17) or GGGGS (SEQ ID NO: 18). In some embodiments, the moiety is a DOA residue. In some embodiments, the moiety is PEG. In some embodiments, the linker comprises at least one repeat of SEQ ID NO: 17. In some embodiments, the linker comprises at least one repeat of SEQ ID NO: 18. In some embodiments, the linker comprises or consists of at least 1, 2, 3, 4, or 5 repeats of SEQ ID NO: 17. Each possibility represents a separate embodiment of the invention. In some embodiments, the linker comprises or consists of at least 1, 2, 3, 4, or 5 repeats of SEQ ID NO: 18. Each possibility represents a separate embodiment of the invention.

According to specific embodiments, the moiety capable of increasing solubility comprises an 8-amino-3,6-dioxaoctanoic acid (Doa) residue. According to some embodiments, the peptides are conjugated to 1,2,3,4 or 5 Doa residues. Each possibility represents a separate embodiment of the present invention. According to some embodiments, the peptides are conjugated to 2 Doa residues. According to further embodiments, the Doa residues are covalently connected to each other, to the peptide sequence and/or to a linker. According to some embodiments, the peptides are conjugated to two units of Doa residues covalently connected to each other. In some embodiments, the covalent linkage is a peptide linkage. In some embodiments, the peptide and the residue are in a single amino acid chain.

The terms "conjugated" or "peptide conjugate" as used herein refer to a molecule in which a peptide moiety is attached (i.e., coupled or linked), either directly or via a linker or spacer, by means of covalent chemical bonding to at least one peptidic or non-peptidic molecule.

The terms "linker" and "spacer" are used herein interchangeably and refer to any molecule that covalently binds and therefore linking two molecules. Non-limiting examples of the linker are amino acids, peptides, or any other organic substance that can be used to allow distance between two linked molecules. According to specific embodiments, the linker is a flexible linker. According to specific embodiments, the linker is a flexible peptide. According to further specific embodiments, the linker is a flexible peptide comprising at least one glycine residue. According to particular embodiments, the linker comprises plurality of Lysine residues. According to some specific embodiments, the linker comprises 3-12 Lysine residues. According to particular embodiments, the linker comprises a 3-maleimidopropionic acid (Mpa) residue.

According to some embodiments, the present invention provides peptide conjugates comprising at least one peptide selected from SEQ ID NO: 1 to 13 and at least one moiety capable of increasing solubility. According to other embodiments, the present invention provides peptide conjugates comprising at least one peptide selected from SEQ ID NO: 1 to 13 and at least one linker or spacer. According to further embodiments, the peptide conjugates comprise at least one peptide selected from SEQ ID NO: 1 to 13, at least one moiety capable of increasing solubility and optionally at least one linker or spacer. According to yet further embodiments, the peptide conjugates comprise at least one peptide selected from SEQ ID NO: 1 to 13, at least one moiety capable of increasing solubility and at least one linker or spacer. According to yet further embodiments, the peptide conjugates comprise at least one moiety capable of increasing solubility—and at least one linker or spacer, wherein the at least one moiety capable of increasing solubility and the at least one linker or spacer are covalently linked to each other.

According to some embodiments, the peptide conjugates comprise at least one peptide selected from SEQ ID NO: 1 to 13 and 1,2,3,4 or 5 units of a Doa residue. Each possibility represents a separate embodiment of the present invention. According to further embodiments, the peptide conjugates comprise at least one peptide selected from SEQ ID NO: 1 to 13 and 2, 3, 4 or 5 units of a Doa residue, wherein the Doa residues are covalently connected to each other to the peptide sequence and/or to a linker.

According to further embodiments, the peptide conjugates comprise at least one peptide selected from SEQ ID NO: 1 to 13, at least one Doa residue and at least one Mpa residue.

According to some embodiments, the present invention provides peptide conjugates comprising the amino acid sequence LQIQSWSSSP (SEQ ID NO: 9) and at least one moiety capable of increasing solubility. According to other embodiments, the present invention provides peptide conjugates comprising SEQ ID NO: 9 and at least one linker or spacer. According to further embodiments, the peptide conjugates comprise SEQ ID NO: 9, at least one moiety capable of increasing solubility and optionally at least one linker or spacer. According to yet further embodiments, the peptide conjugates comprise SEQ ID NO: 9, at least one moiety capable of increasing solubility and at least one linker or spacer.

According to some embodiments, the peptide conjugates comprise SEQ ID NO: 9 and 1, 2, 3, 4 or 5 units of a Doa residue. Each possibility represents a separate embodiment of the present invention. According to further embodiments, the peptide conjugates comprise SEQ ID NO: 9 and 2, 3, 4 or 5 units of a Doa residue, wherein the Doa residues are covalently connected to each other, to the peptide sequence and/or to a linker.

According to further embodiments, the peptide conjugates comprise SEQ ID NO: 9, at least one Doa residue and at least one Mpa residue.

According to some embodiments, the peptide conjugate comprises at least one moiety capable of increasing solubility, wherein the at least one moiety is conjugated to the peptide via the peptide's C-terminus. According to some embodiments, peptide conjugate comprises at least one linker or spacer, wherein the at least one linker or spacer is conjugated to the peptide via the peptide's C-terminus. According to some embodiments, the N-terminus of the peptide conjugate is not modified. According to other embodiments, the peptide conjugate has a free amine group on its N-terminus.

According to some embodiments, the peptide conjugate has a structure according to Formula III:

Peptide-Doa-Doa-C  (Formula III)

wherein "C" is a Cysteine residue, and wherein "Peptide" denotes a peptide of the invention or a salt thereof. In some embodiments, "Peptide" denotes a peptide of the invention or a salt thereof.

According to another aspect, there is provided a peptide multimer, comprising a plurality of peptides of the invention.

According to some embodiments, the plurality of peptides is a plurality of same peptide. According to some embodiments, the plurality of peptides is a plurality of different peptides. According to some embodiments, the peptides are identical or different peptides. According to some embodiments, the present invention provides a peptide multimer comprising a plurality of identical or different peptides selected from peptides of the invention or salts thereof. According to other embodiments, the present invention provides a peptide multimer for use in targeting to human neutrophils, wherein the peptide multimer comprises a plurality of identical or different peptides selected from the group consisting of SEQ ID NO: 1-8 or salts thereof. According to other embodiments, the present invention provides a peptide multimer for use in targeting to murine neutrophils, wherein the peptide multimer comprises a plurality of identical or different peptides selected from the group consisting of SEQ ID NO: 9-13 or salts thereof.

The terms "peptide multimer" and "multimeric peptide" are used interchangeably herein and refer to a construct that contains a plurality (at least two, typically at least three or more) of peptides, not necessarily adjacent.

According to some embodiments, the peptide multimer is a branched molecule. According to other embodiments, the peptide multimer is a non-branched molecule. According to other embodiments, the peptide multimer is a linear molecule. According to other embodiments, the peptide multimer is a circular molecule.

According to some embodiments, the peptide multimer comprises at most 4, 6, 8, 10, 12, 14, 16, 18, 20, 25, 30, 35, 40, 45 or 50 peptides. Each possibility represents a separate embodiment of the present invention. According to some embodiments, the peptide multimer comprises at least 2, 4, 6, 8, 10, 12, 14, or 16 peptides. Each possibility represents a separate embodiment of the present invention. According to some embodiments, the peptide multimer comprises 2-20, 2-16, 2-14, 2-12, 2-10, 2-8, 2-6 or 2-4 identical or different peptides. Each possibility represents a separate embodiment of the present invention. According to some embodiments, the peptide multimer comprises 2-20, 2-16, 2-14, 2-12, 2-10, 2-8, 2-6 or 2-4 peptides. Each possibility represents a separate embodiment of the present invention. According to some embodiments, the peptide multimer comprises 2-20 peptides. According to some embodiments, the peptide multimer comprises 2-4 peptides. According to some embodiments, the peptide multimer comprises 2 peptides. According to some embodiments, the peptide multimer comprises 4 peptides. According to some embodiments, the peptide multimer comprises 16 peptides. According to specific embodiments, the peptide multimer comprises 4 identical or different peptides.

According to some embodiments, the peptides in the peptide multimer are covalently linked to each other directly or through a linker or spacer. According to other embodiments, the peptides in the peptide multimer are covalently linked to a scaffold directly or through a linker or spacer.

According to some embodiments, the peptide multimer comprises a plurality of identical or different peptide conjugates. According to some embodiments, the peptide multimer comprises peptide conjugates comprising at least one peptide selected from SEQ ID NO: 1-8. According to some embodiments, the peptide multimer comprises peptide conjugates comprising at least one peptide selected from SEQ ID NO: 9-13. According to other embodiments, the peptide multimer comprises peptide conjugates comprising at least one peptide having the sequence LQIQSWSSSP (SEQ ID NO: 9). According to some embodiments, the peptide multimer comprises 2-20, 2-16, 2-14, 2-12, 2-10, 2-8, 2-6 or 2-4 identical or different peptide conjugates comprising at least one peptide selected from SEQ ID NO: 1-8. According to other embodiments, the peptide multimer comprises 2-20, 2-16, 2-14, 2-12, 2-10, 2-8, 2-6 or 2-4 identical or different peptide conjugates comprising at least one peptide selected from SEQ ID NO: 9-13. According to specific embodiments, the peptide multimer comprises 4 identical or different peptide conjugates.

According to some embodiments, the peptide conjugates in the peptide multimer are covalently linked to each other directly or through a linker or spacer. According to other embodiments, the peptide conjugates in the peptide multimer are covalently linked to a scaffold directly or through a linker or spacer. According to further embodiments, the peptide conjugates in the peptide multimer are non-covalently linked to a scaffold directly or through a linker or spacer. According to some embodiments, the scaffold is a branched scaffold. According to other embodiments, the scaffold is a non-branched scaffold.

According to some embodiments, each one of the peptides or peptide conjugates is bound to the scaffold directly or via a linker or spacer. According to other embodiments, the peptides or peptide conjugates are covalently attached to each other and at least one peptide/peptide conjugate is bound to the scaffold directly or via a linker or spacer.

According to some embodiments, the scaffold is a peptidic or polypeptidic scaffold. According to other embodiments, the peptidic or polypeptidic scaffold connects the peptides to each other on a single location in the scaffold, or to a different location on a scaffold. Each possibility represents a separate embodiment of the invention. According to some embodiments, the scaffold comprises at least one Lysine (Lys) residue. According to other embodiments, the scaffold comprises at least three Lys residues. According to further embodiments, the at least three Lys residues are connected together by amide bonds to form a branched multimeric scaffold. According to some embodiments, at least one amide bond is formed between the epsilon amine of a Lys residue and the carboxy group of another Lys residue.

According to a particular embodiment, the peptide multimer comprises the molecule Mpa-Cysteine-peptide.

According to a particular embodiment, the peptide multimer comprises a molecule of the scheme:

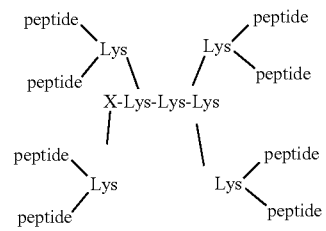

wherein X represents the peptide's C-terminus selected from carboxy acid, amide or alcohol group and optionally a linker or spacer, and each "peptide" independently denotes a peptide of the invention or a salt thereof.

According to some specific embodiments, at least one of the peptides is present in multiple copies. According to some embodiments, the multiple copies are linked thereby forming a multi-target peptide multimer. According to some embodiments, the peptide copies are linked through a linker. According to other embodiments, the peptide copies are linked directly. According to further embodiments, the multimer comprises copies linked both directly and via a linker.

According to some embodiments, the peptide multimer comprises a plurality of neutrophil-binding peptides arranged in an alternating sequential polymeric structure $B(X_1X_2X_3 \ldots X_m)_nB$ or in a block copolymer structure $B(X_1)_nZ(X_2)_nZ(X_3)_nZ \ldots (X_m)_n$, wherein B is an optional sequence of 1-10 amino acid residues; n is at each occurrence independently an integer of 2-50; m is an integer of 3-50; each of $X_1, X_2 \ldots X_m$ is an identical or different peptide of the invention; Z at each occurrence is a bond or a spacer of 1-4 amino acid residues. Each possibility represents a separate embodiment of the present invention.

The term "block copolymer structure" means that all the copies of a single peptide contained in the multimer are arranged adjacently.

According to some embodiments, the scaffold comprises or formed from a polyethylene glycol (PEG) molecule(s) or a modified PEG molecule(s). According to certain embodiments, the scaffold comprises a branched PEG molecule. According to some embodiments, the branched molecule comprises at least two sites available to bind a peptide of the present invention. According to other embodiments, the scaffold comprises from 2 to 100, 3 to 90, 4 to 60, 5 to 50, 6 to 40, 7 to 35, 8 to 30, 9 to 25 or 10 to 20, or 2 to 50 sites available to bind a peptide.

According to some embodiments, the PEG molecule is a branched molecule, comprising at least two separate connections to a peptide. According to other embodiments, the PEG is bound to additional PEG molecules. According to certain embodiments, multiple PEG molecules are bound to provide a multi-armed PEG molecule. According to certain embodiments, the peptides are connected to the PEG scaffold through amide bonds formed between amino groups of an NH$_2$-PEG molecule. According to yet other embodiments, at least one peptide is connected to PEG scaffold though a Lys residue.

According to some embodiments, the peptide multimer comprises a branched scaffold comprising at least one Lys residue linked to the peptides or peptide conjugates directly or through a spacer or linker. According to specific embodiments, the peptide multimer comprises a branched scaffold comprising at two Lys residues linked to the peptides or peptide conjugates directly or through a spacer or linker. According to further specific embodiments, the peptide multimer comprises a branched scaffold comprising the amino acid sequence Lys-Ala-Lys-Ala (KAKA, SEQ ID NO: 16) linked to the peptides or peptide conjugates directly or through a spacer or linker.

According to some embodiments, the peptide multimer further comprises a biotin moiety covalently attached to said peptide multimer directly or via a spacer or linker. According to some embodiments, the biotin is attached to said peptide multimer through the C-terminus. The biotin moiety makes the peptide multimer accessible for fluorescent detection and manipulation. According to other embodiments, the peptide multimer further comprises a biotin moiety, wherein the biotin moiety is non-covalently attached to said peptide multimer. According to some embodiments, the peptide multimer further comprises an avidin moiety attached to said peptide multimer directly or via a spacer or linker. According to some embodiments, the peptide multimer further comprises a streptavidin moiety attached to said peptide multimer directly or via a spacer or linker. According to further embodiments, the peptide multimer comprises a biotin moiety and an avidin/streptavidin moiety attached to each other through biotin-avidin interactions.

According to some embodiments, the multimeric peptide is homo-multimeric. According to other embodiments, the multimeric peptide is hetero-multimeric.

As used herein, the term "homo-multimeric" refers to a multimeric peptide comprising multiple copies of a single peptide. According to some embodiments, the multimeric peptide comprises 2-20, 2-16, 2-14, 2-12, 2-10, 2-8, 2-6 or 2-4 identical peptides. According to some embodiments, the multimeric peptide comprises 2-20, 2-16, 2-14, 2-12, 2-10, 2-8, 2-6 or 2-4 copies of a peptide comprising the amino acid sequence KFPDLDSRRLPHMSL (SEQ ID NO: 1). Each possibility represents a separate embodiment of the invention. According to some embodiments, the multimeric peptide comprises 2-20, 2-16, 2-14, 2-12, 2-10, 2-8, 2-6 or 2-4 copies of a peptide comprising the amino acid sequence LATTHMVFSPDH (SEQ ID NO: 2). Each possibility represents a separate embodiment of the invention. According to some embodiments, the multimeric peptide comprises 2-20, 2-16, 2-14, 2-12, 2-10, 2-8, 2-6 or 2-4 copies of a peptide comprising the amino acid sequence PSSNLESTPLSLL (SEQ ID NO: 3). Each possibility represents a separate embodiment of the invention. According to some embodiments, the multimeric peptide comprises 2-20, 2-16, 2-14, 2-12, 2-10, 2-8, 2-6 or 2-4 copies of a peptide comprising the amino acid sequence SSLMTTQLIATSI (SEQ ID NO: 4). Each possibility represents a separate embodiment of the invention. According to some embodiments, the multimeric peptide comprises 2-20, 2-16, 2-14, 2-12, 2-10, 2-8, 2-6 or 2-4 copies of a peptide comprising the amino acid sequence PELDSKPYFPPL (SEQ ID NO: 5). Each possibility represents a separate embodiment of the invention. According to some embodiments, the multimeric peptide comprises 2-20, 2-16, 2-14, 2-12, 2-10, 2-8, 2-6 or 2-4 copies of a peptide comprising the amino acid sequence ELVTASMPRPNN (SEQ ID NO: 6). Each possibility represents a separate embodiment of the invention. According to some embodiments, the multimeric peptide comprises 2-20, 2-16, 2-14, 2-12, 2-10, 2-8, 2-6 or 2-4 copies of a peptide comprising the amino acid sequence SLESSPMAQLPQ (SEQ ID NO: 7). Each possibility represents a separate embodiment of the invention. According to some embodiments, the multimeric peptide comprises 2-20, 2-16, 2-14, 2-12, 2-10, 2-8, 2-6 or 2-4 copies of a peptide comprising the amino acid sequence SELRSTPLLVPS (SEQ ID NO: 8). Each possibility represents a separate embodiment of the invention. According to some embodiments, the multimeric peptide comprises 2-20, 2-16, 2-14, 2-12, 2-10, 2-8, 2-6 or 2-4 copies of a peptide comprising the amino acid sequence LQIQSWSSSP (SEQ ID NO: 9). Each possibility represents a separate embodiment of the invention. According to some embodiments, the multimeric peptide comprises 2-20, 2-16, 2-14, 2-12, 2-10, 2-8, 2-6 or 2-4 copies of a peptide comprising the amino acid sequence STMTILGTGS (SEQ ID NO: 10). Each possibility represents a separate embodiment of the invention. According to some embodiments, the multimeric peptide comprises 2-20, 2-16, 2-14, 2-12, 2-10, 2-8, 2-6 or 2-4 copies of a peptide comprising the amino acid sequence TETSLRIVSTNP (SEQ ID NO: 11). Each possibility represents a separate embodiment of the invention. According to some embodiments, the multimeric peptide comprises 2-20, 2-16, 2-14, 2-12, 2-10, 2-8, 2-6 or 2-4 copies of a peptide comprising the amino acid sequence LSIVSGSALNHL (SEQ ID NO: 12). Each possibility represents a separate embodiment of the invention. According to some embodiments, the multimeric peptide comprises 2-20, 2-16, 2-14, 2-12, 2-10, 2-8, 2-6 or 2-4 copies of a peptide comprising the amino acid sequence LTLVSERPMI (SEQ ID NO: 13). Each possibility represents a separate embodiment of the invention. According to specific embodiments, the multimeric peptide is a tetramer comprising 4 copies of a peptide comprising an amino acid sequence selected from the group consisting of SEQ ID NO: 1 to 13. Each possibility represents a separate embodiment of the present invention. According to specific embodiments, the multimeric peptide is a tetramer comprising 4 copies of a peptide comprising the amino acid sequence selected from SEQ ID NO: 1 to 8. According to specific embodiments, the multimeric peptide is a tetramer comprising 4 copies of a peptide comprising the amino acid sequence selected from SEQ ID NO: 9 to 13. According to other embodiments, the multimeric peptide is a tetramer comprising 4 copies of a peptide comprising the amino acid sequence KFPDLDSRRLPHMSL (SEQ ID NO: 1). According to other embodiments, the multimeric peptide is a tetramer comprising 4 copies of a peptide comprising the amino acid sequence LQIQSWSSSP (SEQ ID NO: 9).

The term "hetero-multimeric" as used herein refers to a multimeric peptide comprising one or more copies of at least two different peptides. The term "different peptides" refers to peptides having different sequence and not to two copies of the same peptide. According to some embodiments, the multimeric peptide comprises one or more copies of at least two different peptides of the invention. According to specific embodiments, the multimeric peptide comprises one or more copies of at least two different peptides of the invention.

According to some embodiments, the hetero multimeric peptide comprises 2, 3, 4, 5, 6, 7 or 8 different peptide sequences of the invention or a salt thereof.

It has been shown that a peptide multimer comprising 4 copies of a single neutrophil-binding peptide, binds more efficiently to circulating neutrophils than a monomer of the peptide. Without being bound to any theory or mechanism, it is believed that a hetero-multimeric peptide comprising at least two substantially different peptides would target even higher percent of neutrophils than a homo-multimeric peptide.

According to some embodiments, the hetero-multimeric peptide comprises 2-20, 2-10 or 2-5 copies of at least one of the different peptides. According to other embodiments, the hetero-multimeric peptide comprises 2-20, 2-10 or 2-5 copies of at least two of the different peptides. According to further embodiments, the hetero-multimeric peptide comprises 2-20, 2-10 or 2-5 copies of at least three of the different peptides. Each possibility represents a separate embodiment of the present invention.

According to specific embodiments, the peptide multimer is a tetramer peptide presenting the neutrophil-binding peptide on 4 branches. According to further embodiments, at least one peptide in the tetramer has a free amine group on its N-terminus. According to yet further embodiments, each one of the neutrophil-binding peptides in the tetramer has a free amine group on the N-terminus. According to specific embodiments, the multimer peptide is a tetramer peptide presenting 4 copies of one neutrophil-binding peptide on 4 branches. According to further specific embodiments, the multimer peptide is a tetramer peptide presenting 4 copies of one neutrophil-binding peptide on 4 branches, wherein at least one copy of the neutrophil-binding peptide has a free amine group on its N-terminus. According to further embodiments, the multimer peptide is a tetramer peptide presenting 4 copies of one neutrophil-binding peptide on 4 branches, wherein each one of the copies of the neutrophil-binding peptide has a free amine group on its N-terminus.

According to some specific embodiments, the peptide multimer comprises a structure according to Formula I:

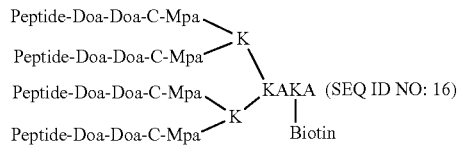

Formula I wherein each "Peptide" independently denotes a peptide of the invention or a salt thereof.

According to some embodiments, the peptide multimer comprises a structure according to Formula I, wherein each "Peptide" independently denotes a peptide of the invention or a salt thereof, wherein at least 2 peptides are different. According to other embodiments, the peptide multimer comprises a structure according to Formula I, wherein each "Peptide" independently denotes a peptide of the invention or a salt thereof, wherein at least 3 peptides are different. According to other embodiments, the peptide multimer comprises a structure according to Formula I, wherein each "Peptide" independently denotes a different peptide sequence, wherein each peptide sequence comprises a sequence selected from the group consisting of SEQ ID NO: 1 to 13 or a salt thereof. According to some embodiments, the peptide multimer comprises a structure according to Formula I, wherein each "Peptide" independently denotes a peptide of the invention or a salt thereof, wherein at least 2 peptides are identical. According to other embodiments, the peptide multimer comprises a structure according to Formula I, wherein each "Peptide" independently denotes a peptide of the invention or a salt thereof, wherein at least 3 peptides are identical. According to yet other embodiments, the peptide multimer comprises a structure according to Formula I, wherein "Peptide" denotes a peptide of the invention or a salt thereof. According to other embodiments, the peptide multimer comprises a structure according to Formula I, wherein each "Peptide" independently denotes a peptide of the invention or a salt thereof, wherein 4 peptides are identical.

According to some embodiments, the peptide multimer comprises a structure according to Formula I, wherein "Peptide" denotes a peptide comprising the amino acid sequence of SEQ ID NO: 1 or a salt thereof. According to some embodiments, the peptide multimer comprises a structure according to Formula I, wherein "Peptide" denotes a peptide consisting of the amino acid sequence of SEQ ID NO: 1 or a salt thereof. According to some embodiments, the peptide multimer comprises a structure according to Formula I, wherein "Peptide" denotes a peptide comprising the amino acid sequence of SEQ ID NO: 9 or a salt thereof. According to some embodiments, the peptide multimer comprises a structure according to Formula I, wherein "Peptide" denotes a peptide consisting of the amino acid sequence of SEQ ID NO: 9 or a salt thereof.

According to some specific embodiments, the peptide multimer comprises a structure according to Formula II:

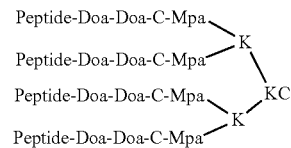

Formula II wherein each "Peptide" independently denotes a peptide of the invention or a salt thereof.

According to some embodiments, the peptide multimer comprises a structure according to Formula II, wherein each "Peptide" independently denotes a peptide of the invention or a salt thereof, wherein at least 2 peptides are different. According to other embodiments, the peptide multimer comprises a structure according to Formula II, wherein each "Peptide" independently denotes a peptide of the invention or a salt thereof, wherein at least 3 peptides are different. According to other embodiments, the peptide multimer comprises a structure according to Formula II, wherein each "Peptide" independently denotes a different peptide sequence, wherein each peptide sequence comprises a sequence selected from the group consisting of SEQ ID NO: 1 to 13 or a salt thereof. According to some embodiments, the peptide multimer comprises a structure according to Formula II, wherein each "Peptide" independently denotes a peptide of the invention or a salt thereof, wherein at least 2 peptides are identical. According to other embodiments, the peptide multimer comprises a structure according to Formula II, wherein each "Peptide" independently denotes a peptide of the invention or a salt thereof, wherein at least 3 peptides are identical. According to yet other embodiments, the peptide multimer comprises a structure according to Formula II, wherein "Peptide" denotes a peptide of the invention or a salt thereof. According to other embodiments, the peptide multimer comprises a structure according to Formula II, wherein each "Peptide" independently denotes a peptide of the invention or a salt thereof, wherein 4 peptides are identical.

According to some embodiments, the peptide multimer comprises a structure according to Formula II, wherein "Peptide" denotes a peptide comprising the amino acid sequence of SEQ ID NO: 1 or a salt thereof. According to some embodiments, the peptide multimer comprises a structure according to Formula II, wherein "Peptide" denotes a peptide consisting of the amino acid sequence of SEQ ID NO: 1 or a salt thereof. According to some embodiments, the peptide multimer comprises a structure according to Formula II, wherein "Peptide" denotes a peptide comprising the amino acid sequence of SEQ ID NO: 9 or a salt thereof. According to some embodiments, the peptide multimer comprises a structure according to Formula II, wherein "Peptide" denotes a peptide consisting of the amino acid sequence of SEQ ID NO: 9 or a salt thereof.

According to another aspect, there is provided a peptide complex comprising at least two peptide multimers of the invention.

According to some embodiments, the present invention provides a peptide complex comprising at least two peptide multimers. As used herein, the term "peptide complex" refers to a construct that contains a plurality (at least two, typically at least three or more) of identical or different peptide multimers, not necessarily adjacent. According to some embodiments, the peptide complex comprises at least two peptide multimers, wherein the peptide multimers comprise at least one peptide of the invention or a salt thereof. According to certain embodiments, the present invention provides a peptide complex for use in targeting to human neutrophils wherein the peptide complex comprises at least two peptide multimers, wherein the peptide multimers comprise at least one peptide comprising a sequence selected from SEQ ID NO: 1 to 13 or a salt thereof. According to some embodiments, the peptide complex comprises at least two peptide multimers, wherein the peptide multimers comprise at least two peptides comprising the amino acid sequence of SEQ ID NO: 9 or a salt thereof. According to some embodiments, the peptide complex comprises at least two peptide multimers, wherein the peptide multimers comprise at least two peptides comprising the amino acid sequence of SEQ ID NO: 1 or a salt thereof. According to certain embodiments, the present invention provides a peptide complex for use in targeting to murine neutrophils wherein the peptide complex comprises at least two peptide multimers, wherein the peptide multimers comprise at least one peptide comprising SEQ ID NO: 9 or a salt thereof. According to certain embodiments, the present invention provides a peptide complex for use in targeting to human neutrophils wherein the peptide complex comprises at least two peptide multimers, wherein the peptide multimers comprise at least one peptide comprising SEQ ID NO: 1 or a salt thereof. According to some embodiments, the peptide multimers in the peptide complex are covalently connected to each other directly or via a linker or spacer. According to some embodiments, the linker or spacer is selected from the group consisting but not limited to amino acids, peptides, and any other organic substance that can be used to allow distance between two linked molecules. According to other embodiments, the peptide multimers in the peptide complex are non-covalently attached to each other. According to some embodiments, the peptide multimers in the peptide complex are non-covalently attached to each other through a biotin-avidin interactions. According to some embodiments, the peptide complex comprises at least two biotin moieties and an avidin/streptavidin moiety, wherein the at least two biotin moieties are covalently attached to the peptide multimers, and wherein the avidin/streptavidin moiety is non-covalently attached to the biotin moieties. According to specific embodiments, the peptide complex comprises 4 peptide multimers and an avidin/streptavidin moiety, wherein each one of the peptide multimers is covalently attached to a biotin moiety, and wherein the 4 peptide multimers are non-covalently attached to the avidin/streptavidin moiety.

According to another aspect, there is provided a composition comprising a peptide of the invention, a peptide multimer of the invention or a peptide complex of the invention.

According to some embodiments, the peptide, peptide multimer or peptide complex is attached to a therapeutic agent. According to some embodiments, the peptide, peptide multimer or peptide complex is attached to a diagnostic agent. According to some embodiments, attached is directly attached. According to some embodiments, attached is attached via a linker. According to some embodiments, attached is attached via a carrier. According to some embodiments, attached is covalently attached. According to some embodiments, attached is attached via a carrier. According to some embodiments, attached is non-covalently attached.

According to some embodiments, the peptide, peptide multimer or peptide complex is attached to a therapeutic or diagnostic agent directly or through a carrier or linker. Each possibility represents a separate embodiment of the present invention. According to particular embodiments, the peptide, peptide multimer or peptide complex is covalently attached to the therapeutic/diagnostic agent directly or through a linker or spacer. Each possibility represents a separate embodiment of the present invention. According to other embodiments, the peptide, peptide multimer or peptide complex is non-covalently attached to the therapeutic/diagnostic agent. According to some embodiments, the peptide, peptide multimer or peptide complex is attached to a therapeutic or diagnostic agent through a carrier, wherein the carrier is a particle, wherein the size of the particle is in the sub-micron range. In some embodiments, the carrier is a particle. In some embodiments, the particle is a sub-micron size particle. In some embodiments, the particle is a nanoparticle (NP). According to particular embodiments, the peptide, peptide conjugate, peptide multimer or peptide complex is attached to a therapeutic or diagnostic agent through a carrier, wherein the carrier is a nanoparticle. According to further embodiments, the peptide, peptide conjugate, peptide multimer or peptide complex is attached to a therapeutic or diagnostic agent through a carrier, wherein the carrier is a nanoparticle encapsulating or coated with said therapeutic or diagnostic agent. Each possibility represents a separate embodiment of the present invention.

In the context of the present invention, the term "nanoparticle" refers to a particle having an average size of up to about 1000 nm, as determined by any method known in the art, for example dynamic light scattering (DLS) for determining the hydrodynamic diameter of the particles and transmission electron microscopy (TEM) for determining the accurate geometric nanoparticle size. According to some embodiments, the size of the nanoparticle is within the range of 50-1000, 100-1000, 200-1000, 250-1000, 300-1000, 500-1000, 600-1000, 700-1000, 50-900, 100-900, 200-900, 250-900, 300-900, 500-900, 600-900, 700-900, 50-800, 100-800, 200-800, 250-800, 300-800, 500-800, 600-800, 700-800, 50-600, 100-600, 200-600, 250-600, 300-600, 500-600, or 50-200 nm. Each possibility represents a separate embodiment of the present invention. According to some embodiments, the nanoparticle is selected from a nanosphere and a nanorod. As used herein, the term "nanosphere" refers to a nanoparticle having a spherical shape. The term "nanorod" refers to a nanoparticle having a rod-like shape. According to some embodiments, the nanoparticle is a liposome. According to other embodiments, the nanoparticle is a polymeric nanoparticle. According to additional embodiments, the polymeric nanoparticle comprises poly(lactic-co-glycolic acid) (PLGA). According to additional embodiments, the nanoparticle is a metallic nanoparticle. According to particular embodiments, the nanoparticle is fluorescently-labeled. According to some embodiments, the nanoparticle is modified with PEG. According to some embodiments, the nanoparticle comprises a PLGA core. In some embodiments, the nanoparticle is coated with a reactive agent. In some embodiments, the reactive agent is suitable for conjugating the peptide, peptide multimer or peptide complex to the nanoparticle. Reactive groups for conjugation are well known in the art and examples of such are provided herein below. According to some embodiments, the reactive group is a binding or capture group. In some embodiments, the binding or capture group is for binding or capturing a peptide or a linker or spacer. In some embodiments, the reactive group is streptavidin (SA). In some embodiments, the SA is for binding a peptide/multimer/complex comprising biotin. In some embodiments, the reactive group is a thiol. In some embodiments, the thiol if for binding a peptide/multimer/complex comprising a cysteine. In some embodiments, the cysteine is a free cystine. In some embodiments, the cysteine is in a linker. In some embodiments, the linkage is a maleimide linkage.

In some embodiments, the nanoparticle encapsulates the agent. In some embodiments, the nanoparticle comprises a hydrophilic core and the agent is in the core. In some embodiments, the nanoparticle comprises a hydrophobic core and the agent is in the core. In some embodiments, the agent is associated with the surface of the nanoparticle. In some embodiments, the agent is linked or conjugated to the surface of the nanoparticle. In some embodiments, the agent is a hydrophobic agent. In some embodiments, the agent is a hydrophilic agent.

In some embodiments, the agent is a neutrophil modifying agent. In some embodiments, the agent is a neutrophil modifying therapeutic agent. In some embodiments, the agent blocks reactive oxidation species (ROS) production. In some embodiments, the agent is a ROS inhibiting agent. In some embodiments, a ROS inhibiting agent is a flavoenzyme inhibitor. In some embodiments, the agent is an exocytosis inhibitor. In some embodiments, the agent blocks degranulation. In some embodiments, the agent is a degranulation inhibiting agent. In some embodiments, the agent is a cytotoxic agent. In some embodiments, cytotoxic is cell cytotoxic. In some embodiments, the cell is a neutrophil. In some embodiments, the agent is selected from the group consisting of TGF-β inhibitor, an exocytosis inhibitor and a flavoenzyme inhibitor.

According to some embodiments, the peptide, peptide multimer or peptide complex is attached to a therapeutic agent directly or through a carrier, wherein the therapeutic agent is a TGFβ inhibitor. According to some embodiments, the therapeutic agent is a TGFβ inhibitor. According to particular embodiments, the TGFβ inhibitor is SB-431542. TGFβ inhibitors are well known in the art and any such inhibitor can be used as the therapeutic agent.

According to some embodiments, the therapeutic agent is a flavoenzyme inhibitor. According to some embodiments, the flavoenzyme is a membrane flavoenzyme. According to some embodiments, the membrane flavoenzyme is a nicotinamide adenine dinucleotide phosphate(NADPH) oxidase. According to some embodiments, the NADPH oxidase is inhibitor diphenyleneiodonium (DPI). According to some embodiments, the flavoenzyme inhibitor is DPI. According to some embodiments, the therapeutic agent is selected from Sinomenine and *Ginko Biloba*. According to some embodiments, the therapeutic agent is Sinomenine. According to some embodiments, the therapeutic agent is *Ginko Biloba*. Flavoenzyme inhibitors are well known in the art and any such inhibitor may be used as the therapeutic agent of the invention.

According to some embodiments, the therapeutic agent is an exocytosis inhibitor. In some embodiments, the therapeutic agent is a neutrophil exocytosis inhibitor. In some embodiments, the exocytosis inhibitor is Nexinhib-20. Exocytosis inhibitors are well known in the art and any such inhibitor may be used as the therapeutic agent of the invention.

According to some embodiments, the peptides of the present invention are stable in serum at 37° C. for at least 10, 20, 30, 40, 50 or 60 minutes. Each possibility represents a separate embodiment of the present invention.

The serum includes various proteases mostly belonging to the coagulations cascade like factor XI or thrombin. Most of these proteases are serine proteases known to have similar substrate specificity as trypsin i.e., cleavage of peptide bonds after positive charged amino acids (Arg, Lys). Without being bound to any theory or mechanism, it is hypothesized that the peptides of the present invention which do not comprise positively-charged amino acid (e.g., LQIQSWSSSP, SEQ ID NO: 9), may be excluded from proteolytic degradation in serum.

According to some embodiments, the peptides of the invention are conjugated to a stabilizing agent.

The peptides, peptide conjugates and peptide multimers of the invention do not impair viability of neutrophils or viability of other blood cells. According to some embodiments, the peptides, peptide conjugates and peptide multimers do not impair neutrophil function. According to particular embodiments, the peptides, peptide conjugates and peptide multimers do not impair neutrophil activation, ROS production, migration and/or cytotoxicity towards cancer cells.

Neutrophil activation, migration and ROS production can be examined by methods known in the art, including for example determining the surface expression of CD11b as a proxy for neutrophil activation; Boyden chamber assay for testing neutrophil migration; and luminol based assay to determine the extent of ROS production.

According to some embodiments, the present invention provides a nanoparticle comprising a core particle and a plurality of at least one of the peptides or peptide multimers/complexes as detailed in the present invention, wherein the peptides or peptide multimers/complexes are attached to the outer surface of said core particle.

As used herein the term "core particle" refers to a nanoparticle that can be surrounded or coated with the peptides or peptide multimers/complexes of the invention. The peptides or peptide multimers/complexes can be attached to the outer surface of the core particle via covalent or non-covalent bonds.

According to particular embodiments, the present invention provides a nanoparticle comprising a core particle and at least one peptide of the invention, wherein the at least one peptide is attached to the outer surface of said core particle. In some embodiments, at least one is a plurality.

According to some embodiments, the present invention provides a nanoparticle comprising a core particle and at least one peptide comprising the amino acid sequence KFPDLDSRRLPHMSL (SEQ ID NO: 1), wherein the peptide is attached to the outer surface of said core particle, directly or through a linker or spacer. In some embodiments, at least one is a plurality.

According to other embodiments, the present invention provides a nanoparticle comprising a core particle and at least one peptide multimer of the invention, wherein the at least one peptide multimer is attached to the outer surface of said core particle. In some embodiments, at least one is a plurality.

According to further embodiments, the present invention provides a nanoparticle comprising a core particle and at least one peptide complex of the invention, wherein the at least one peptide complex is attached to the outer surface of said core particle.

According to some embodiments, the present invention provides a nanoparticle comprising a core particle and at least one peptide comprising the amino acid sequence LQIQSWSSSP (SEQ ID NO: 1), wherein the at least one peptide is attached to the outer surface of said core particle.

According to some embodiments, the core particle is selected from the group consisting of: liposomes, solid lipid nanoparticles, polymeric nanoparticles and metallic nanoparticles. According to some embodiments, the core particle is biodegradable.

Modification of nanoparticle surface with PEG can increase in vivo circulation time and decrease uptake by macrophages. Therefore, according to some embodiments, the nanoparticle is modified with PEG.

According to some embodiments, the core particle is a streptavidin-coated nanoparticle and the peptide, peptide multimer or complex comprises at least one biotin moiety, wherein the peptide, peptide multimer or complex is attached to the core particle through biotin-streptavidin interactions. According to specific embodiment, streptavidin-coated particle is a streptavidin-coated fluorescent nile red particle.

According to other embodiments, the core particle is a polymeric nanoparticle wherein the polymeric nanoparticle is selected from the group consisting but not limited to: polylactide-polyglycolide copolymers (PLGA), polylactide, polycaprolactones, polyacrylates, polyethylene glycol (PEG) and propylene glycol (PPG) nanoparticles and copolymers thereof.

PLGA particles offers several advantages for drug delivery platforms:
1. Biodegradability and biocompatibility.
2. FDA and European Medicine Agency approval in drug delivery systems for parenteral administration.
3. Well described formulations and methods of production adapted to various types of drugs e.g. hydrophilic or hydrophobic small molecules or macromolecules.
4. Protection of drug from degradation.
5. Possibility of sustained release-degradation time can vary from several months to several years, depending on the molecular weight and copolymer ratio.
6. Possibility to modify surface properties to provide stealthness and/or better interaction with biological materials
7. Possibility to target nanoparticles to specific organs or cells.

According to specific embodiments, the polymeric nanoparticle is a PLGA nanoparticle. According to particular embodiments, the PLGA is acid-terminated. According to further embodiments, the PLGA particle further comprises PEG. In some embodiments, the PLGA is PEG modified PLGA. In some embodiments, the PLGA particle further comprises Maleimide. In some embodiments, the particle is a PLGA-PEG-Maleimide particle. In some embodiments, the Maleimide is 30% Maleimide.

According to some embodiments, the core particle is a streptavidin-coated PLGA nanoparticle, and the at least one peptide or peptide multimer/complex comprises at least one biotin moiety, wherein the plurality of the at least one peptide or peptide multimer/complex are attached to the outer surface of said core particle through biotin-streptavidin interactions.

According to other embodiments, the core particle is a PLGA particle comprising acid-terminated PLGA, and the at least one peptide or peptide multimer/complex comprises at least one peptide sequence with a free amine group on the C-terminus, wherein the plurality of the at least one peptide or peptide multimer/complex are directly conjugated to the outer surface of said core particle through covalent amide bonds.

According to specific embodiments, the nanoparticle comprises a PEG-modified PLGA core particle and a plurality of tetramer peptides comprising four copies of a peptide comprising the sequence KFPDLDSRRLPHMSL (SEQ ID NO: 1), or a salt thereof, wherein said four peptide copies comprise a free amine groups on the C-terminus.

According to some embodiments, the nanoparticle is coated with a plurality of peptide conjugates. According to some embodiments, the nanoparticle is coated with a plurality of peptide conjugates having a structure according to Formula III. According to some embodiments, the nanoparticle comprises a PLGA core coated with a plurality of peptide conjugates. According to some embodiments, the nanoparticle comprises a PLGA core coated with a plurality of peptide conjugates having a structure according to Formula III.

According to particular embodiments, the nanoparticle further comprises a therapeutic or diagnostic agent. Each possibility represents a separate embodiment of the resent invention.

The therapeutic or diagnostic agent can be either encapsulated inside the nanoparticle (e.g., encapsulation in liposomes or polymeric nanoparticles) or attached to the particle surface non-covalently or covalently via a spacer or linker.

According to certain embodiments, the nanoparticle comprises PEG-modified PLGA core particle; at least one peptide of the invention and at least one Doa moiety; and a therapeutic agent; wherein the at least one peptide conjugate is attached to the outer surface of the core nanoparticle and wherein the therapeutic agent is encapsulated within the core particle. According to some embodiments, the at least one peptide conjugate has a structure according to Formula III.

According to some embodiment, the therapeutic agent is selected from the group consisting of TGFβ inhibitors and flavoenzyme inhibitors. According to some embodiment, the therapeutic agent is a TGFβ inhibitor. According to certain embodiments, the nanoparticle comprises PEG-modified PLGA core particle, at least one peptide or peptide tetramer or complex thereof comprising a sequence selected from SEQ ID NO: 1 to 13, and a TGFβ inhibitor, wherein the at least one peptide, peptide tetramer or complex thereof, is attached to the outer surface of the core nanoparticle and wherein the TGFβ inhibitor is encapsulated within the core particle. Any TGFβ inhibitor can be used, including but not limited to small molecules, peptides, polypeptides and antibodies. According to specific embodiments, the TGFβ inhibitor is SB431542.

According to some aspects, the present invention provides a composition comprising a peptide or peptide/multimer of the present invention. According to some embodiments, the present invention provides a composition comprising the nanoparticle in embodiments thereof as described hereinabove.

According to one embodiment, the composition is a pharmaceutical composition. According to some embodiments, the composition comprises a pharmaceutically acceptable carrier, excipient or adjuvant. Thus, in some embodiments, the present invention provides a pharmaceutical composition comprising a peptide or a peptide multimer/complex and a pharmaceutically acceptable excipient, wherein the peptide or a peptide multimer/complex comprises at least one amino acid sequence selected from the group consisting of SEQ ID NO: 1 to 13 or a salt thereof. In other embodiments, the present invention provides a pharmaceutical composition comprising a nanoparticle and a pharmaceutically acceptable excipient, wherein the nanoparticle comprises a core particle and a plurality of at least one peptide or peptide multimer/complex comprising at least one amino acid sequence selected from the group consisting of SEQ ID NO: 1 to 13 or a salt thereof. All definitions, terms and embodiments of previous aspects are explicitly encompassed by this aspect. In some embodiments, the group consisting of SEQ ID NO: 1 to 13 is the group consisting of SEQ ID NO: 1 to 8. It will be understood that when the composition is for use in treating a human the peptide will comprise a sequence selected from SEQ ID NO: 1 to 8.

According to particular embodiments, the pharmaceutical composition further comprises a therapeutic or diagnostic agent associated to said peptide or peptide multimer/complex. The term "agent associated" as used herein, refers to various types of binding or complexation forms, including but not limited to direct or non-direct (via a spacer or linker) covalent bonds, non-covalent bonds (such as biotin-avidin interaction), complexation with a carrier or a nanoparticle (e.g., coating, encapsulation) which is further linked, covalently or non-covalently, to the peptide or peptide multimer or complex.

According to some embodiments, the pharmaceutical composition comprises only a single peptide sequence selected from SEQ ID NO: 1 to 13 or a salt thereof. According to other embodiments, the pharmaceutical composition comprises at least two different peptide sequences selected from SEQ ID NO: 1 to 13 or a salt thereof.

Formulation of the pharmaceutical composition may be adjusted according to applications. In particular, the pharmaceutical composition may be formulated using a method known in the art so as to provide rapid, continuous or delayed release of the active ingredient after administration to mammals. For example, the formulation may be any one selected from among powders, syrups, liquids and solutions, aerosols, emulsions, suspensions, infusions, tablets, injections, spirits, capsules, and soft or hard gelatin capsules.

The term "pharmaceutically acceptable carrier" or "pharmaceutically acceptable excipient" or "pharmaceutically acceptable adjuvant" as used herein refers to any and all solvents, dispersion media, preservatives, antioxidants, coatings, isotonic and absorption delaying agents, surfactants, fillers, disintegrants, binders, diluents, lubricants, glidants, pH adjusting agents, buffering agents, enhancers, wetting agents, solubilizing agents, surfactants, antioxidants the like, that are compatible with pharmaceutical administration. Non-limiting examples of suitable excipients are water, saline, phosphate buffered saline (PBS), dextrose, glycerol, ethanol, or the like and combinations thereof. Other suitable carriers are well known to those skilled in the art. The use of such media and agents for pharmaceutically active substances is well known in the art.

The compositions may contain other active compounds providing supplemental, additional, or enhanced therapeutic functions. The peptides or peptide multimers/complexes of the present invention could be, according to some embodiments, suspended in a sterile saline solution for therapeutic uses. Numerous suitable drug delivery systems are known and include, e.g., implantable drug release systems, hydrogels, hydroxymethylcellulose, microcapsules, liposomes, microemulsions, microspheres, and the like. Controlled release preparations can be prepared through the use of polymers to complex or adsorb the molecule according to the present invention. For example, biocompatible polymers include matrices of poly(ethylene-co-vinyl acetate) and matrices of a polyanhydride copolymer of a stearic acid dimer and sebacic acid. The rate of release of the molecule according to the present invention from such a matrix depends upon the molecular weight of the molecule, the amount of the molecule within the matrix, and the size of dispersed particles.

The carrier may comprise, in total, from about 0.1% to about 99.99999% by weight of the pharmaceutical compositions presented herein.

According to another aspect, the present invention provides a method of treating a medical condition in which neutrophils are involved in the pathogenesis, the method comprising administering to a subject in need thereof the pharmaceutical composition of the present invention.

According to another aspect, there is provided a peptide, peptide multimer, peptide complex or composition of the invention for use in treating a medical condition in which neutrophils are involved in the pathogenesis.

In some embodiments, a medical condition is a disease. In some embodiments, a medical condition is a condition. In some embodiments, a medical condition is a disorder. In some embodiments, the medical condition is a neutrophil-associated disease or condition. In some embodiments, the medical condition is a disease or condition associated with accumulation of neutrophils. In some embodiments, the accumulation is at a diseased tissue or site. In some embodiments, the accumulation is at an injured tissue or site. In some embodiments, the medical condition is an inflammatory disease or condition. In some embodiments, the inflammatory disease or condition is an autoimmune inflammatory disease or condition.

In some embodiments, the medical condition is a disease in which the release of neutrophil extracellular nets (NETosis) is part of the pathophysiology. In some embodiments, the medical condition is a disease characterized by excessive neutrophil-mediated tissue damage. Non limiting examples of disease characterized by excessive neutrophil-mediated tissue damage are pulmonary diseases such as acute respiratory distress syndrome (ARDS) and chronic obstructive pulmonary disease (COPD). In some embodiments, the medical condition is ARDS. In some embodiments, the medical condition is COPD. In some embodiments, the disease is COPD. In some embodiments, the medical condition is selected from the group consisting of: a cancer, an inflammatory disease, condition or disorder, and an autoimmune disease, condition or disorder. According to some embodiments, the autoimmune disease, condition or disorder is an inflammatory autoimmune disease, condition or disorder. According to other embodiments, the medical disease is selected from the group consisting of thrombosis, Alzheimer disease, and a neutrophil-mediated skin disease. According to some embodiments, the medical condition is neutrophil-mediated skin disease. According to some embodiments, the medical condition is cancer. According to some embodiments, the medical condition is an inflammatory condition. According to some embodiments, the medical condition is an inflammatory disease. According to some embodiments, the inflammatory disease or condition is selected from chronic obstructive pulmonary disease (COPD), inflammatory bowel disease (IBD) and peritonitis. According to some embodiments, the inflammatory disease or condition is COPD. According to some embodiments, the inflammatory disease or condition is IBD. According to some embodiments, the inflammatory disease or condition is peritonitis. In some embodiments, IBD comprise colitis and Chron's disease. In some embodiments, IBD is colitis. In some embodiments, colitis is ulcerative colitis.

According to some aspects and embodiments, the present invention provides a method of treating a medical condition selected from the group consisting of cancer, inflammatory disease or disorder and autoimmune disease or disorder, the method comprising administering to a subject in need thereof the pharmaceutical composition of the present invention.

According to some embodiments, the cancer is selected from solid tumor cancer and hematological cancer. Each possibility represents a separate embodiment of the present invention. According to some embodiments, the solid cancer is selected from the group consisting of breast cancer, lung cancer, colon cancer, pancreatic cancer, liver cancer, head and neck cancer and kidney cancer. According to some embodiments the hematological cancer is leukemia. Each possibility represents a separate embodiment of the present invention.

According to some embodiments, the inflammatory disease is a disease in which neutrophils are involved in the pathogenesis. According to some embodiments, the inflammatory disease or disorder is selected from the group consisting of peritonitis, colitis, vasculitis, atherosclerosis, chronic obstructive pulmonary disease (COPD), acute respiratory distress syndrome (ARDS), bronchiectasis, neutrophilic asthma, rheumatoid arthritis (RA), lupus, cystic fibrosis (CF), sepsis, multiple sclerosis, psoriasis and traumatic injury. Each possibility represents a separate embodiment of the present invention. According to some embodiments, the disease or disorder is Systemic Lupus Erythrocytes (SLE). According to some embodiments, the disease or disorder is rheumatoid arthritis (RA).

The pharmaceutical composition of the present invention may be administered by any know method. The terms "administering" or "administration of" a substance, a compound or an agent to a subject can be carried out using one of a variety of methods known to those skilled in the art. For example, a compound or an agent can be administered, intravenously, arterially, intradermally, intramuscularly, intraperitonealy, intravenously, subcutaneously, ocularly, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods. In some embodiments, the administration includes both direct administration, including self-administration, and indirect administration, including the act of prescribing a drug. For example, as used herein, a physician who instructs a patient to self-administer a drug, or to have the drug administered by another and/or who provides a patient with a prescription for a drug is administering the drug to the patient.

According to some embodiments, the pharmaceutical composition is administered by an invasive mode of administration such as intramuscularly, intravenously, intra-arterially, intraarticularly or parenterally. According to specific embodiments, the pharmaceutical composition is administered intravenously. According to some embodiments, the composition is administered systemically. According to some embodiments, the composition is administered to a site of inflammation. According to some embodiments, the composition is formulated for systemic administration. According to some embodiments, the composition is formulated for administration to a site of inflammation.

It will be apparent to those of ordinary skill in the art that the therapeutically effective amount of the molecule according to the present invention will depend, inter alia upon the administration schedule, the unit dose of molecule administered, whether the molecule is administered in combination with other therapeutic agents, the immune status and health of the patient, the therapeutic activity of the molecule administered and the judgment of the treating physician. As used herein, a "therapeutically effective amount" refers to the amount of a molecule required to alleviate one or more symptoms associated with a disorder being treated over a period of time.

Although an appropriate dosage of a molecule of the invention varies depending on the administration route, type of molecule (polypeptide, polynucleotide, organic molecule etc.) age, body weight, sex, or conditions of the patient, it will be determined by the physician in the end. Various considerations in arriving at an effective amount are described, e.g., in Goodman and Gilman's: The Pharmacological Bases of Therapeutics, 8th ed., Pergamon Press, 1990; and Remington's Pharmaceutical Sciences, 17th ed., Mack Publishing Co., Easton, Pa., 1990.

According to some embodiments, the present invention provides a diagnostic or research composition comprising the peptide or peptide multimer/complex of the invention. According to further embodiments, the present invention provides a diagnostic or research composition comprising a nanoparticle comprising the peptide or peptide multimer/complex of the invention. According to specific embodiments, the peptide or peptide multimer/complex comprises the amino acid sequence LQIQSWSSSP (SEQ ID NO: 9) or a salt thereof.

The terms "comprising", "comprise(s)" "include(s)," "having," "has," "contain(s)," as used in this specification means "consisting at least in part of". When interpreting each statement in this specification that includes the term "comprising", features other than that or those prefaced by the term may also be present. Related terms such as "comprise" and "comprises" are to be interpreted in the same manner. The terms "have", "has", having" and "comprising" may also encompass the meaning of "consisting" and "consisting essentially of", and may be substituted by these terms. The term "consisting of" excludes any component, step or procedure not specifically delineated or listed. The term "consisting essentially of" means that the composition or component may include additional ingredients, but only if the additional ingredients do not materially alter the basic and novel characteristics of the claimed compositions or methods.

As used herein, the term "about", when referring to a measurable value such as an amount, a temporal duration, and the like, is meant to encompass variations of +/−10%, or +/−5%, +/−1%, or even +/−0.1% from the specified value.

Although the present invention has been described with respect to various specific embodiments thereof in order to illustrate it, such specifically disclosed embodiments should not be considered limiting. Many other specific embodiments will occur to those skilled in the art based upon applicants' disclosure herein, and applicants propose to be bound only by the spirit and scope of their invention as defined in the appended claims.

EXAMPLES

Materials and Methods

Cell lines: Mouse mammary tumor breast cancer cells 4T1, expressing luciferase introduced by lentiviral infection, and AB12 lung cancer cells were used.

Animal experiments: Animal experiments were performed according to the approval of the animal use protocol by the Hebrew University of Jerusalem animal ethics committee.

Healthy animals: Blood was harvested from healthy Balb/C mice through cardiac puncture. White blood cells (WBCs) were purified by subjecting 25 µl of whole blood to RBC lysis. RBC lysis was performed with water for 30 sec and stopped by adding 2.5% BSA/5×PBS. WBC were then diluted in 0.5% BSA/1×PBS and total number of cells was counted.

Tumor-bearing mice: Following anesthesia, female mice were injected to the mammary fat pad with $1\times10^6$ 4T1 tumor cells. Breast tumors were allowed to reach an average size of 700-800 mm$^3$ (15-21 days). Blood was harvested through cardiac puncture. Blood was diluted with 0.5% BSA/1×PBS to 6 ml and overlaid on a sucrose gradient (3 ml Histopaque 1119, 3 ml Histopaque 1077). In order to obtain a pure neutrophil population, cells were harvested from the interface layer between 1.119 and 1.077 g/ml Histopaque (around the 3 ml mark). RBC lysis was performed with water for 30 sec and stopped by adding 2.5% BSA/5×PBS. When needed, tumors were harvested from the mice, minced, and digested in L15 medium containing 0.2 mg/ml collagenase type I, 0.1 mg/ml collagenase type II, 0.2 mg/ml collagenase type IV, 25 µg/ml Elastase and 25 µg/ml DNase I at 37° C. for 1 hr. After RBC lysis, remaining cells were coated with APC-labeled Ly6G-specific antibodies, and purified using Easy-sep columns following manufacturer's instructions.

Serum preparation: Blood was extracted from one healthy Balb/C mouse by cardiac puncture and was transferred into a 1.7 mL tube. Blood was left at RT for 1 h to allow blood clotting. The sample was centrifuged for 10 min at 1,500 g at 4° C. From −850 µl of blood, 380 µl of serum could be obtained.

Acute Inflammation Models in Mice

Peritonitis model: peritonitis was induced in Balb/C mice by intraperitoneal (i.p.) injection of 1 ml zymosan/PBS (1 mg/ml). 4 hours after induction, 200 µl of peptide- or uncoated-nanosphere solution was injected via the tail vein. 200 µl of nanospheres equals approximately $4.7\times10^{11}$ spheres per mouse. After 2 hours, mice were sacrificed and blood and peritoneal lavage were harvested and examined for presence of sphere-positive neutrophils.

For WBC analysis, 25 µl of whole blood were subjected to RBC lysis. Peritoneal cells were isolated by peritoneal lavage, i.e. injection of 5 ml PBS into the peritoneum, gentle massage and collection of cells with a 25G needle on a 5 ml syringe. WBC and $0.5\times10^6$ peritoneal cells were stained with CD45-APC and Ly6G-Vio antibodies and after wash analyzed by flow cytometry.

Colitis model: colitis was induced in healthy Balb/C mice by adding 4% DSS to the drinking water for 5 consecutive days. Drinking water was then changed to tap water until the end of the experiment. Control mice were given tap water for all the duration of the experiment. Since it was founded in calibration experiments that the peak of inflammation and neutrophil infiltration is on day 7, 200 µl of peptide- or uncoated-nanosphere solution (200 µl of nanospheres equals approximately $4.7\times10^{11}$ spheres) were injected on day 7, waited 2, 5 or 24 hours and isolated blood and organs for single cell FACS analysis and sectioning for histology. Proximal colons were minced, and digested in L15 medium containing 0.2 mg/ml collagenase type I, 0.1 mg/ml collagenase type II, 0.2 mg/ml collagenase type IV, 25 µg/ml Elastase and 25 µg/ml DNase I at 37° C. for 30 min with shaking. The cell suspension was filtered through 45 µm cell strainer. $1\times10^6$ cells were stained with CD45 and Ly6G antibody for 30 min at 4° C. After washing, cells were analyzed by flow cytometry. Typhoon laser scanner was used to visualize distribution of fluorescence within organs.

Human blood samples: Human experiments were done based on Hadassah's Helsinki approval.

Following blood withdrawal, blood was overlaid on 3% dextran in 0.9% NaCl in a 1:1 ratio and left at RT for 25 min to allow erythrocyte sedimentation. Residual RBCs were lysed by adding water for 30 sec and stopped by adding 2.5% BSA/5×PBS. WBCs were then diluted in 0.5% BSA/1×PBS and total number of cells was counted. Purification of pure neutrophils (HDNs) was done by overlaying blood after RBC sedimentation in a 1:1 ratio on Histopaque-1077. After 30 min centrifugation at 400 g, pure neutrophils were found at the bottom of the tube (pellet). Mononuclear cells (LDF—low density fraction) settle between the Histopaque-1077 and the 0.9% saline.

Flow cytometric analysis: All samples were filtered through cell strainer caps (35 µm) of BD tubes before analyzed by FACS. Cells were studied by FACS analysis using a BD LSR Fortessa flow cytometer. Data analysis is done using FlowJo X software (Ashland, OR).

Phage display screening on human neutrophils: The phage library compromised a mix of 8 libraries, including 6-, 8-, 10- and 12-mers in a cysteine looped and unlooped form. The library stock had a concentration of $1\times10^{12}$ pfu/ml and was diluted 1:10 in 0.5% BSA/1×PBS. 200 µl were incubated with $2\times10^7$ purified HDNs for 20 min at RT while shaking. Following elution of the phages bound to the neutrophils, the eluate was amplified on DH5α+*E. coli*. The amplified phages were used for a round of negative selection: the amplificate was diluted 1:10 in 0.5% BSA/1× PBS and 200 µl were applied first on isolated cells of the low density fraction (LDF) of healthy donors. Low density cells ($1\times10^7$) from healthy donors contain only lymphocytes and monocytes. The LDF cells were incubated with the amplificate for 20 min at RT under agitation. After spin down (300 g, 10 min) the supernatant was applied to HDNs as described for the first selection round. From here on, amplification and selection steps repeat. The eluate of the third selection round was subjected to PCR. Using primers that flank the insertion site of pVIII, a PCR product including a big variety of sequences coding for different peptides can be obtained. After quality control on an agarose gel and purification, the PCR product was sequenced by MiSeq (Core Research Facility Unit Hadassah Ein Kerem). The obtained sequences were subjected to bioinformatics and motif analysis.

Phage titration—Plaque Assay: DH5αF+ bacteria are grown in 2 ml LB medium overnight. 200 µl of bacterial culture are added to 0.5% agarose and poured onto a pre-warmed LB agar plate. When the agarose is solid, a ten-fold serial dilution of phage solution is applied. The dilution that allows identifying single plaques is used to count back to the titer of phages in the stock solution.

Synthetic peptides: Peptides were purchased or synthesized using solid phase peptide synthesis.

Sequence of mouse peptide-construct: (LQIQSWSSSP (SEQ ID NO: 9) Doa-Doa-C)4-(Mpa)-4-Lys2-Lys-beta-Ala-Lys(Biotin)-beta-Ala-OH (SEQ ID NO: 16). The LQI tetramer peptide is resuspended in ultra-pure water and adjusted to a concentration of 309 µM. Due to the presence of the amino acid tryptophan within the peptide sequence, the LQI tetramer peptide can be quantified measuring its absorbance at a wave length of 280 nm with the nanodrop (MW 7.6 kDa, extinction coefficient ε=22760 M−1 cm−1.

To allow formation of LQI-tetramer-SA complex, 1 µL of the 309 µM stock solution of the tetrameric peptide was preincubated with 300 µL of 3.3 µg/mL SA-Cy3 for 30 min at RT. Sequence of human peptide-construct: (KFPDLDSRRLPHMSL (SEQ ID NO: 1) Doa-Doa-C)4-(Mpa)-4-Lys2-Lys-beta-Ala-Lys(Biotin)-beta-Ala-OH (SEQ ID NO: 16).

Resazurin Viability Assay: 4T1 breast cancer cells were plated in 10% FCS/DMEM in a 96-well plate at a density of 50,000 cells per well. Cells were allowed to attach for 4 hours before treatment with the LQI tetramer peptide in different concentrations. 18 hours later, resazurin solution was added in an amount that equaled 10% of the culture medium volume. 2 hours later, fluorescence was measured which determines the cell number (viability) as a function of metabolic activity using the conversion of resazurin dye.

FITC Annexin V and PI staining: $1\times10^6$ of purified HDN from 4T1 tumor bearing mice were incubated with the different concentrations of LQI tetramer peptide for 30 min at 37° C. in 100 uL of 10% FCS/RPMI and stained with FITC Annexin V according to manufacturer's instruction (Invitrogen). 0.5 µl of PI 1 mg/ml were added to 300 µl of stained cell suspension 30 sec before flow cytometry analysis.

ROS production: 180 µl containing $2\times10^5$ purified HDN in Hank's balanced salt solution without phenol red (HBSS) were placed in each well of a white 96-flat-bottom well plate. 20 µl of a 500 µM luminol solution in PBS were added to each well. Using the plate reader, basal chemiluminescence was determined for 1000 msec in a time course of 5 minutes with 10 sec intervals. Then, cells were treated with various amounts of the LQI tetramer peptide or 10 nM PMA. Immediately after treatment, chemiluminescence was read in the plate reader (InfiniteF200Pro, TECAN) for a time course of 35 min.

Transwell migration assay: HDNs were isolated by density-gradient centrifugation from the circulation of 4T1 tumor-bearing mice, purity >95%. 800 µl of 2% FCS/RPMI medium were placed into the 24-well plate, then Millicell® cell culture inserts with a pore size of 5 µM were placed into the wells and allowed to soak for 5 min. HDNs were suspended to a density of 250,000 cells/ml in 2% FCS/RPMI and 200 µl of the cell suspension were placed into the upper chamber of the transwell insert. Migration was stimulated by addition of 100 ng/µl CXCL2 to the bottom chamber of the wells (consider V=800 µl), and peptide was added to HDN in the upper chamber in two different concentrations (3.09 µM or 309 nM considering V=200 l). Assay was stopped after 1.5 hr and inserts were removed with a forceps. Each condition was tested in triplicate. 5 pictures were taken per well at the same coordinates (middle, top, bottom, left, right). Cells per field of view were counted using ImageJ.

In vitro luciferase assay to monitor the anti-tumor activity of isolated neutrophils ('Killing Assay'): 5,000 luciferase-labeled 4T1 breast carcinoma cells were seeded in 100 µl OptiMem medium containing 2% heat-inactivated FCS in each well of a white 96-flat-bottom well plate. 24 hours after seeding the tumor cells, $1\times10^5$ HDNs purified from the circulation of 4T1-tumor-bearing mice were added in 50 µl OptiMem with 2% FCS. The co-culture was incubated overnight. Control wells were incubated in 50 µl medium without neutrophils. Multiple repeats (12 wells) were done of each experimental setting. The supernatant was aspirated and 50 µl of cell culture lysis buffer were added (Promega). The plate was incubated for 15 min on an orbital shaker and then read in the plate-reader. Well-wise 50 µl of in-house prepared luciferase assay solution was injected during the measurement, and chemiluminescence was read for 10 sec per well. % tumor lysis was calculated by the following formula: % tumor lysis=(1−[luminescence of samples with neutrophils]/[luminescence of samples in medium])×100%.

Detection Assay for LQI tetramer peptide: Two assays were used to detect LQI tetramer peptide binding:

"Tetramer alone": The LQI tetramer peptide was incubated with $0.5\times10^6$ HDN in 50 µl for 30 min at 4 C. After washing, the cells were stained with 50 µl 3.3 µg/ml of Streptavidin-Cy3 (SA-Cy3).

"Tetramer-Streptavidin Complex":1 µl of the 309 µM stock solution of the tetrameric peptide was preincubated with 300 µl of 3.3 µg/ml SA-Cy3 for 30 min at RT. 100 µl of LQI tetramer-SA-Cy3 mix was then used to stain $0.5\times10^6$ cells.

Washes and dilutions of the LQI tetramer peptide and SA-Cy3 were done in 0.5% BSA/1×PBS buffer.

Native Polyacrylamide Gel & Silver Stain: Native polyacrylamide gel was prepared with a 4% stacking gel and 12.5% separating gel. No SDS or β-mercaptoethanol was used, and the samples were not heated in order to maintain the binding between the LQI tetramer peptide and SA-Cy3.

10 µl of the samples were mixed with 10 µl of 2× loading buffer (30% glycerol, 62.5 mM Tris 6.8, bromphenolblue). Gel was run 3 hours at 200 V. SA-Cy3 in gel was imaged with BioRad ChemiDoc MP Imaging System and Image Lab 4.1 Software. Gel was stained with Pierce Silver Stain Kit according to manufacturer's instructions.

TABLE 1

| Gel composition | | |
|---|---|---|
| Ingredient | Stacking Gel 4% | Separation Gel 12.5% |
| DDW | 3.8 ml | 4.3 ml |
| 1.0M Tris pH 6.8 | 625 µl | — |

TABLE 1-continued

| Gel composition | | |
|---|---|---|
| Ingredient | Stacking Gel 4% | Separation Gel 12.5% |
| 1.5M Tris pH 8.5 | — | 2.5 ml |
| 40% Acrylamide/0.25% Bis | 525 µl | 3.1 ml |
| 10% APS | 40 µl | 100 µl |
| TEMED | 7 µl | 5 µl |

Nanosphere coating and i.v. injection: Streptavidin Coated Fluorescent Nile Red Particles (0.7-0.9 µM) were purchased from Spherotech, Inc., IL, US. 200 µl of spheres were resuspended in 400 µl of PBS and 5 µl of 309 µM LQI tetramer peptide solution was added. After 1× wash with PBS, spheres were resuspended in 200 µl PBS and injected via the tail vein.

Generation of SA-Coated PLGA Particles

Activation fatty acid: 10 mg of stearic acid were dissolved in 10 ml of 0.1×PBS/2% deoxycholate buffer and a 1:10 dilution in the same buffer was prepared. 3.45 mg of NHS (=30 µmol) and 2.33 mg of EDC(=15 µmol) were added to 10 ml of 100 µg/ml stearic acid (=3.52 µmol). The fatty acid activation mix was incubated for 1 hr at RT.

Conjugation of fatty acid and SA: 2.5 mg of SA (=41.5 nmol) were dissolved in 2.5 ml of activated fatty acid solution (~900 nmol) and the mix was incubated for 2 h at 37° C. with inversion every 20 min. The conjugate solution was transferred to a dialysis tube (GeBaFlex tube, cutoff 3.5 kDa) and dialyzed against 4.5 liter of 1×PBS overnight at 4° C. while stirring.

PLGA particle generation: 85 mg of PLGA (~45 kDa), 5 mg of PLGA-Cy5 and 2 mg of SB-431542 purchased from Axon Medchem were dissolved in a total volume of 3 ml chloroform. 2.5 ml of SA-lipid conjugate were added to 23 ml of 2% PVA/PBS in a 50 ml tube and solution was saturated with 5-6 drops of chloroform. A tip sonicator was placed into the 50 ml tube and the chloroform solution containing the PLGA, PLGA-Cy5 and SB-431542 was added dropwise to the PVA solution while sonication for 90 sec. The emulsion was placed in a small beaker and stirred overnight under a chemical hood to evaporate chloroform. NP formulation was washed twice with 45 ml 1×PBS (20,000 rpm for 20 min 4° C.) and then resuspended in 2 ml of 2% mannitol/H2O. Suspension was frozen in −20° C. ethanol bath and lyophilized for 48 h.

Preparation of SB-431542 PLGA nanoparticles (NPs): SB-431542, a known TGFβ blocker (Laping NJ, et al. Molecular pharmacology, 2002, 62(1), 58-64) was encapsulated into PLGA nanoparticles using an oil/water single emulsion technique. Briefly, 2 mg of SB-431542 and 90 mg pf PLGA (50:50 lactide:glycolide ratio, acid terminated, ~45 kDa) were dissolved in 3 ml of chloroform. The solution was then added drop-wise to 2% polyvinyl alcohol (PVA) solution (25 ml), and was sonicated over an ice bath (using a tip sonicator) for 1 min to form an oil/water emulsion. The emulsion was stirred overnight at room temperature (in the hood) to remove the chloroform, resulting in NPs formation. NPs were washed with PBS (using ultracentrifuge) to remove PVA and un-entrapped SB-431542, and kept at 4° C. until use. Drug-free NPs (Empty NPs) were prepared by the same procedure, omitting the drug.

Preparation of PEG-modified SB-431542 containing PLGA NPs: The small molecule TGFβ inhibitor SB-431542 was encapsulated into PLGA nanoparticles using an oil/water single emulsion technique. Briefly, 72 mg of PLGA (60%), 36 mg of PLGA-PEG-Maleimide (30%) and 12 mg of PLGA-Cy5 (10%) were dissolved in 3 ml of chloroform. Then, 3 mg of SB-431542 were dissolved in 200 µl DMSO and added to the PLGA mixture. The PLGA-SB-431542 solution was added drop-wise to 2% polyvinyl alcohol (PVA) solution (25 ml), and sonicated over an ice bath (using a tip sonicator) for 90 sec to form an oil/water emulsion. The emulsion was stirred overnight at room temperature (in the hood) to remove the chloroform, resulting in NPs formation. NPs were washed with PBS (using ultracentrifuge) to remove PVA and un-entrapped SB-431542. Drug-free NPs (Empty NPs) were prepared by the same procedure, omitting the drug.

Coupling of human-binding peptide to PEG-modified SB-431542 containing PLGA NPs: 4 mg of KFP-SH tetramer (see structure below) are resuspended in 2 ml of degassed sodium-acetate buffer with 10 mM EDTA and resuspended for 20 min at RT. 2 ml of peptide are added to 10 ml nanoparticles resuspended in PBS followed by incubation of 5 hours at RT and then overnight at 4° C. 12 ml of NP solution are transferred to dialysis tubes with 300,000 Da cut-off followed by spinning 3×20 min at 3000 g. After each 20 min, NPs are resuspended. NP are collected and washed twice with 50 ml PBS using ultracentrifugation. Finally, NP are resuspended in 2 ml of 2% mannitol and freeze-dried.

KFP-SH tetramer structure:

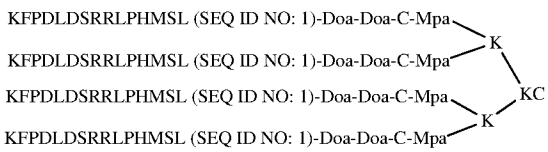

NP characterization: NPs are characterized by dynamic light scattering (Malvern Zetasizer), transmission electron and scanning electron microscopy (TEM & SEM). In order to quantify drug loading, 1 mg of nanoparticles is dissolved in 50 µl of DMSO which disintegrates the nanoparticles and release SB-431542. The absorption of the solution is measured at 325 nm. Based on a standard curve, the concentration of SB-431542 is determined. Drug loading is then calculated using the following formula:

$$\text{Drug Loading (\%)} = \frac{\text{weight of drug in nanoparticles}}{\text{weight of nanoparticles}} \times 100$$

Using the calculated drug loading, the encapsulation efficiency is calculated.

$$\text{Encapsulation Efficiency (\%)} = \frac{\text{weight of drug in nanoparticles}}{\text{weight of drug initially fed}} \times 100$$

The yield of nanoparticles is calculated using the following formula:

$$\text{Nanoparticle yield (\%)} = \frac{\text{weight of nanoparticles}}{\text{weight of polymer} + \text{drug} + \text{weight of mannitol}} \times 100$$

Peptide coupling was quantified using BCA assay. After peptide coupling and several wash steps, 1 mg of particles from batches with and without peptide linkage, were subjected to BCA assay. The determined amount of peptide linked to nanoparticles, as well as the initial amount used (4 mg) are used as input in the following formula:

TABLE 2

Material Specifications $$\text{Linkage Efficiency (\%)} = \frac{\text{weight of peptide in nanoparticles}}{\text{weight of peptide initially used}} \times 100$$

| Material | MW | LA:GA, Description | Specification/ Company |
|---|---|---|---|
| PLGA | 38,000-54,000 Da | 50:50, acid terminated | Resomer ® RG 504 H Sigma/ Evonik |
| PLGA-PEG-Mal | PLGA 30,000 PEG 5,000 Da | 50:50 | AI110 PolySciTech |
| PLGA-Cy5 | 45,000-55,000 Da | 50:50 | AV034 PolySciTech |
| KFP-SH Tetramer | | KFPDLDSRRLPHMSL (SEQ ID NO: 1), Custom Made | Intavis AG |

Example 1

Identification and Optimization of a Peptide Binding to Murine Neutrophils

Figure 11:
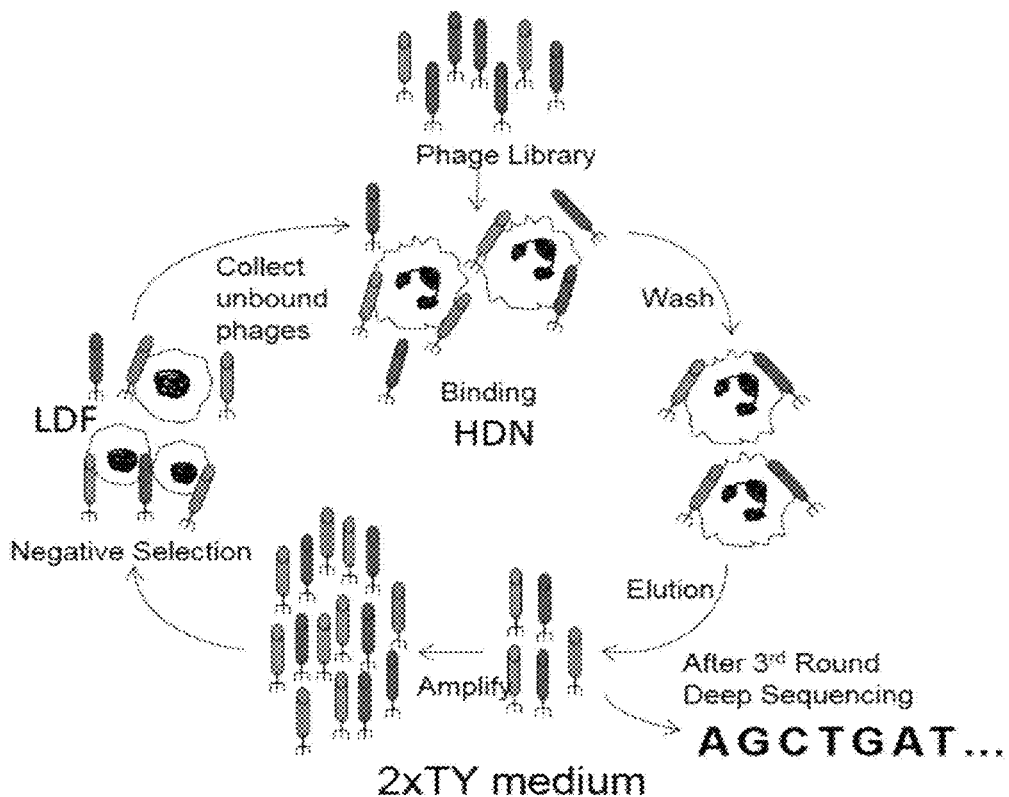
FIG. 11: A schematic representation of Phage library screening, alternating rounds of positive selection (to HDN) and negative selection (to mononuclear low-density fraction, LDF).

A phage-display screening of a peptide library was conducted, in a similar way to a screen conducted by Mazzucchelli et al. (Blood, 1999, 93(5), 1738-1748). In the present screen, a library of pages displaying $10^{12}$ different peptides on their VIII protein was used to identify peptides that bind to murine neutrophils. The peptides in the library were random sequences of 6-12 amino acids in linear or cyclic form (Ryvkin et al., 2018, Nucleic Acids Research, 2018, Vol. 46, No. 9 e52). The screen was conducted using murine Normal-Density Neutrophils (NDN) for positive selection, whereas monocytes and lymphocytes served for negative selection. Following 3 rounds of positive panning and 2 interlaced rounds of negative panning, the neutrophil affinity selected phages were eluted and sequenced (FIG. 11). The top-ranking enriched peptide sequences and their prevalence in the final eluate (average of 5 replicates) are presented in Table 3.

TABLE 3

Sequences of peptides binding to murine neutrophils.

| Rank | Sequence | Prevalence (%) |
|---|---|---|
| 1 | LQIQSWSSSP (SEQ ID NO: 9) | 28.4 |
| 2 | STMTILGTGS (SEQ ID NO: 10) | 10.4 |
| 3 | TETSLRIVSTNP (SEQ ID NO: 11) | 4.1 |
| 4 | LSIVSGSALNHL (SEQ ID NO: 12) | 2.9 |
| 5 | LTLVSERPMI (SEQ ID NO: 13) | 1.5 |

Figure 1B:
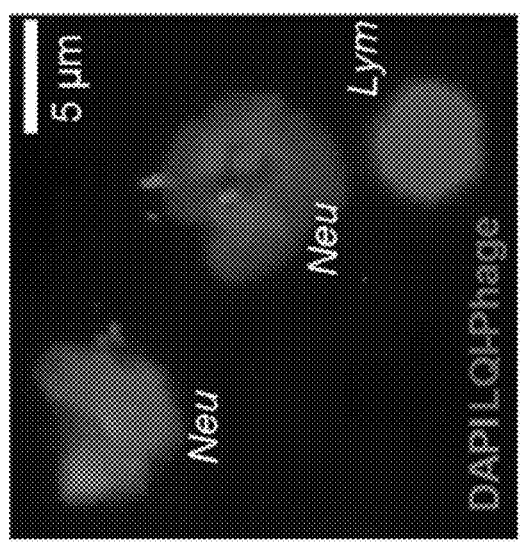

The peptide having the best binding obtained in the screening was the peptide LQI, consisting of the amino acid sequence LQIQSWSSSP (SEQ ID NO: 9). The phage presenting this peptide showed the highest specificity, binding to 95% of neutrophils, with no detectable binding to monocytes or lymphocytes (FIG. 1A-B).

Figure 1C:

Several LQI monomeric peptide conjugates were synthesized by tagging the N-terminus of LQI peptide with Cy5, biotin or fluorescein (FIG. 1C). Competition assays were then performed in order to evaluate the binding of LQI and its conjugates to murine neutrophils. For the competition assays, $1 \times 10^6$ density-gradient purified HDNs from 4T1 tumor bearing Balb/C mice were incubated first with each of the synthetic peptides for 20 min, and later incubated with $10^{10}$ phages presenting the LQI peptide on their surface. Phage binding was detected by flow cytometry with a M13-PE antibody.

Figure 1D:
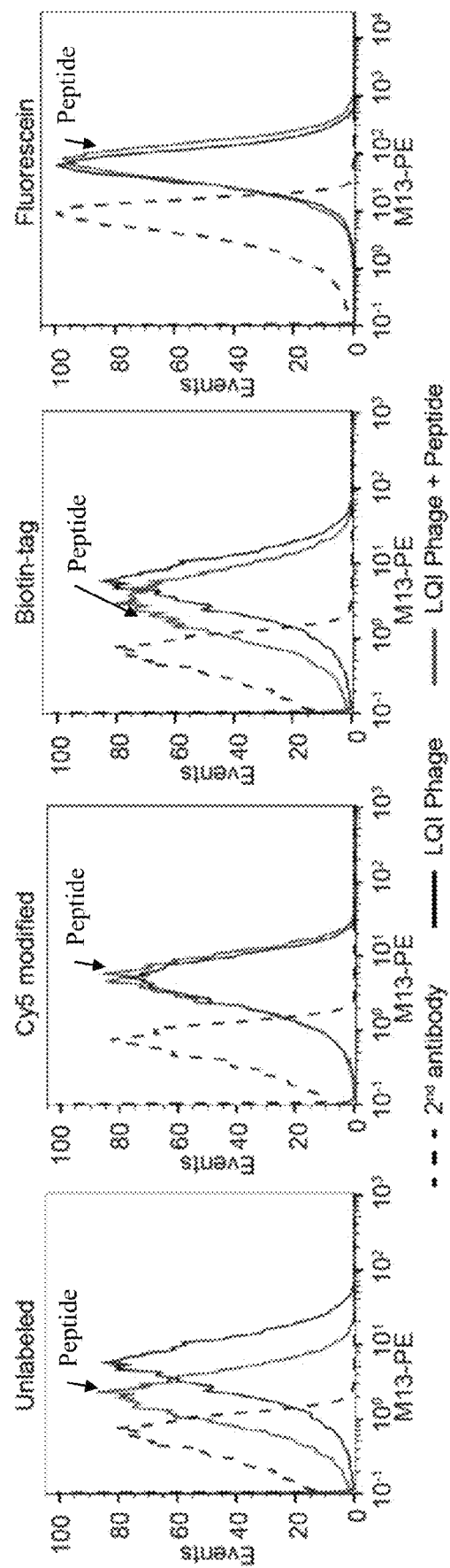

As can be seen in FIG. 1D, while the naked synthetic peptide was able to compete with the phage binding to neutrophils, binding was not detected for the peptide conjugates. These results indicate that the N-terminus of the peptide is likely involved in the binding to neutrophils.

Figure 2A:
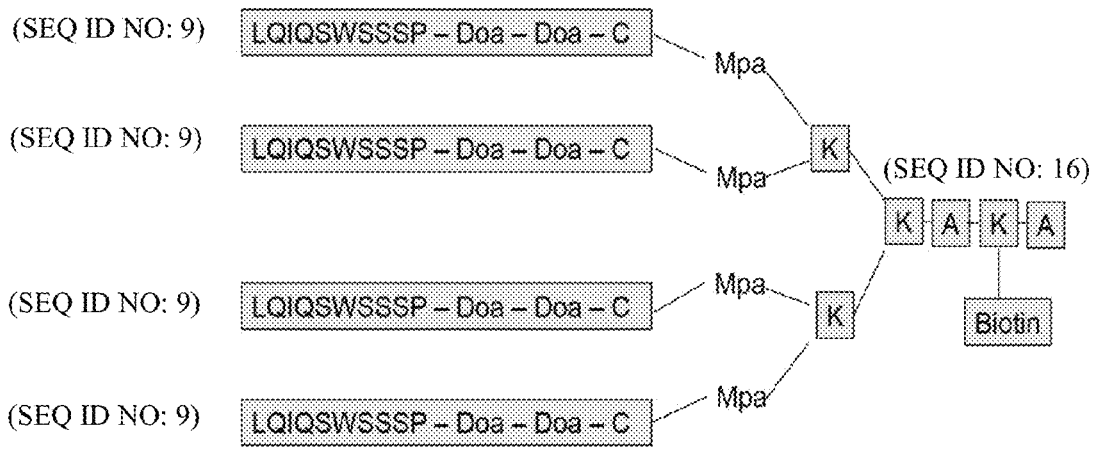
FIGS. 2A-I: (2A) Schematic representation of the structure of a tetrameric LQI. (2B) FACS analysis comparing the binding of LQI tetramer (left) and 16-LQI (right) to WBC. (2C) Quantification of LQI tetramer or 16-LQI binding to neutrophils and other WBC. (2D) Titration of neutrophil binding comparing the LQI tetramer to 16-LQI and to 16-control peptide. (2E) Representative histogram showing the percent binding of 16-LQI to each WBC population in healthy Balb/C mice following ex vivo incubation and staining with Streptavidin-Cy3, as analyzed by flow cytometry. *=gating based on light scatter. (2F) Representative histograms showing LQI tetramer binding to high density neutrophils (HDNs) of Balb/C mice bearing 4T1-breast cancer derived tumor, as analyzed by flow cytometry. Ly6G$^+$ population represent HDN and Ly6G− cells are other WBCs. (2G) Representative histogram showing LQI tetramer peptide binding to TANs isolated from 4T1 tumors, as analyzed by flow cytometry. (2H) Bar graph showing a summary of binding efficiency of LQI tetramer peptide, control peptide or SA-Cy3 only to various types of neutrophils, as analyzed by flow cytometry. (2I) Representative image of confocal microscopy with Gr-1 neutrophils (green) bound by the 16-LQI (red).
Figure 2B:
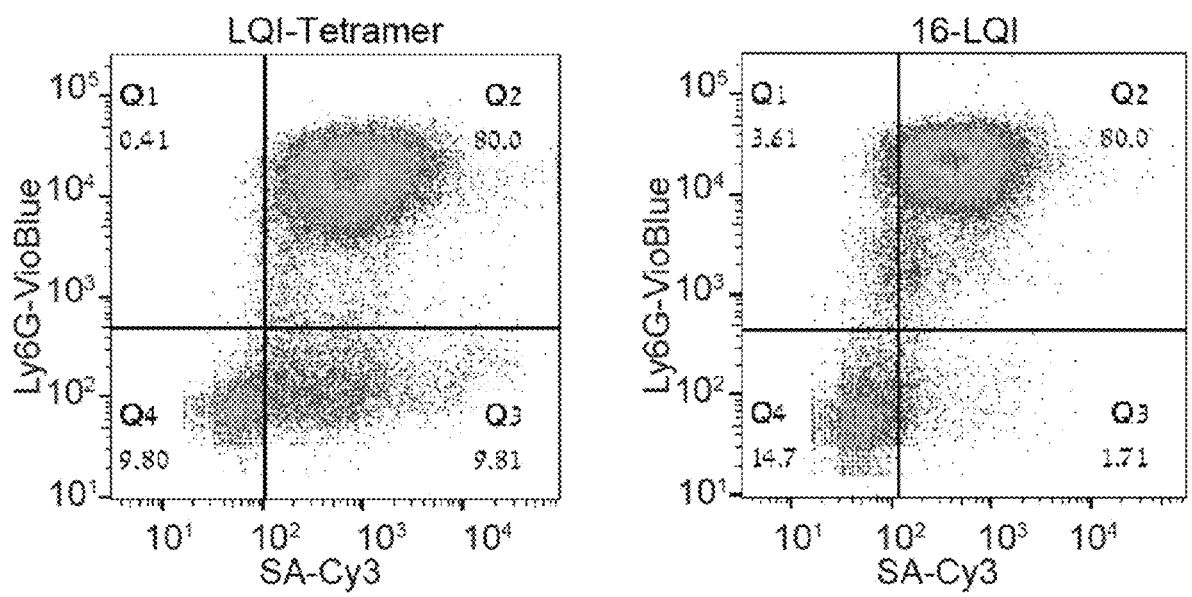

Next, a tetrameric peptide was designed comprising 4 copies of the peptide LQI (having a free N-terminus) on a branched tetrameric core based on Li et al. (Molecular cancer therapeutics, 2009, 8(5), 1239-1249). Each branch of the tetrameric peptide comprises 8-amino-3,6-dioxaoctanoic acid (Doa) to increase solubility, maleimidopropionic acid (Mpa) as a linker, and is connected via lysine linkers to a biotin-tag which makes the complex accessible for fluorescent detection and manipulation. The structure of the tetrameric peptide is provided in FIG. 2A. The binding affinity of this tetrameric peptide to murine neutrophils was assessed by a competition assay as described above for LQI monomer constructs. The LQI-tetramer efficiently binds ~100% of neutrophils (a slight improvement over the LQI monomer), however, it concomitantly binds ~50% of other white blood cells (WBCs) (FIG. 2B, left and 2C).

Example 2

Figure 3:
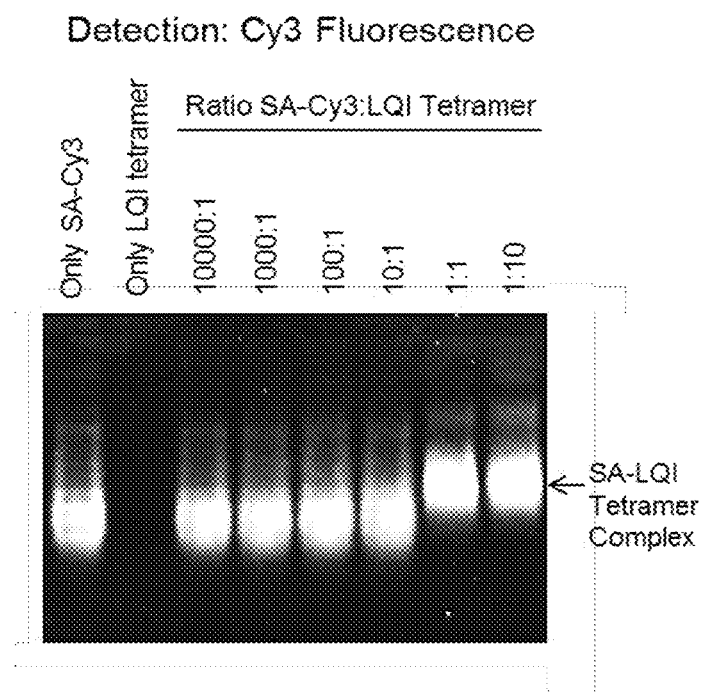
FIG. 3: Micrograph of polyacrylamide gel electrophoresis (PAGE) of Streptavidin-Cy3 (SA-Cy™3) only, LQI tetramer only, and samples of SA-Cy3+LQI tetramer peptide in various SA-Cy3:tetramer ratios.

LQI Tetramer-Streptavidin (SA) Complex Shows Higher Specificity to Murine Neutrophils LQI tetramer was incubated with fluorescently-tagged SA which has four binding sites for biotin. Thus, the LQI tetramer-SA complex is a 16-mer of the LQI-peptide (16-LQI). 2.7 µg of SA-Cy3 were incubated with different amounts of LQI tetramer peptide for 20 min at room temperature (RT) to allow complex formation. Samples were then loaded on a 12.5% native polyacrylamide gel (PAGE) and run for 3 hours at 200 V. SA-Cy3 fluorescence was detected using a fluorescent imager. As can be seen in FIG. 3, a shift in the molecular weight of SA was observed, confirming complex formation.

To examine the binding of 16-LQI to murine neutrophils, 10 µl of LQI tetramer alone or 16-LQI was incubated with $0.5 \times 10^6$ WBCs from 4T1-tumor bearing mice for 30 min at 4° C. The cells were washed and analyzed by flow cytometry. For LQI tetramer alone assay, cells were first incubated with the LQI tetramer peptide, washed and then stained with SA-Cy3. The 16-LQI showed 100% binding of neutrophils with only ~10% binding to other WBC (FIG. 2B, right and 2C).

The binding affinity of the LQI tetramer peptide and 16-LQI to murine neutrophils was further assessed. Purified HDNs from 4T1-tumor bearing mice were suspended in 100 µl 0.5% BSA/1×PBS buffer with different concentrations of LQI tetramer peptide, LQI tetramer-SA complex, or a tetramer-SA complex of a control peptide (KFPDLDSRRL-PHMSL, SEQ ID NO: 1) that does not bind murine neutrophils. Analysis was performed by flow cytometry.

Figure 2D:
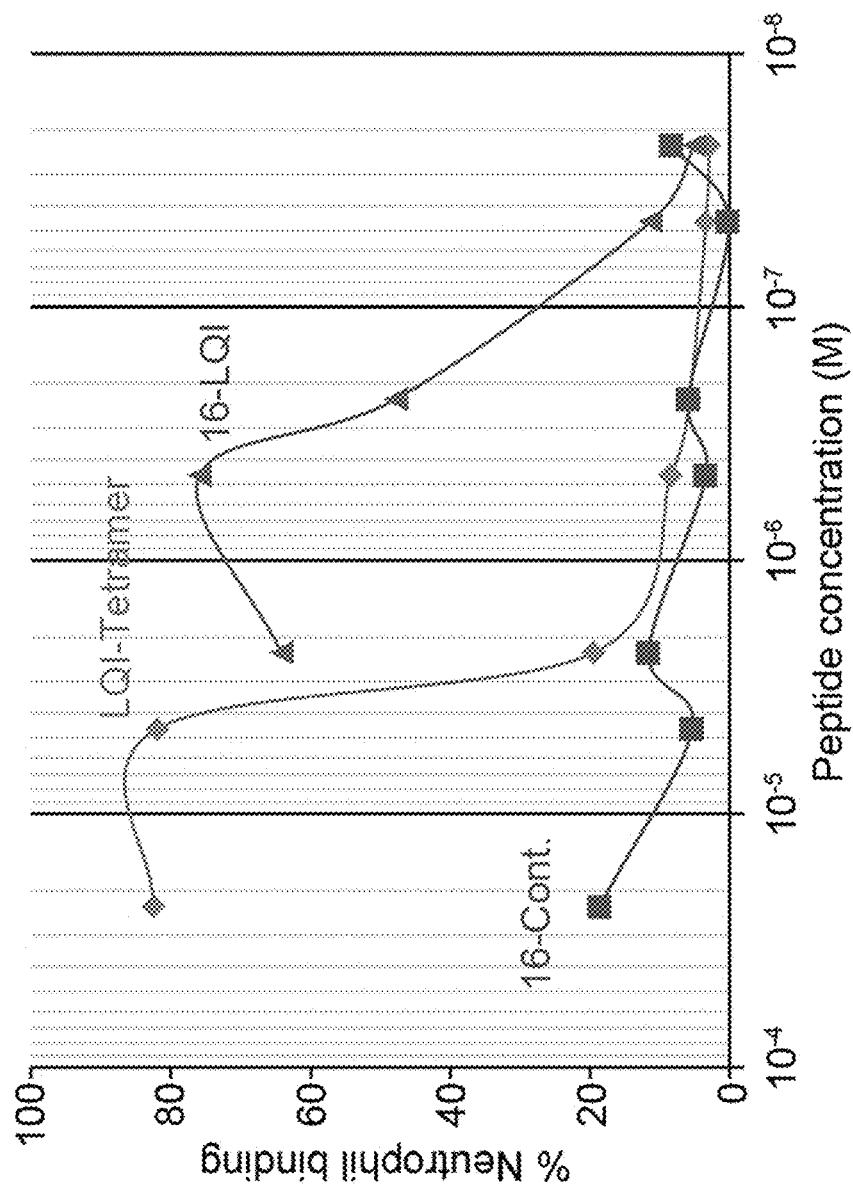
Figure 2C:
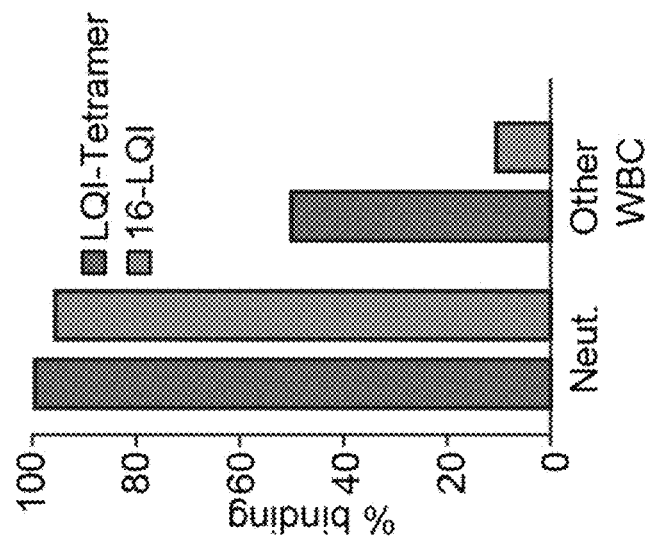

As can be seen in FIG. 2D, while the control peptide did not show binding to murine neutrophils, LQI tetramer peptide showed a $K_D$ of 3.3 μM and 16-LQI showed a $K_D$ of 250 nM. Thus, the affinity of 16-LQI for neutrophils is more than 75 times higher than that of the LQI-tetramer alone.

In order to rule out that there is a crosslinking between neutrophils when incubating with the LQI tetramer-SA-complex, flow cytometry data was analyzed to assess if there was an increase in doublet cells after incubation with the LQI tetramer-SA-complex. It is possible to examine the light scatter plots and compare the height signal of a voltage pulse (SSC-H, FSC-H) to the area values (SSC-A, FSC-A; A=Height*Width). If a doublet passes the laser beam in the flow cytometer, the width of the pulse signal (corresponds to time) will increase and therefore the value for the area (SSC-A and FSC-A) will increase. By comparing e.g. SSC-H and SSC-A it is possible to identify doublets because they are outliers in the blot. Differences were not detected in the percentage of doublets between LQI tetramer-SA-Cy3 complex bound neutrophils and control cells that were stained with only SA-Cy3 suggesting there was no cross-linking of neutrophils.

Example 3

LQI Tetramer Shows Specific Binding to Neutrophils from Healthy and Tumor Bearing Mice In order to assess the specific binding of the LQI tetramer peptide to circulating neutrophils ex vivo, blood was collected from healthy mice, from mice bearing mammary tumors (4T1) and from mice bearing lung tumors (AB12). Specifically, HDNs were purified from the circulation of naïve Balb/C, naïve C57BL/6, 4T1-tumor bearing Balb/C mice and AB12-tumor bearing C57BL/6 mice using density-gradient centrifugation (purity >95%). $0.5 \times 10^6$ purified HDNs were stained in 100 μl of preincubated 3.3 μg/ml 16-LQI-Cy3 solution for 30 min at 4° C. To evaluate binding in whole blood, 25 μl of whole blood from 4T1-tumor bearing mice were subjected to RBC lysis and remaining WBCs were resuspended in 3.3 g/ml LQI tetramer-SA-Cy3 solution for 30 min at 4° C. After staining, cells were washed and analyzed by flow cytometry.

Figure 2E:
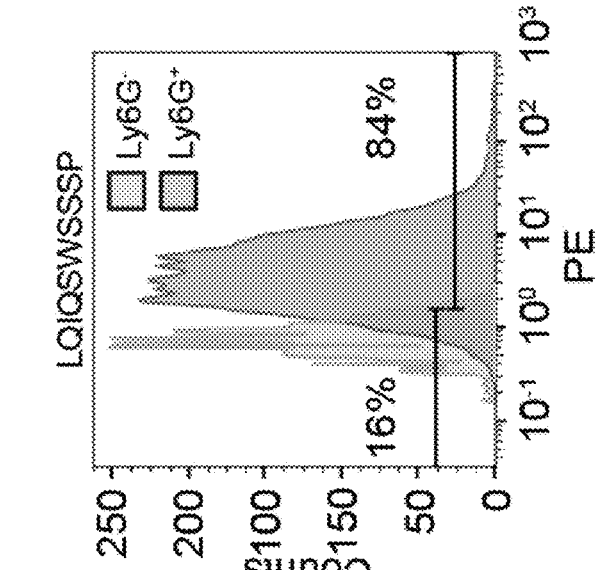
Figure 2E:
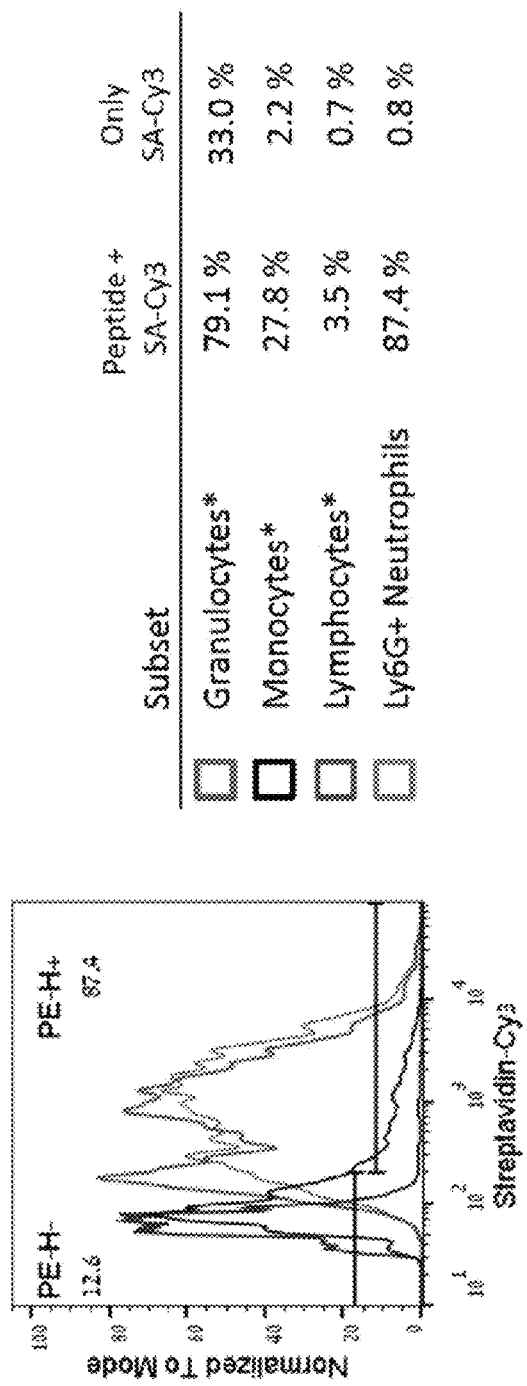
Figure 2F:
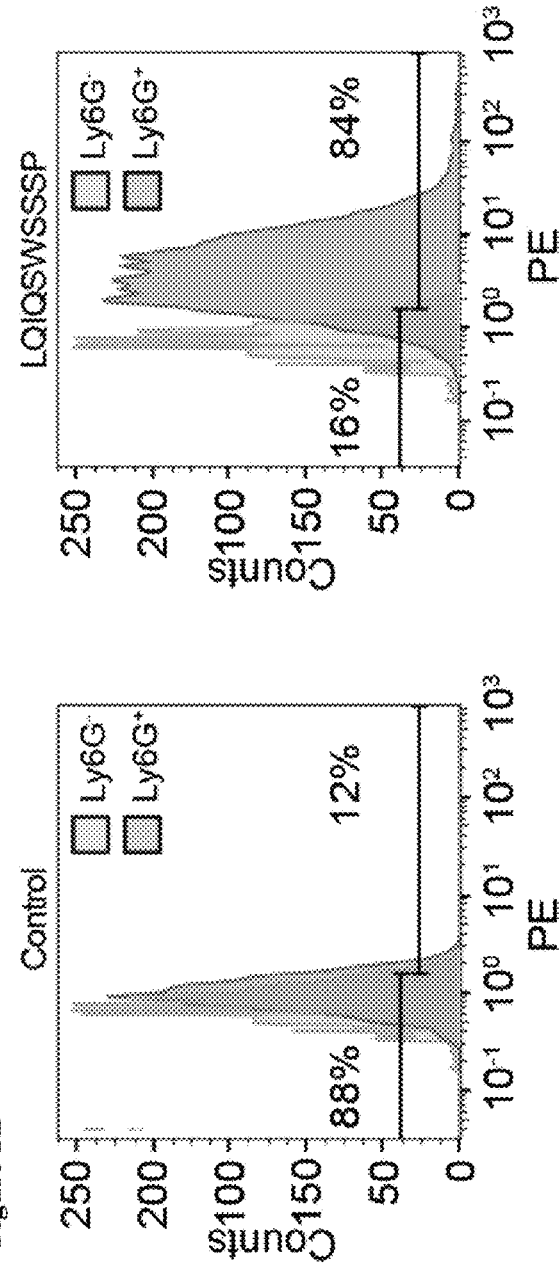

As can be seen in FIG. 2E, the 16-LQI binds with high efficacy to 87% of circulating neutrophils isolated from healthy mice. Phagocytosis, or background binding by monocytes was detected but with a lower mean fluorescence intensity (MFI). Likewise, the 16-LQI showed strong specificity to circulating neutrophils (Ly6G+ cells) in mice bearing 4T1 tumors (FIG. 2F).

Figure 2G:
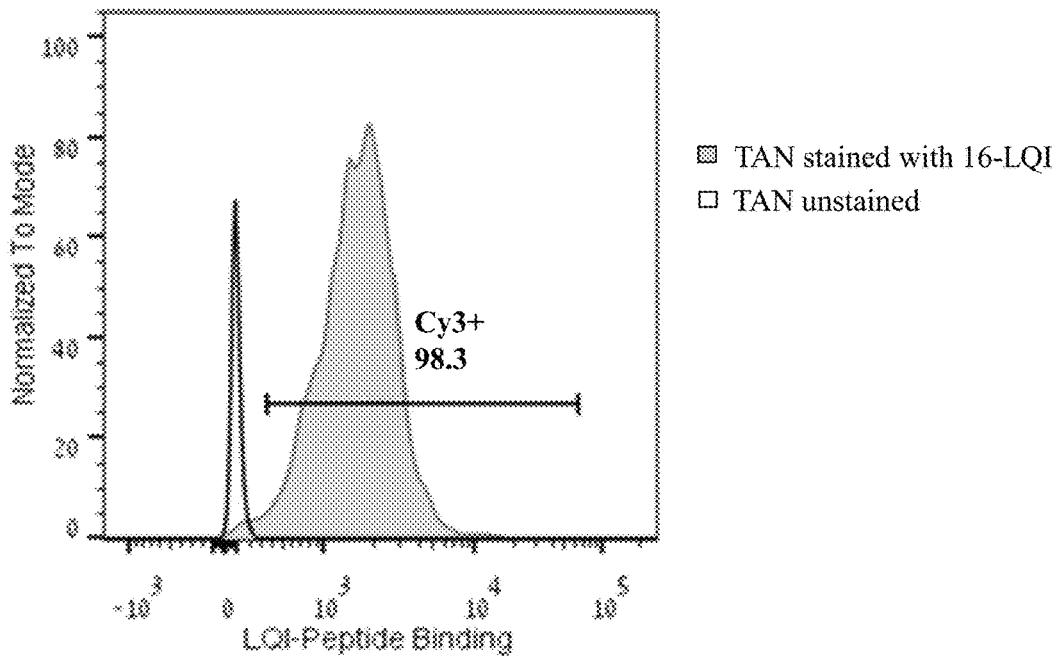

To assess the binding of LQI tetramer to tumor-associated neutrophils (TANs), TANs were purified from 4T1 tumors using the EasySep APC selection Kit (purity >90%). $0.5 \times 10^6$ purified TANs were stained in 100 μl of preincubated 3.3 μg/ml LQI tetramer-SA-Cy3 solution for 30 min at 4° C. After staining, cells were washed and analyzed by flow cytometry. The results showed remarkably high binding efficiency of LQI tetramer to TANs (98%) (FIG. 2G).

Figure 2H:
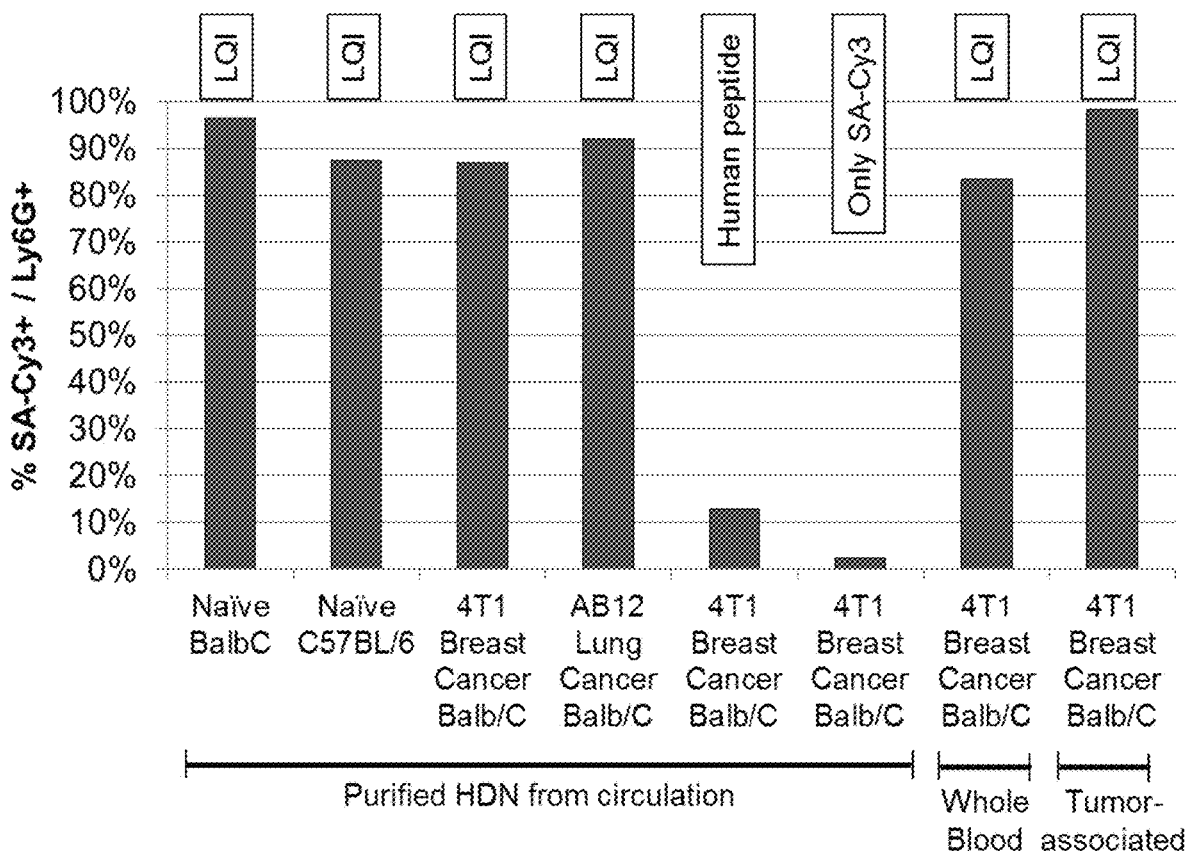
Figure 2I:

FIG. 2H shows a summary of LQI tetramer binding to all different types of neutrophils analyzed, and control tests (control peptide KFPDLDSRRLPHMSL (SEQ ID NO: 1) and SA-Cy3 only). It can be seen that the LQI tetramer peptide binds to the different neutrophils with very high efficiency. Finally, using confocal imaging it was demonstrated that 16-LQI is engulfed specifically by neutrophils (FIG. 2I).

Example 4

LQI Tetramer-Coated Nanospheres Show Specific Targeting to Neutrophils In Vitro

Figure 4:
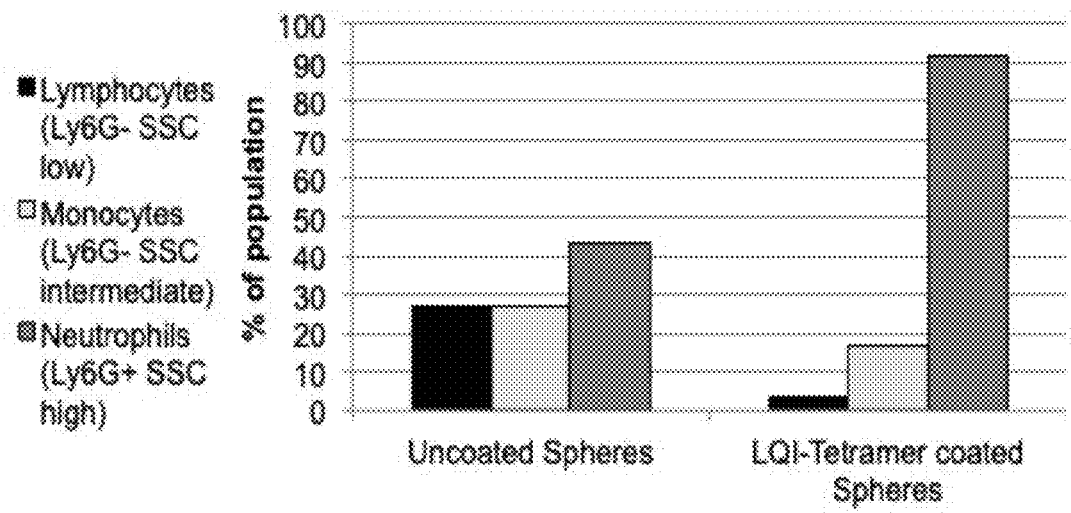
FIG. 4: A bar graph showing the in vitro binding of uncoated or LQI tetramer-coated nanospheres to neutrophils or other WBCs from 4T1 tumor bearing mice. Analysis was performed by flow cytometry.

Streptavidin-coated fluorescent nile red nanospheres (700-900 nm) were coated with the LQI tetramer via its biotin-tag, by incubating 20 μl of the nanospheres with 5 μl of 30.9 μM LQI tetramer solution for 30 min, followed by washing by centrifugation at 3000 g for 10 min. The binding specificity of these tetramer-coated nanospheres towards purified HDNs from 4T1-tumor bearing mice was then assessed in vitro. $1 \times 10^6$ density-gradient purified HDNs from 4T1 tumor bearing Balb/C mice were incubated with 20 μl of uncoated or LQI tetramer-coated nanospheres for 1 hour at 37° C. After three washes, cells were analyzed by flow cytometry. As shown in FIG. 4A, the LQI tetramer coating increased neutrophil binding up to 92%, compared to 44% binding of the uncoated nanospheres. In addition, unspecific uptake by other WBCs was reduced by the tetramer coating.

Example 5

LQI Tetramer-Coated Nanospheres Show In Vivo Targeting to Neutrophils from Mice with Inflammatory Conditions Peritonitis Streptavidin-coated fluorescent nile red nanospheres, uncoated (control) or coated with the LQI tetramer peptide (as described in Example 4), were injected into the tail vain of mice with peritonitis. After 2 hours, mice were sacrificed and blood and peritoneal lavage were harvested and examined for presence of sphere-positive neutrophils, by staining with CD45-APC and Ly6G-Vio antibodies followed by washing and analysis by flow cytometry.

Figure 5A:
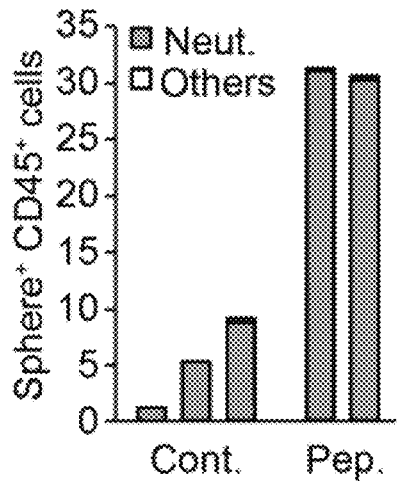
FIGS. 5A-B: Bar graphs showing the percent of nanospheres-carrying neutrophils (nanosphere+neutrophils) detected in (5A) the blood of peritonitis-induced mice and (5B) the peritoneal lavage of peritonitis-induced mice. Each bar represents one mouse. "cont."=uncoated nanospheres. "Pep."=LQI tetramer-coated nanospheres. "Neut"=neutrophils. "Others"=other WBCs.
Figure 5B:
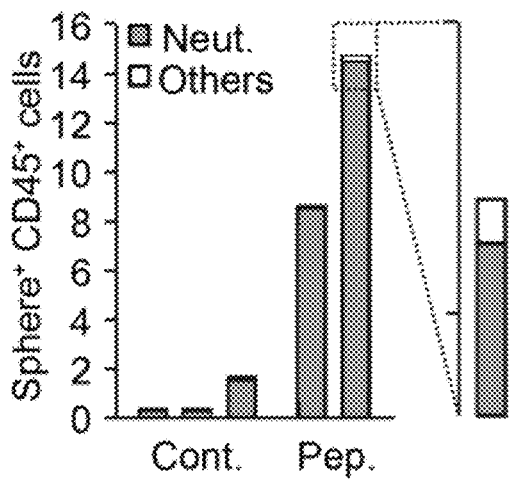

As shown in FIGS. 5A and 5B, an increased percentage (30%) of nanosphere-positive neutrophils was detected in the circulation (FIG. 5A), and between 8-15% in the peritoneum (FIG. 5B) in mice injected with LQI tetramer-coated spheres. Mice injected with uncoated spheres showed only 2-9% nanosphere+neutrophils in the circulation and between 0.5 to 2% in the peritoneum.

The results also indicate the in vivo stability of the LQI tetramer-coated nanospheres.

Acute Colitis

Colitis was induced in mice though administration of dextran sulfate sodium (DSS) in the drinking water for 5 days and then switching to regular tap water. On day 7, the mice were injected with LQI tetramer-coated nanospheres and sacrificed on the following day. Presence of sphere-positive neutrophils was examined by staining with CD45 and Ly6G antibodies followed by washing and analysis by flow cytometry.

Figure 6A:
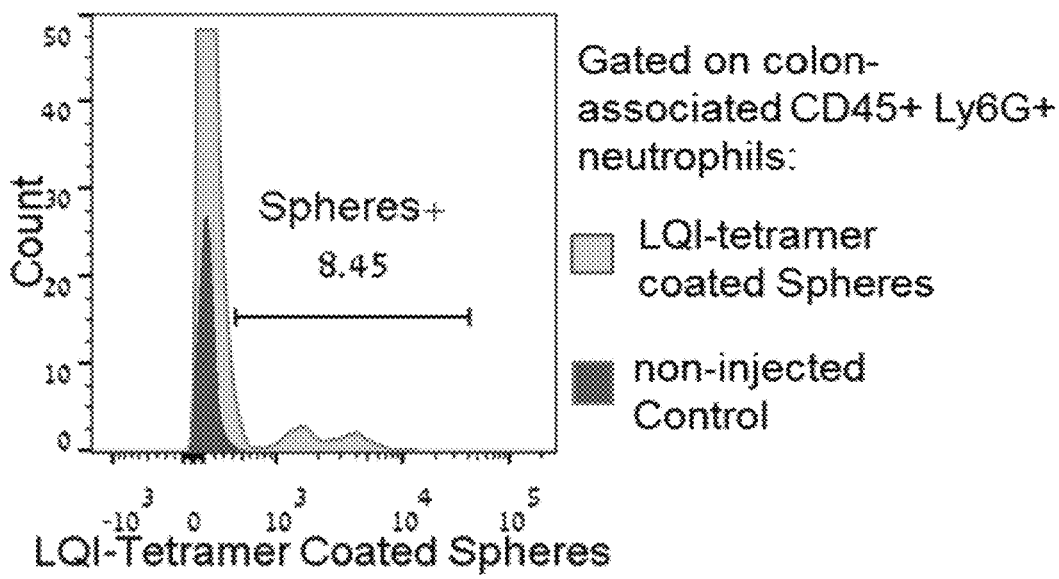
FIGS. 6A-B: (6A) A histogram obtained by flow cytometry analysis showing LQI tetramer-coated nanosphere uptake by neutrophils in a mouse with colitis. (6B) Micrographs showing an overview image of the distal colon, cut open and flattened, taken with the typhoon laser scanner (left), and images acquired with binocular fluorescence microscope showing magnified area of nanosphere infiltration (right). Highlighted dots represent areas of high fluorescence.
Figure 6B:
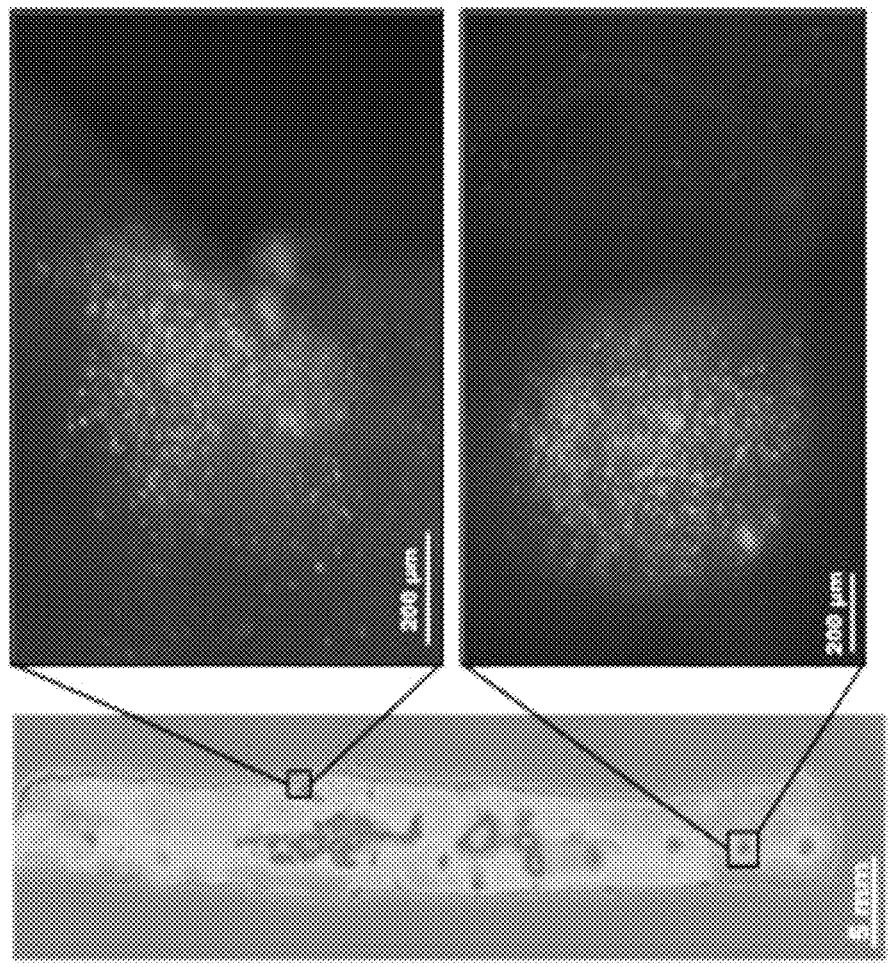

As presented in FIG. 6A, nanosphere-injected mice exhibited accumulation of fluorescent cells in the inflamed colons, indicating that the LQI tetramer-coated nanospheres efficiently target colon-infiltrating neutrophils. The accumulation of fluorescent signal in the colon was also visualized in the whole organ using the typhoon fluorescent laser scanner as well as fluorescent binocular microscope (FIG. 6B).

The uptake of LQI tetramer-coated nanospheres inside the circulation was also evaluated. The results showed that there was a decrease in the percentage of sphere+ Ly6G+ neutrophils over time. More specifically, 2 h after injection 8.4% of circulating neutrophils were positive for sphere uptake, 5 h after injection 7.09% of circulating neutrophils were positive for sphere uptake and 24 h after detection only 1.3%. of circulating neutrophils were positive for sphere uptake.

Example 6

LQI Tetramer-Coated Nanospheres Dispersion and Arrival at the Site of the Tumor in 4T1-Tumor Bearing Mice To test whether LQI tetramer-coated nanospheres accumulate in tumors, 4T1-tumor bearing mice were i.v. injected with LQI tetramer-coated nanospheres. The mice were sacrificed after 6.5 hours and the presence of neutrophils carrying fluorescent nanospheres in the tumor and in whole blood was examined. Nanospheres-positive neutrophils were detected in the blood, and low percentage of nanosphere+ neutrophils was detected in a single cell suspension prepared from the tumor. The accumulation of LQI tetramer-coated nanospheres in the tumor is further examined in additional time points after nanosphere administration, up to 24 and 48 hours post injection.

Example 7

LQI Tetramer Peptide Shows High Stability in Serum Ex Vivo

Figure 7:
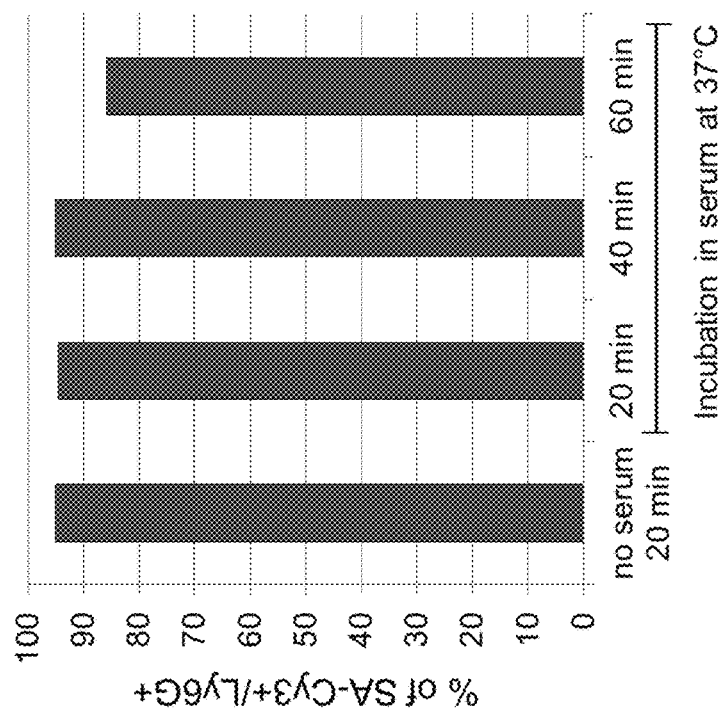
FIG. 7: A bar graph showing the percentage of SA-Cy3+ cells from total population of purified HDNs, after preincubation of LQI tetramer in BSA/1×PBS buffer (control) or in mouse serum (20-, 40- or 60-minute incubation). Analysis was performed by flow cytometry.

To assess LQI tetramer stability, LQI tetramer peptide (7.7 µM) was incubated in mouse serum at 37° C. for 20 min, 40 min or 1 hour. After incubation, 150 µl of 0.5% BSA/1×PBS buffer with 3.3 µg/ml SA-Cy3 and $0.7\times10^6$ HDNs purified from the circulation of tumor-bearing mice were added to the 40 µl of serum including the peptide. As stability readout, the binding capacity of the LQI-tetramer to HDNs was examined. As a control, LQI tetramer was incubated at 37° C. for 20 min in 40 µl 0.5% BSA/1×PBS buffer. HDNs were incubated for 30 min at 4° C., washed and analyzed by flow cytometry. As depicted in FIG. 7, binding of neutrophils is well maintained, decreasing from 95% binding of all HDNs after 20- and 40-min incubation, to 85% after 1 hour incubation, suggesting good stability of the LQI-tetramer. The minor decrease in binding could be due to hydrolysis of the peptide.

Example 8

LQI Tetramer Peptide does not Affect Neutrophil Viability

Figure 8A:
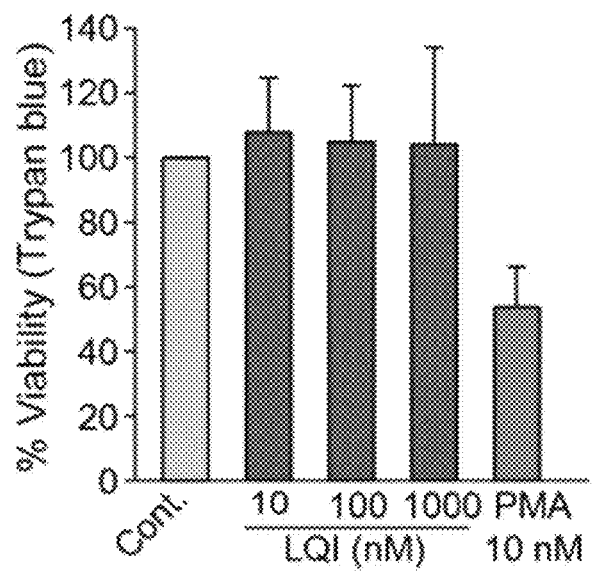
FIGS. 8A-G: Effect of the LQI-tetramer on neutrophil function (8A) Neutrophils were incubated for 6.5 hours in the presence or absence of 10, 100 and 1000 nM of LQI tetramer. Treatment with 10 nM PMA was used as positive control. Viability was determined by trypan exclusion and compared to untreated control neutrophils as shown in a bar graph. (8B-C) Bar graphs summarizing FACS analysis of (8B) Annexin+ and (8C) Annexin+PI+neutrophils following 30 min incubation in the presence or absence of 10, 100 and 1000 nM of LQI tetramer. Treatment with 10 nM PMA was used as positive control. (8D) Bar graph of mean fluorescence intensity (MFI) of CD11b expression in neutrophils following 30 min incubation in the presence or absence of 10, 100 and 1000 nM of LQI tetramer. Treatment with 10 nM PMA was used as positive control. (8E) Line graph of ROS production by neutrophils in the presence of absence of 10, 100 and 1000 nM of LQI tetramer. Treatment with 100 nM PMA was used as positive control. (8F) Bar graph of Neutrophil migration (Boyden chamber) towards control medium or media containing LQI-tetramer 100 nM and 1 μM). Data represents average of 5 high power fields (HPF). (8G) Bar graph of Neutrophil migration (Boyden chamber) towards control medium or media containing CXCL2 (100 ng/μl) alone or supplemented with LQI-tetramer (100 nM and 1 μM). The LQI-tetramer (100 nM and 1 μM LQI) was added to neutrophils in the upper chamber. Data represents average of 5 high power fields (HPF).
Figure 8B:
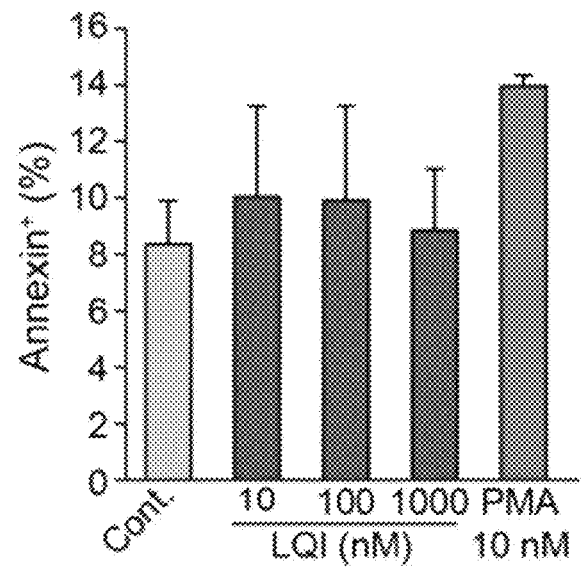
Figure 8C:
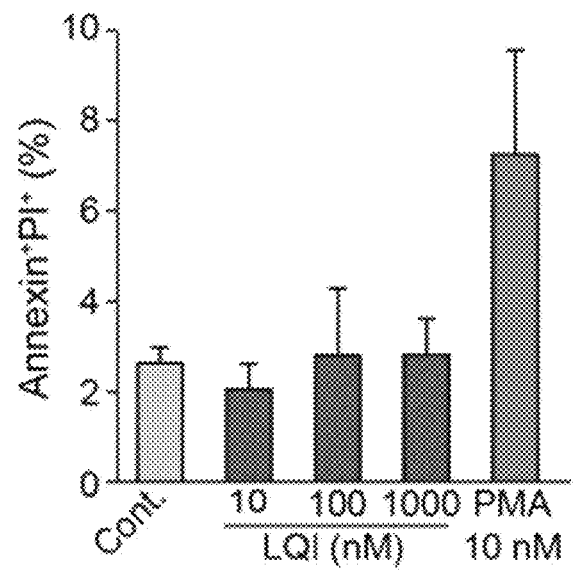

Neutrophils were isolated from the circulation of Balb/C mice bearing 4T1 tumors. The neutrophils ($0.5\times10^6$) were then treated with increasing concentrations of LQI tetramer peptide (310 nM, 3.1 µM and 31 µM) and incubated in OptiMEM 0.5% FCS for 6.5 hours. Control neutrophils received corresponding amount of water in OptiMEM 0.5% FCS for 6.5 hours. As a positive control phorbol 12-myristate 13-acetate (PMA) was used, a well-described molecule that stimulates production of reactive oxygen species (ROS). Two complementary assays to assess neutrophil survival were used: Counting of live neutrophils by trypan exclusion and FACS analysis of Annexin V+ (apoptotic) and PI+ (dying/dead) neutrophils. Referring to Annexin/PI assay, the incubation time was only 30 min. Cells were stained with FITC Annexin V according to manufacturer's instruction, 0.5 µl of PI 1 mg/ml were added to 300 µl of stained cell suspension 30 sec before flow cytometry analysis. As can be seen in FIGS. 8A (cell counting) and 8B-C (FACS analysis), using both strategies there were no significant differences in neutrophil viability in any of the peptide concentrations compared to control cells (untreated). This indicates that the LQI tetramer peptide has no significant effect on neutrophil viability.

Example 9

LQI Tetramer Peptide does not Affect Neutrophil Function

Figure 8D:
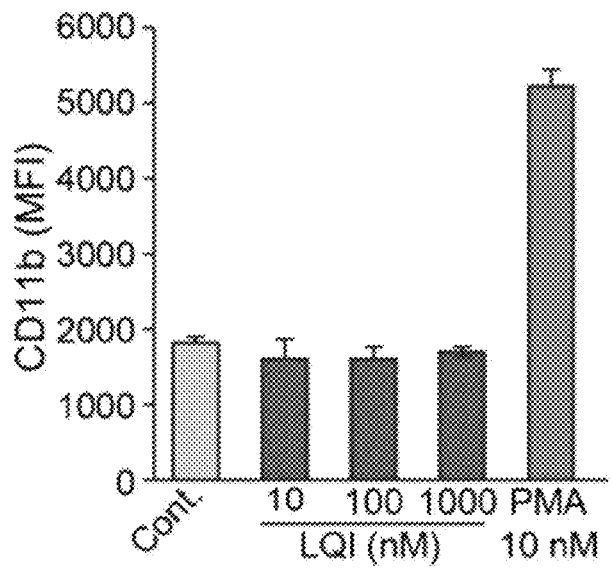
Figure 8E:
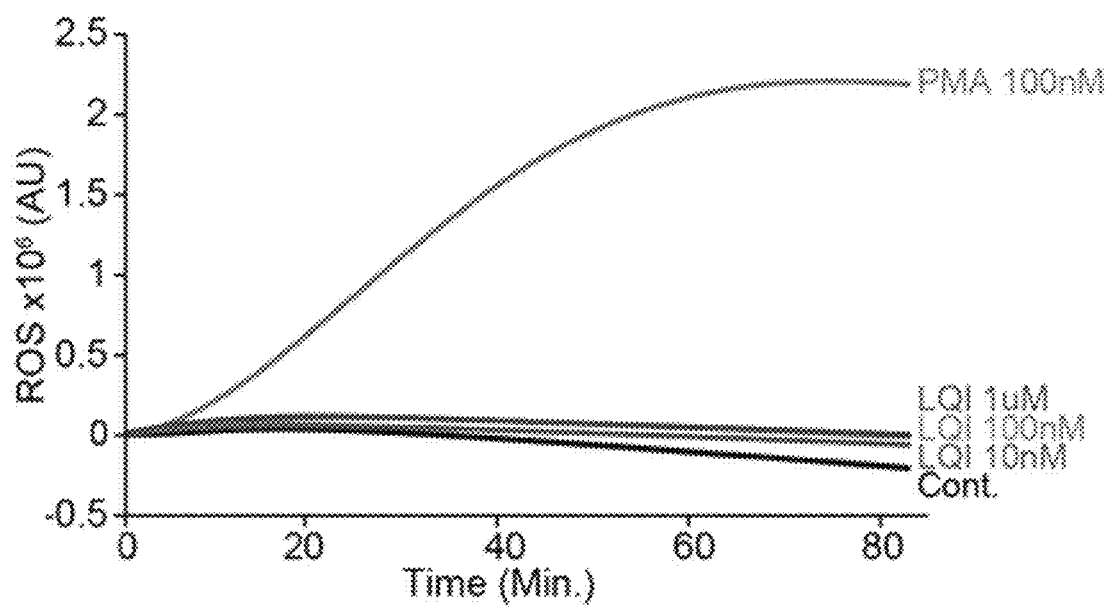
Figure 8F:
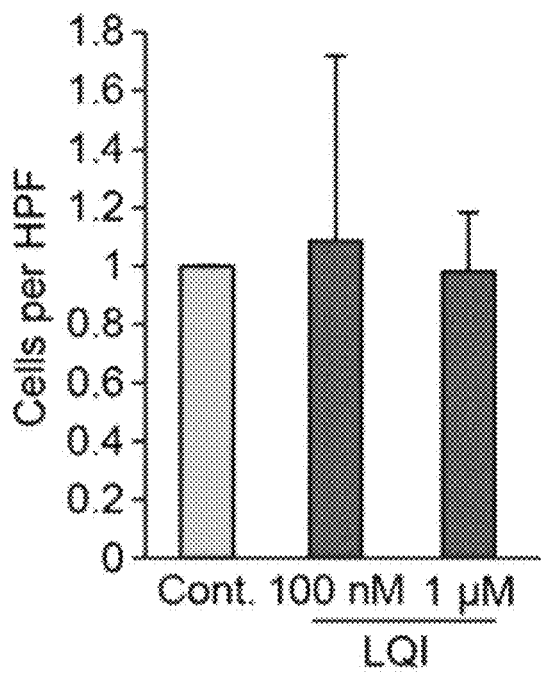

In order to assess the functional consequences of exposing neutrophils to the neutrophil-targeting LQI tetramer peptide, circulating HDNs purified from tumor-bearing mice were incubated with the synthetic LQI tetramer peptide. The consequences on neutrophil activation, neutrophil generated reactive oxygen species (ROS), neutrophil migration and neutrophil mediated cytotoxicity towards 4T1 cancer cells were then assessed. Further, it was shown that the LQI-tetramer does not itself act as a chemoattractant (FIG. 8F).

Activation

Neutrophils were isolated from the circulation of Balb/C mice bearing 4T1 tumors. The neutrophils were then treated with increasing concentrations of the LQI tetramer peptide (310 nM, 3.1 µM and 31 µM) or 10 nM PMA as a positive control for activation. Corresponding amount of water was added to the control cells (untreated). Cells were stained with CD11b-FITC for 30 min at 4° C. and then washed and analyzed by flow cytometry, to determine the surface expression of CD11b as a proxy for neutrophil activation. FIG. 8D shows that while PMA induced a dramatic increase in CD11b surface expression, neutrophils treated with the LQI tetramer peptide did not show any significant difference in CD11b surface expression compared to control ($H_2O$ treated). This indicates that the LQI tetramer peptide has no significant effect on neutrophil activation.

ROS Production

Neutrophils were isolated from Balb/C mice bearing 4T1 tumors. The neutrophils were then treated with increasing concentrations of the LQI tetramer peptide (39 nM, 390 nM and 3.9 µM). Treatment with 10 nM PMA served as a positive control and equal volumes of $H_2O$ as a negative control. A luminol based assay was used to determine the extent of ROS production. Briefly, after treatment with the LQI tetramer peptide or PMA, luminol was added to cells and production of chemiluminescence was measured over a time course of 35 min. Measured chemiluminescence corresponds to ROS production, and accumulation of ROS was calculated. As can be seen in FIG. 8E, it was found that while PMA induced a dramatic increase in ROS production, neutrophils treated with the LQI tetramer peptide did not show any significant difference in ROS production compared to control ($H_2O$ treated). This indicates that the LQI tetramer peptide has no significant effect on ROS production by neutrophils.

Migration

Figure 8G:
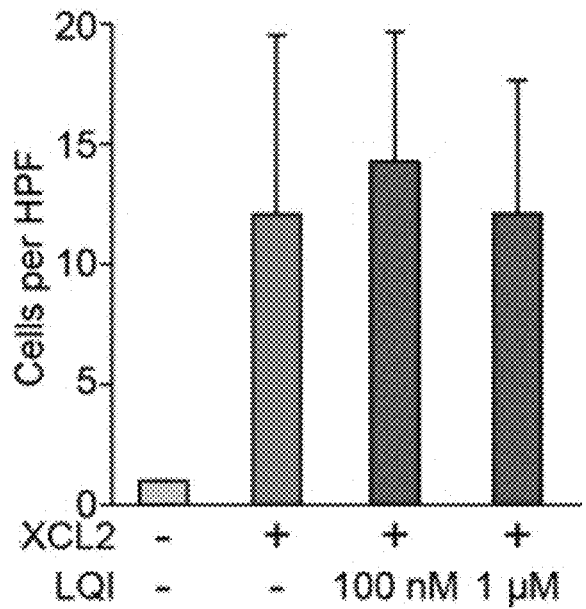

Neutrophils were isolated from 4T1 tumor bearing Balb/C mice and the effect of the LQI tetramer peptide on their migration was tested in a Boyden chamber. The purified HDNs were placed in the upper chamber of a transwell (pore size 5 µm) in 2% FCS/RPMI medium. The lower chamber contained either only 2% FCS/RPMI medium or the chemokine CXCL2 to induce neutrophil migration. The LQI tetramer peptide was added in two different concentrations (3.09 µM and 309 nM) to the upper chamber. The assay was stopped after 1.5 h incubation, five pictures of each well were taken, counted and averaged. The experiment was done in triplicates. As can be seen in FIG. 8G, adding the LQI tetramer peptide to the cells in the upper compartment of the transwell had no significant effect on neutrophil migration.

Cytotoxicity Toward 4T1 Cancer Cells

To exclude possible effects of the LQI peptide on the ability of HDNs to kill cancer cells, LQI tetramer peptide was added to the co-culture of 4T1 cancer cells and HDNs, and the percentage of killing was measured and compared to that without LQI tetramer treatment. In more details, 5.000 luciferase-labeled 4T1 breast carcinoma cells were cultured for 18 hours. Then, 1×10$^5$ HDNs purified from the circulation of 4T1 tumor bearing mice were added. The co-culture was incubated overnight. The LQI tetramer was then added in various concentrations as well as the KFP tetramer (KFPDLDSRRLPHMSL, SEQ ID NO: 1) which served as a control. The next day, luciferin dependent chemiluminescence was measured and the percentage of killing was calculated compared to control wells that were not cultured with HDNs. For every sample, control 4T1 cells without HDNs were treated with the corresponding concentration of peptide within the medium. The % tumor cell lysis was calculated as follows: % tumor lysis=(1−[luminescence of samples with neutrophils]/[luminescence of samples in medium])×100%.

Figure 9:
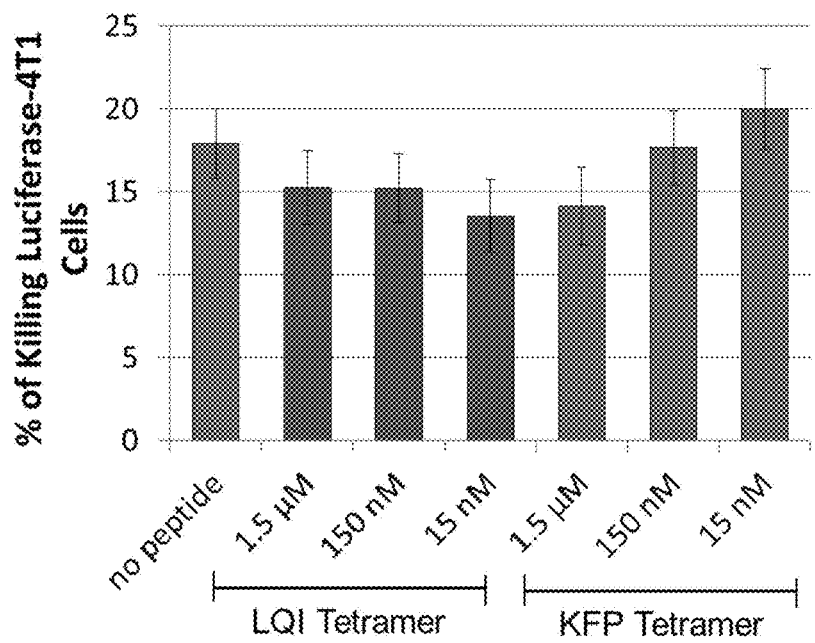
FIG. 9: A bar graph showing the percentage of dead 4T1 cells after incubation with HDNs only, HDNs+LQI tetramer, or HDNs+KFP tetramer, relative to control cells that were not cultured with HDNs.

As can be seen in FIG. 9, 17.9% of the 4T1 cells were killed after incubation with HDNs without LQI tetramer addition. The percentage of killing in the treated samples (LQI tetramer or control KFP tetramer) varied between 13.6-20%. None of these differences in killing was significant, indicating that the LQI tetramer peptide does not affect the ability of HDNs to kill cancer cells.

In order to further examine if the LQI tetramer peptide has an effect on the viability of the cells, 4T1 cells were plated and incubated in 10% FCS/DMEM for 4 hours. Then, cells were treated with different concentrations of LQI tetramer peptide (31 nM, 310 nM and 3.1 μM) or control KFP tetramer (hPeptide, 3.9 μM). The cytotoxic drug cytochalasin B (Cyto) was used as a positive control. 18 hours later, resazurin solution was added in an amount that equaled to 10% of the culture medium volume. 2 hours later, fluorescence was measured as an indicator for cell viability (function of metabolic activity using the conversion of resazurin dye).

Figure 10:
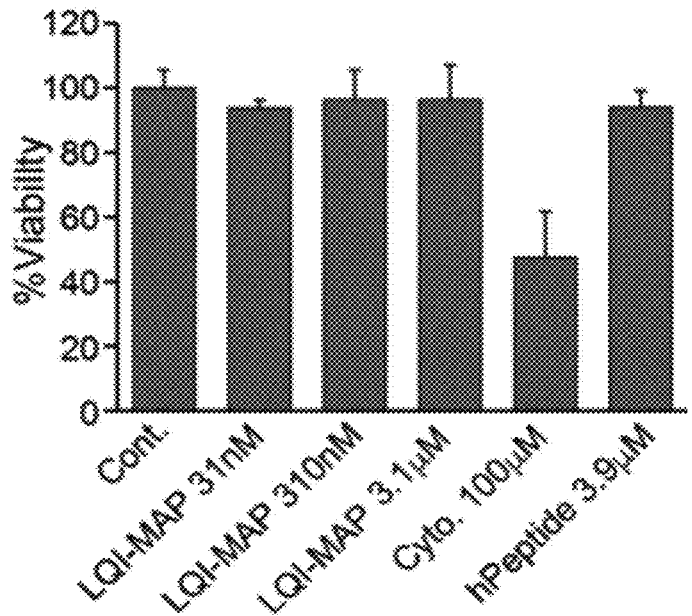
FIG. 10: A bar graph showing resazurin-based viability assay of 4T1 cells, untreated or treated with LQI tetramer peptide, KFP tetramer or cytochalasin B (positive control).

As shown in FIG. 10, both LQI tetramer peptide and control KFP tetramer did not affect cell viability.

The same assay is used to test the cytotoxicity of LQI tetramer toward other cells, for example normal epithelial cells, normal endothelial cells and fibroblasts.

Example 10

Identification of Peptides Binding to Human Neutrophils

By using a phage library screen and alternating rounds of positive selection (binding to neutrophils) and negative selection (binding to mononuclear fraction) as represented in FIG. 11 and described hereinabove, 8 potential peptides have been discovered, having the ability to bind specifically to human neutrophils isolated from healthy individuals. The library was tested on a pool of 10 healthy individuals in order to eliminate individual effects and to find peptides relevant to a wide panel of individuals. The sequences of the 8 relevant peptides are provided in Table 4.

TABLE 4

Sequences of peptides binding with high efficiency to circulating human neutrophils

| Peptide name | SEQ ID NO: | Peptide sequence |
|---|---|---|
| 1.1 (KFP) | 1 | KFPDLDSRRLPHMSL |
| 27 (LAT) | 2 | LATTHMVFSPDH |
| 4 (PSS) | 3 | PSSNLESTPLSLL |
| 14 (SSL) | 4 | SSLMTTQLIATSI |
| PEL | 5 | PELDSKPYFPPL |
| ELV | 6 | ELVTASMPRPNN |
| SLE | 7 | SLESSPMAQLPQ |
| SEL | 8 | SELRSTPLLVPS |

Figure 12:
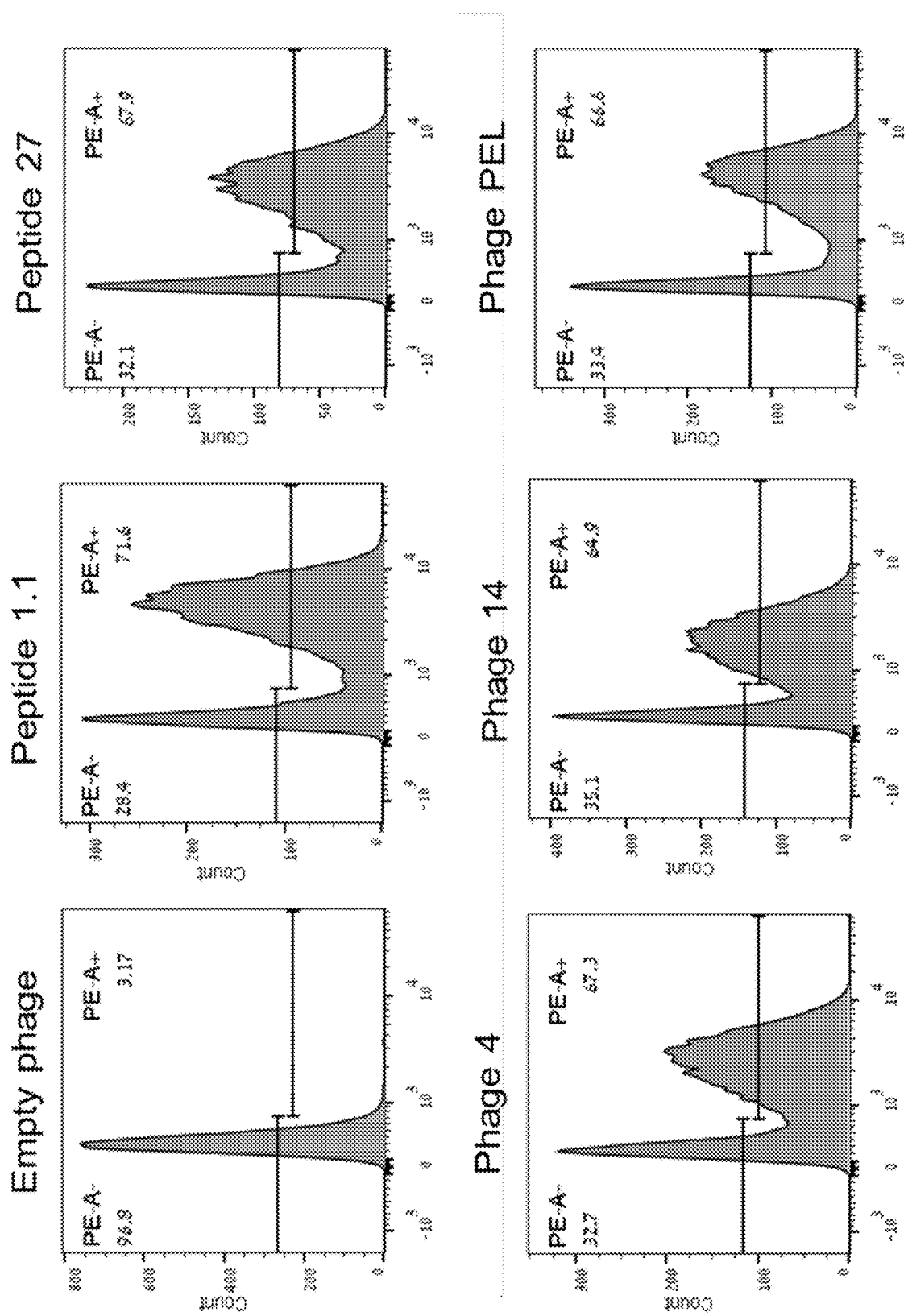
FIG. 12: Representative histograms showing the binding level of an empty phage (control) and 8 human peptide-phages to circulating neutrophils.
Figure 12:
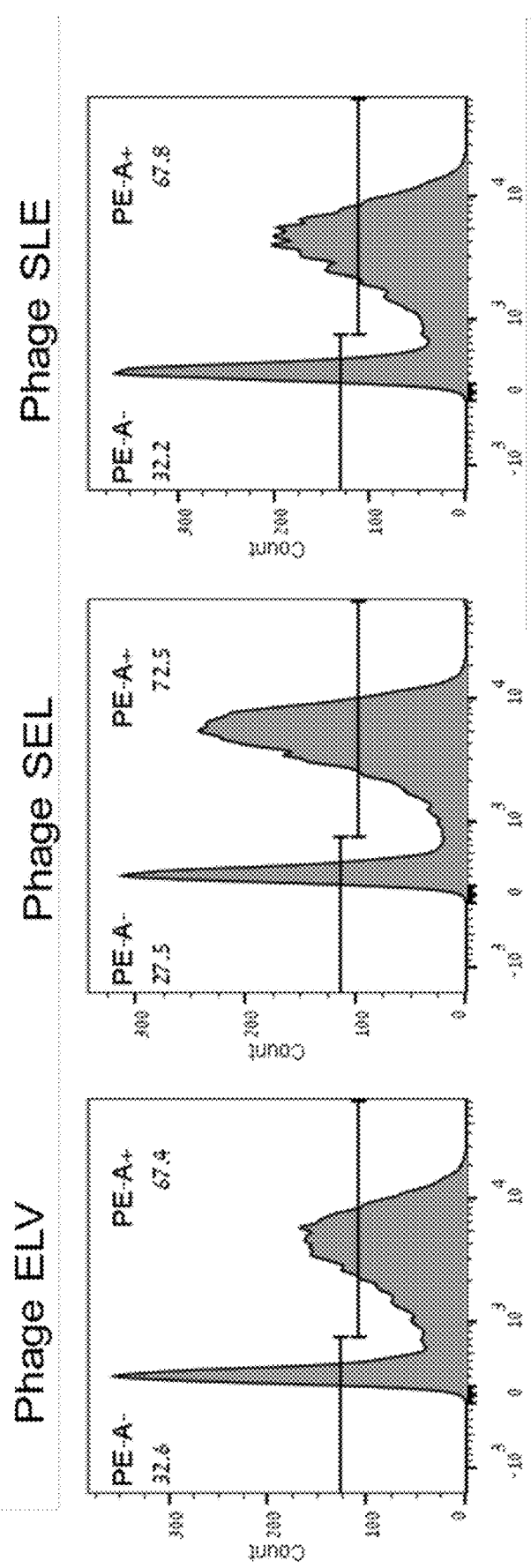

Whole blood from a healthy volunteer was mixed with 3% dextran in 0.9% NaCl in a 1:1 ratio and left at RT for 25 min to allow erythrocyte sedimentation. Following red blood cell lysis, 0.5×10$^6$ WBCs were incubated with each phage separately. Binding of different phages was examined using the neutrophils from the same individual. Neutrophils were identified as CD66b$^+$ SSC$^{high}$, and the level of phage binding assessed using PE-conjugated anti-M13 antibody. As can be seen FIG. 12, whereas the empty phage was found to bind to circulating neutrophils at very low levels, a significant binding of the peptide-expressing phages to neutrophils was observed.

Example 11

Figure 13A:
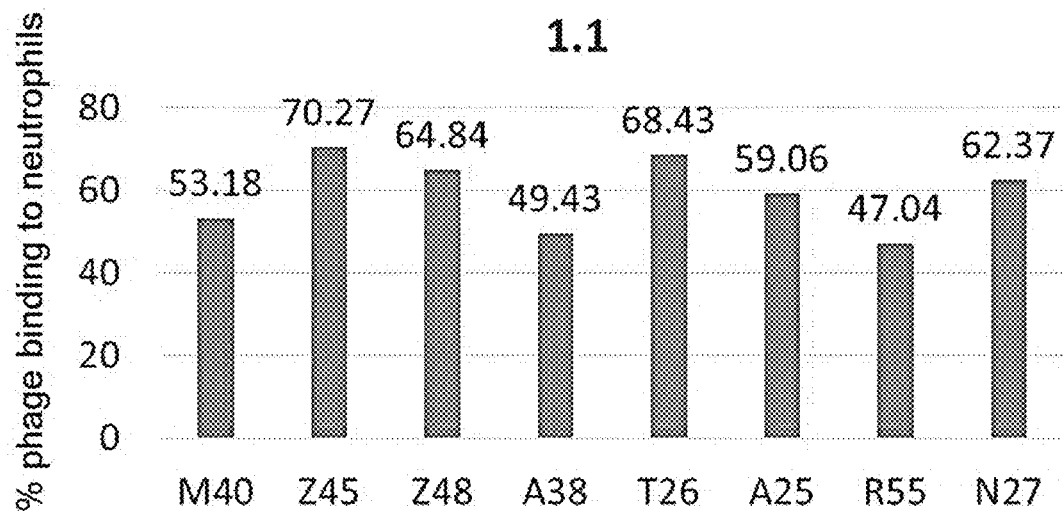
FIGS. 13A-13I: Bar graphs showing the percentage of binding of peptides-phages to neutrophils from different healthy individuals, for the following peptides: 1.1 (SEQ ID NO: 1, FIG. 13A), 27 (SEQ ID NO: 2, FIG. 13B), 4 (SEQ ID NO: 3, FIG. 13C), 14 (SEQ ID NO: 4, FIG. 13D), PEL (SEQ ID NO: 5, FIG. 13E), ELV (SEQ ID NO: 6, FIG. 13F), SLE (SEQ ID NO: 7, FIG. 19G) and SEL (SEQ ID NO: 8, FIG. 13H). M40, Z45, Z48, A38, T26, A25, $R^{55}$ and N27 represent different individuals. (13I) Bar graph summarizing the binding of phages expressing different peptides to CD66b+ neutrophils from different donors (colored circles). Open black circles represent an outlier excluded from the overall average.
Figure 13B:
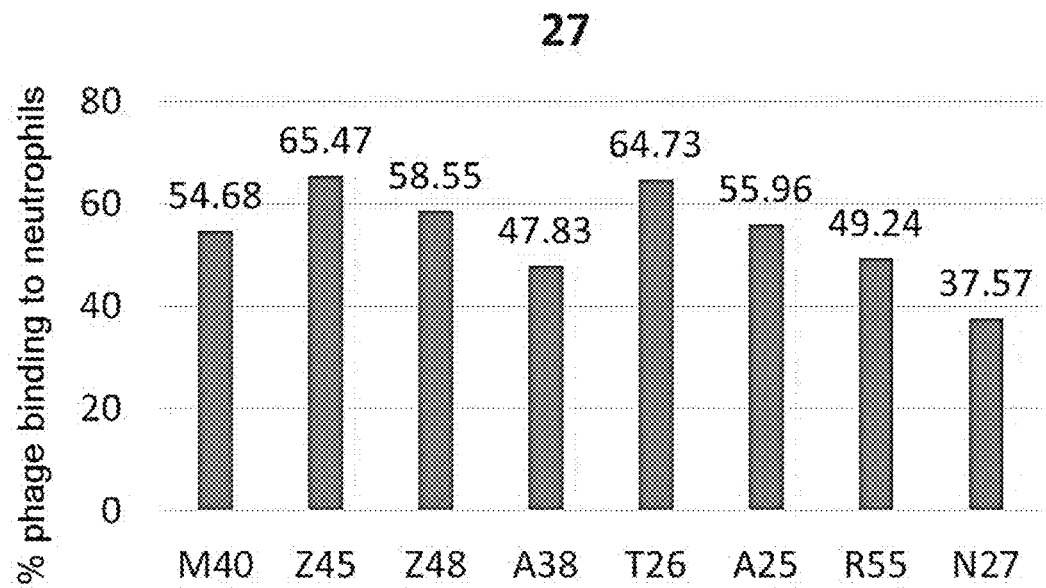
Figure 13C:
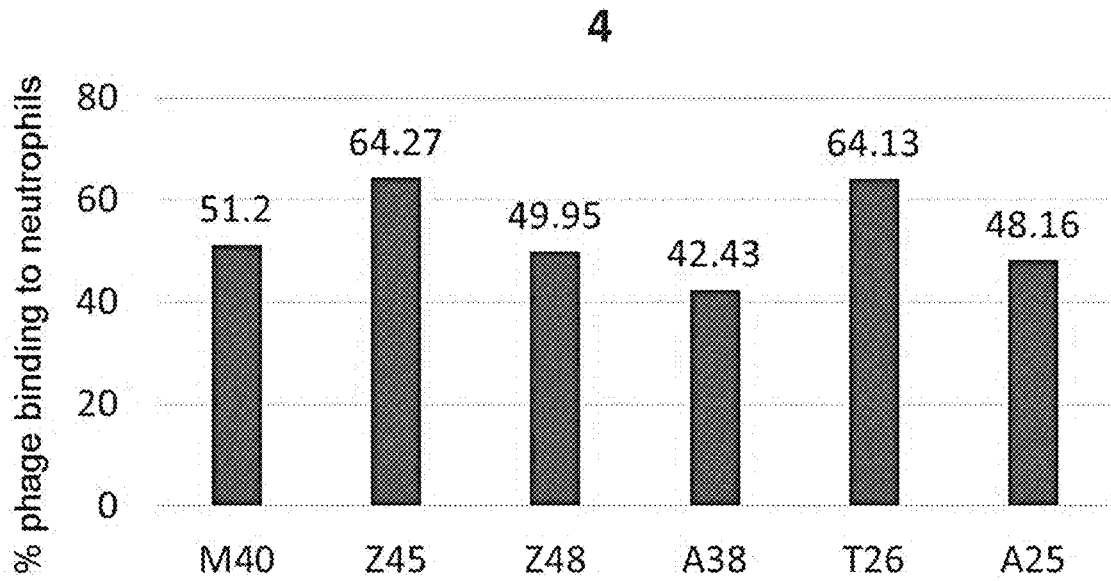
Figure 13D:
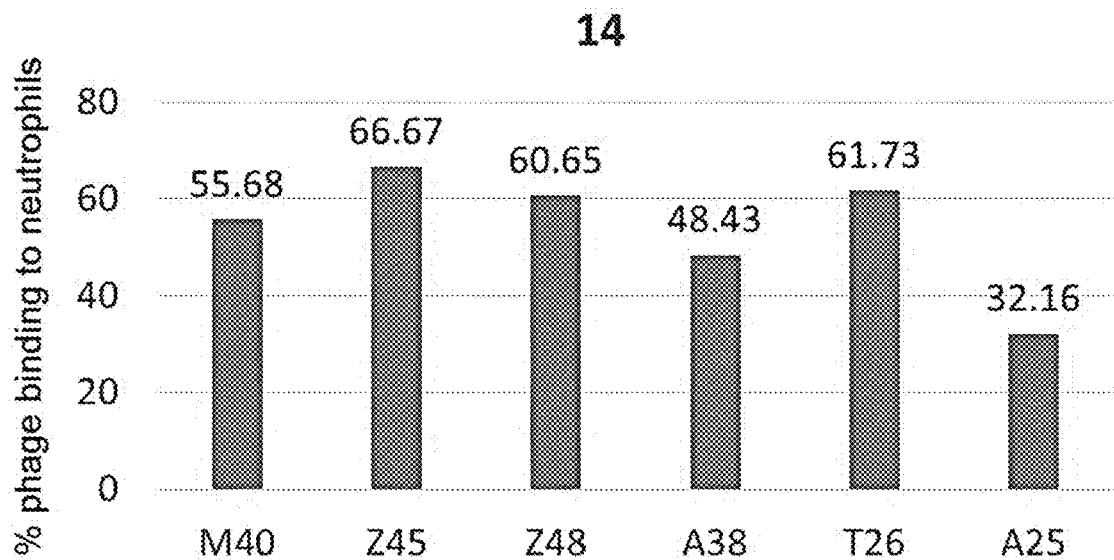
Figure 13E:
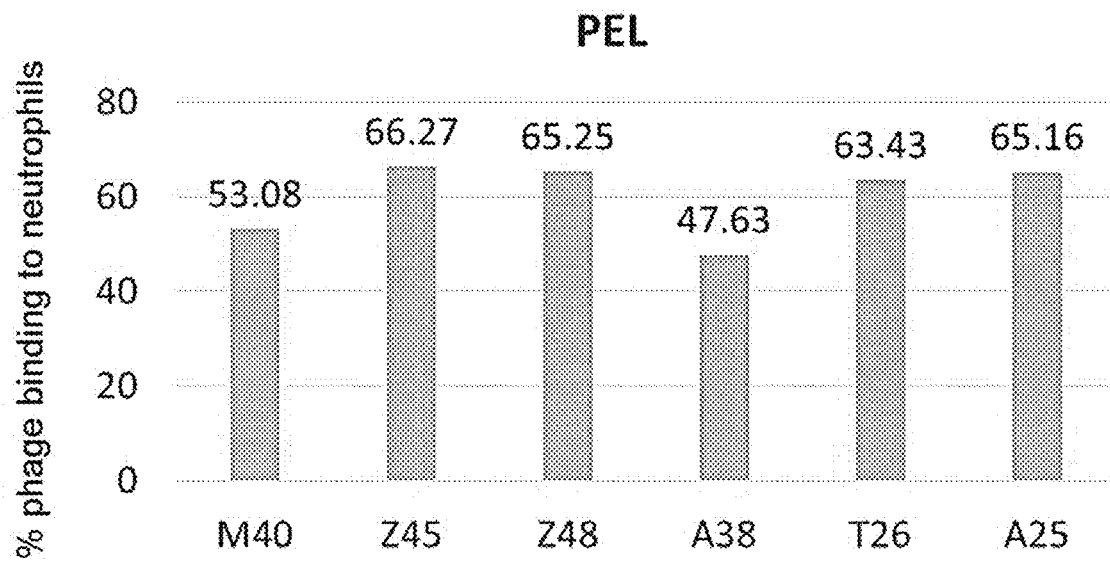
Figure 13F:
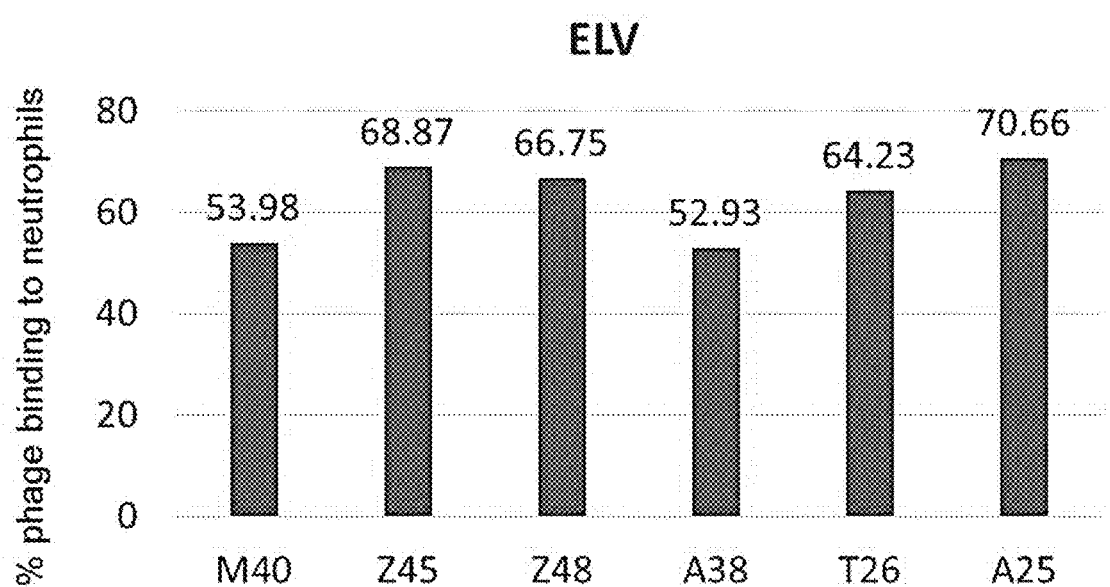
Figure 13G:
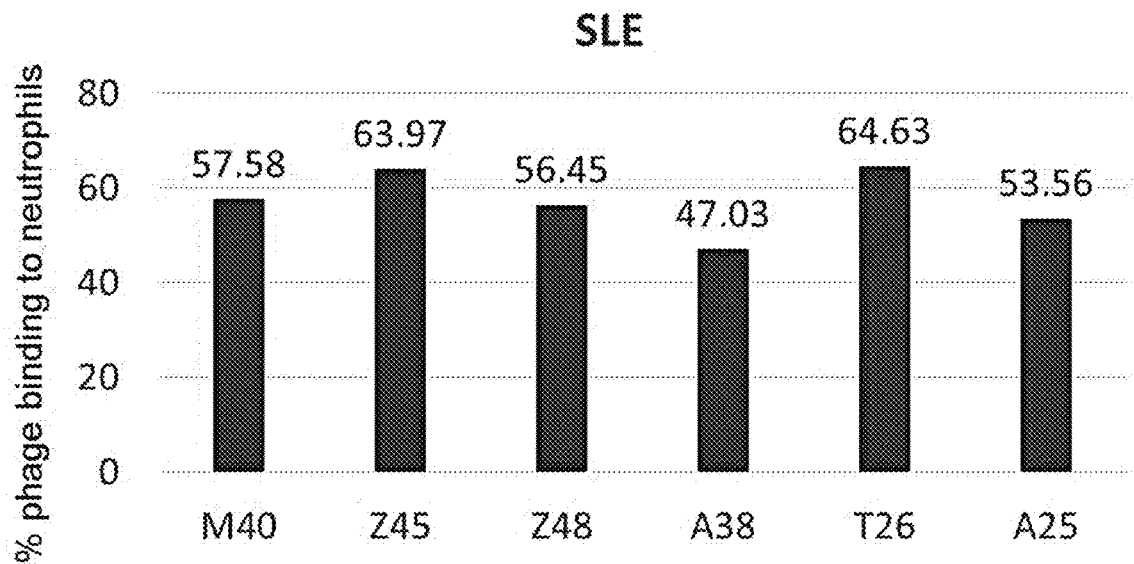
Figure 13H:
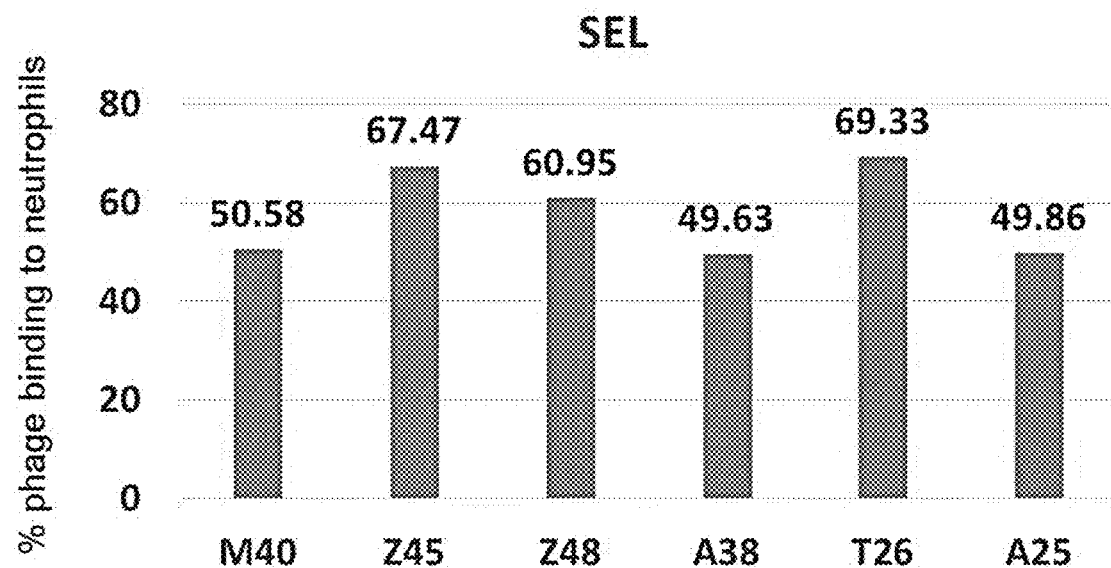
Figure 13I:
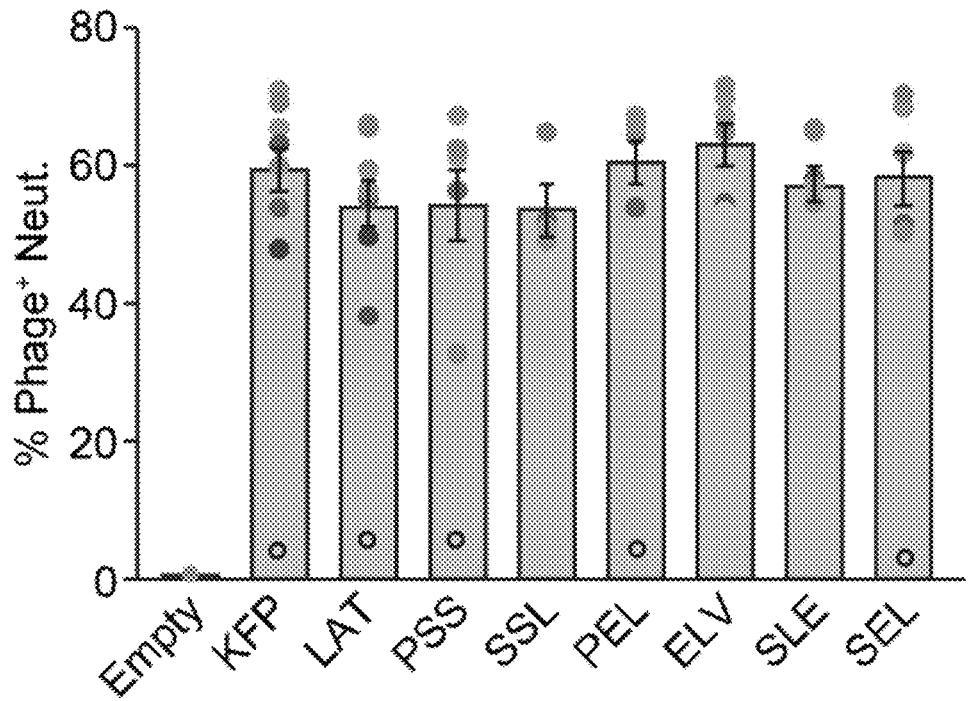

Human Neutrophil-Binding Peptides Show Binding to Circulating Neutrophils from Healthy Volunteers In order to assess the binding efficiency of each peptide to human circulating neutrophils, and the level of variability between individuals, the individual binding of each peptide to 5-8 healthy volunteers was assessed. Blood withdrawn from healthy volunteers was overlaid on 3% dextran in 0.9% NaCl in a 1:1 ratio and left at RT for 25 min to allow erythrocyte sedimentation. Residual RBCs were lysed by adding water for 30 sec and stopped by adding PBS×5 supplemented with 2.5% BSA. Following red blood cell lysis, 0.5×10$^6$ WBCs were incubated with each phage separately. The level of binding of the different phages to the neutrophils was then assessed by flow cytometry. Neutrophils were identified based on a CD66b$^+$ SSC$^{high}$ gating, and the level of phage binding was assessed using PE-conjugated anti-M13 antibody for specific phage staining. As shown in FIGS. 13A-H, the results showed a range of binding between 30-70%, depending on the peptide and the individual. Importantly all phage bound to significant number of neutrophils for all subjects and the various peptides all bound ~60% of circulating neutrophils on average (FIG. 13I).

Example 12

Figure 14:
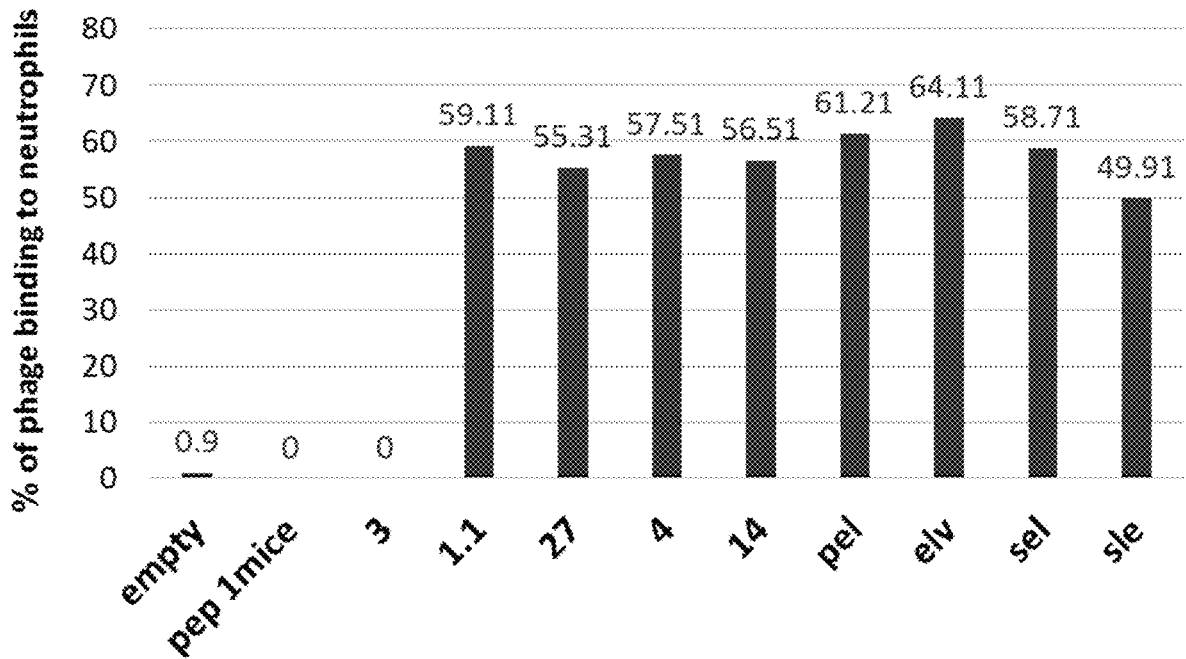
FIG. 14: Bar graph showing the percentage of binding of peptides-phages to circulating neutrophils from a lung cancer patient. Empty=empty phages; peplmice=LQI (SEQ ID NO: 9); 3=a negative control peptide (SSLMTTQLIATSI, SEQ ID NO: 4).

Human Neutrophil-Binding Peptides Show High Affinity to Circulating Neutrophils from Lung Cancer Patients The binding of the phages to neutrophils isolated from lung cancer patients was tested. Whole blood from one lung cancer patients was mixed with 3% dextran in 0.9% NaCl in a 1:1 ratio and left at RT for 25 min to allow erythrocyte sedimentation. Residual RBCs were lysed by adding water for 30 sec and stopped by adding PBS×5+2.5% BSA. Total number of cells was then counted and $0.5 \times 10^6$ WBCs were incubated with each phage. Neutrophils were identified based on a $CD66b^+$ $SSC^{high}$ gating, and the level of binding of the different phages was assessed by flow cytometry using PE-conjugated anti-M13 antibody for phage staining. Empty phages as well as the tetrameric construct comprising the peptide LQI (that binds murine neutrophils but not human neutrophils), and an irrelevant peptide denoted "3", were used as negative controls for the specificity of the human peptides. As can be seen in FIG. 14, all 8 peptides showed strong affinity to the circulating neutrophils.

Example 13

KFP-Tetramer Multiantigen Generation and Characterization

Figure 15A:
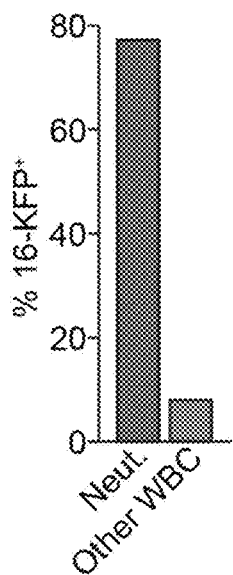
FIGS. 15A-F: (15A) Bar graph of representative quantification of 16-KFP binding to neutrophils ($SSC^{high}$) and other WBC ($SSCL^{low}$) from a healthy donor. (15B) Line graph showing no effect of KFP-tetramer on neutrophil ROS production. (15C-D). Bar graphs showing no effect of KFP-tetramer on neutrophil viability as measured by (15C) microscopy or (15D) flow cytometry. (15E) Bar graph showing the KFP-tetramer is not chemoattractive to neutrophils. (15F) Bar graph showing no effect of KFP-tetramer on neutrophil attraction to CXCL2.
Figure 15B:
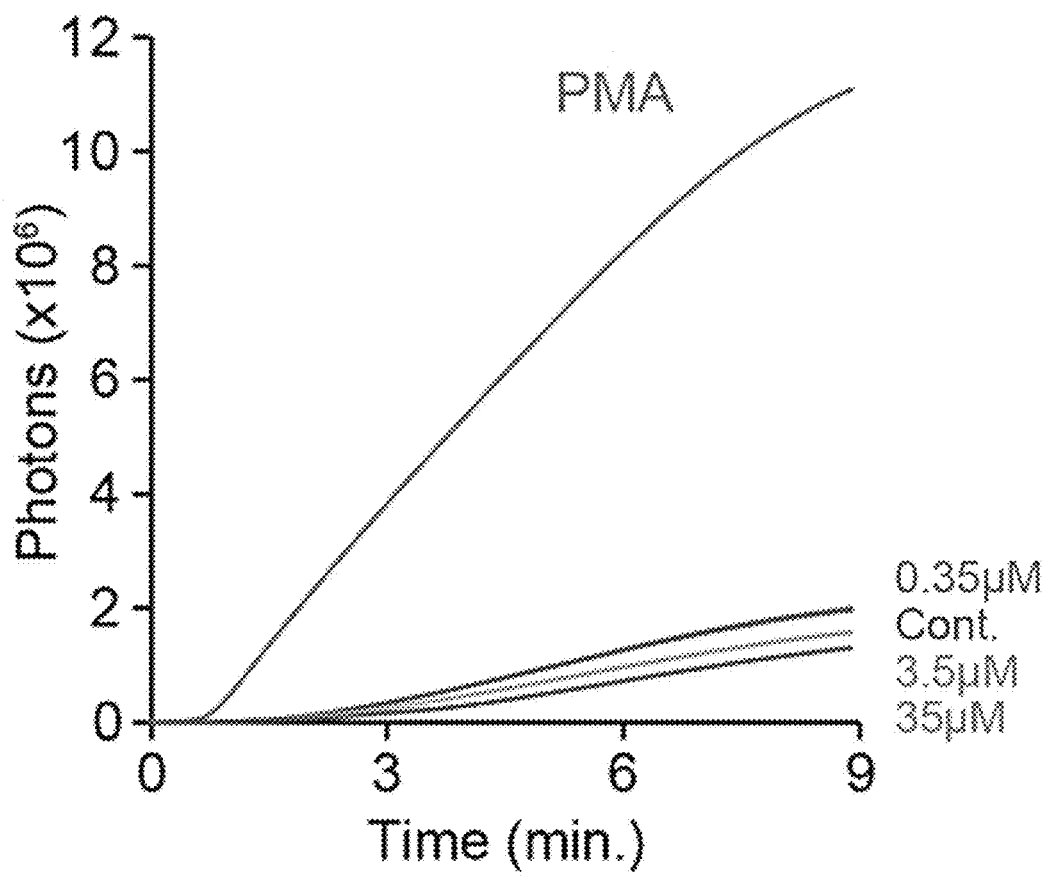
Figure 15C:
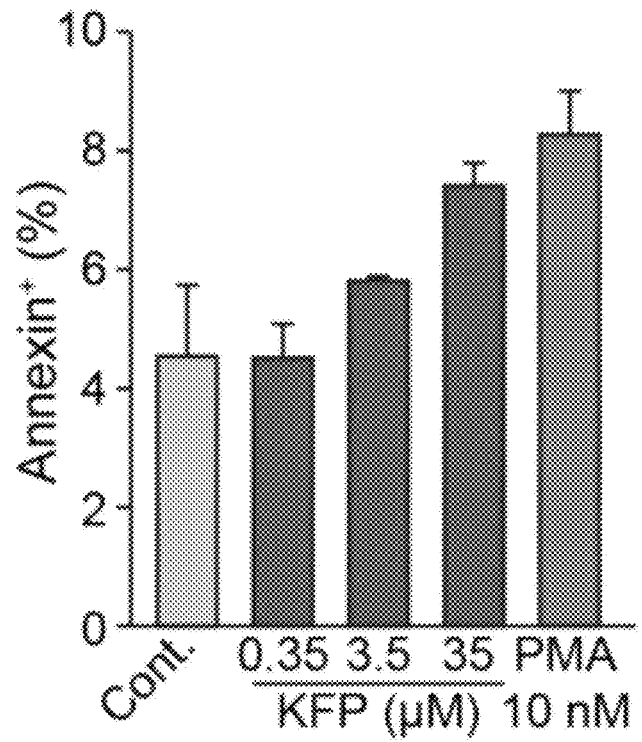
Figure 15D:
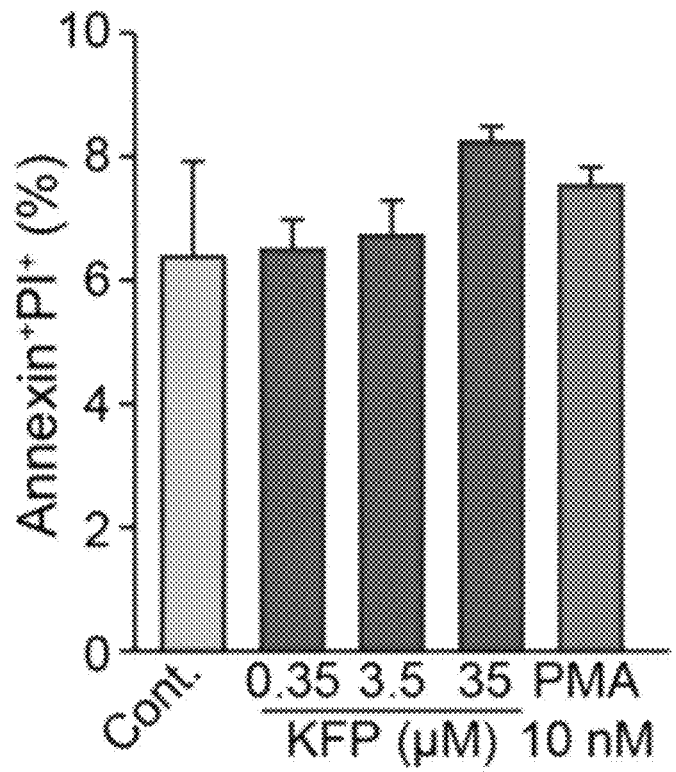
Figure 15E:
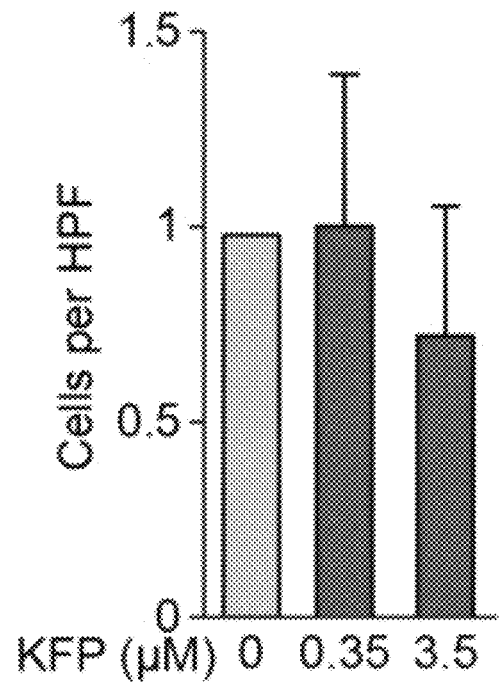
Figure 15F:
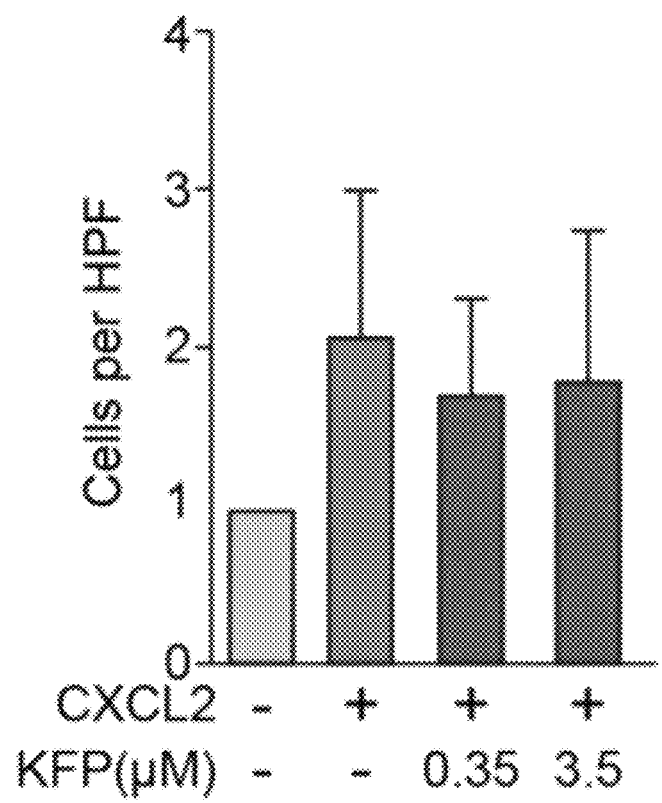
Figure 16A:
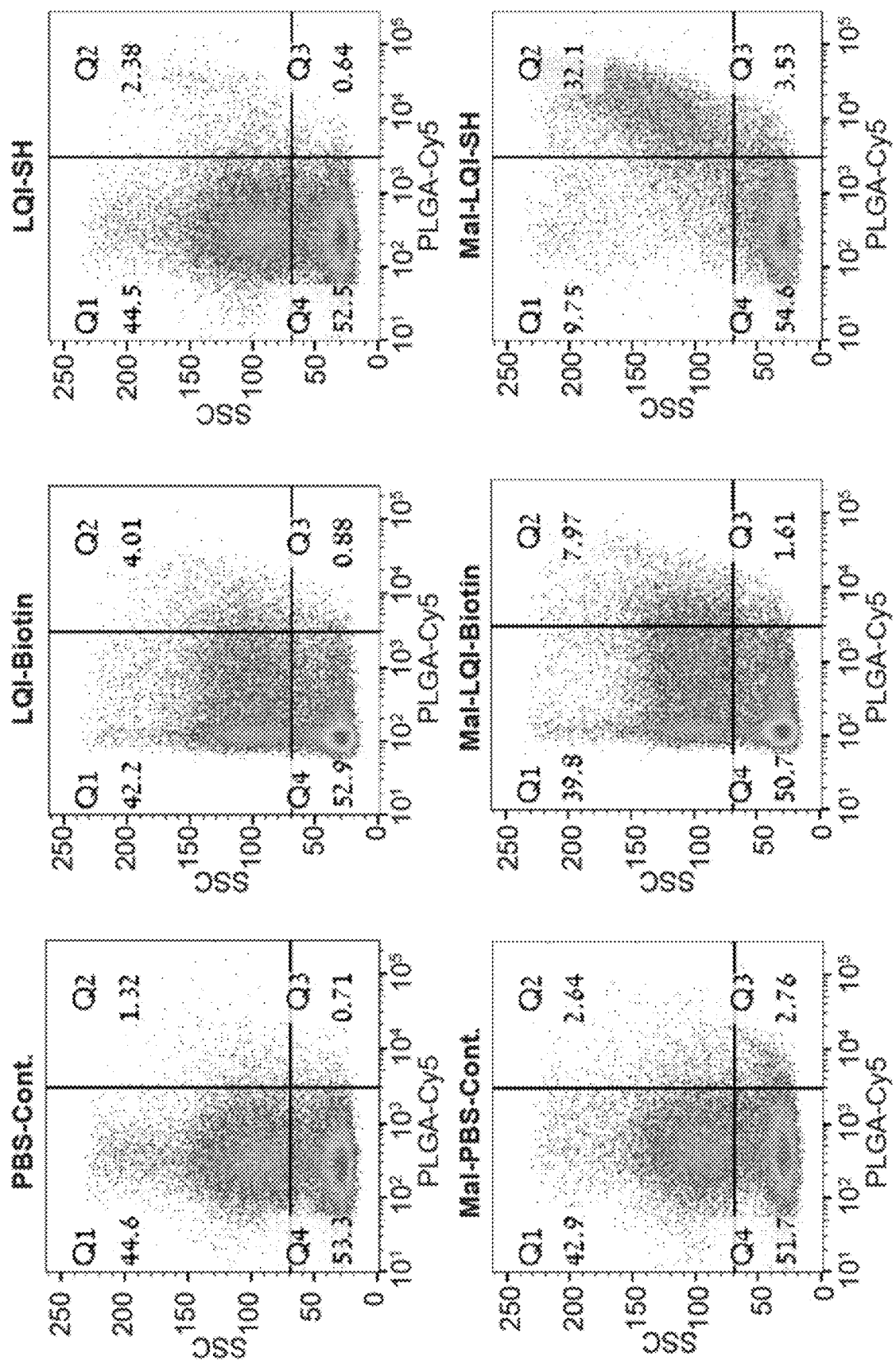
FIGS. 16A-F: Optimization of LQI Tetramer Coating of PLGA NP. (16A) Dot plots showing NP uptake for neutrophils (high side scatter Q1+Q2) and other WBC (low side scatter Q3+Q4) for the indicated NP formulations. (16B) Bar chart of the MFI of PLGA-Cy5 for neutrophils and other WBC incubated with indicated NP formulations. (16C) Bar graph of the ratio of PLGACy5 MFI between neutrophils and other WBC. (16D) Bar graphs of the binding of PLGA-PEG-Maleimide NP decorated with different concentrations of the LQI tetramer with c-terminal cysteine. PLGA-Cy5 MFI gated on neutrophils. (16E) Dot plots showing NP uptake for neutrophils (high side scatter Q1+Q2) and other WBC (low side scatter Q3+Q4) for the LQI-tetramer NP. (16F) Electron microscopy images of uncoated NP and LQI tetramer coated NP.
Figure 16B:
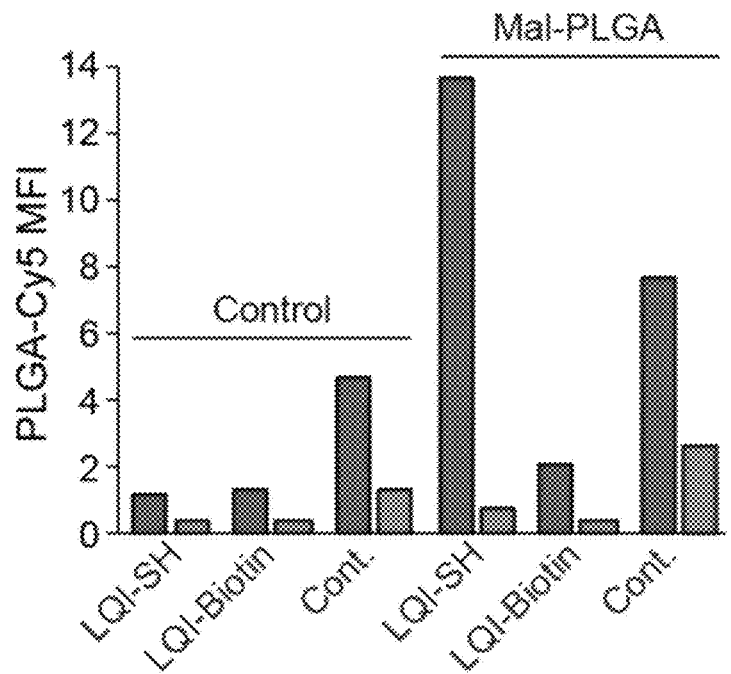
Figure 16C:
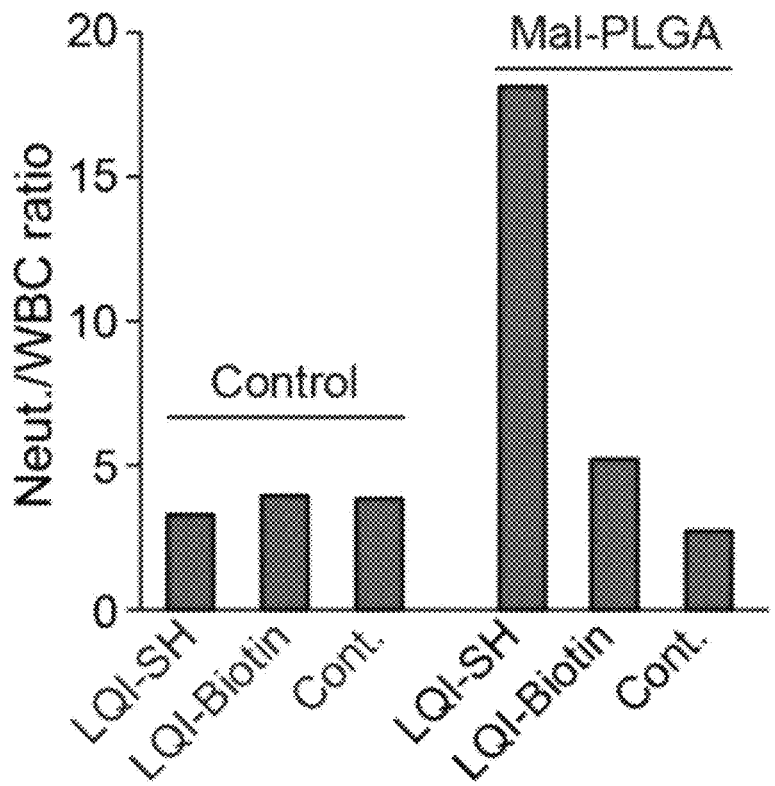
Figures 16D, 16E:
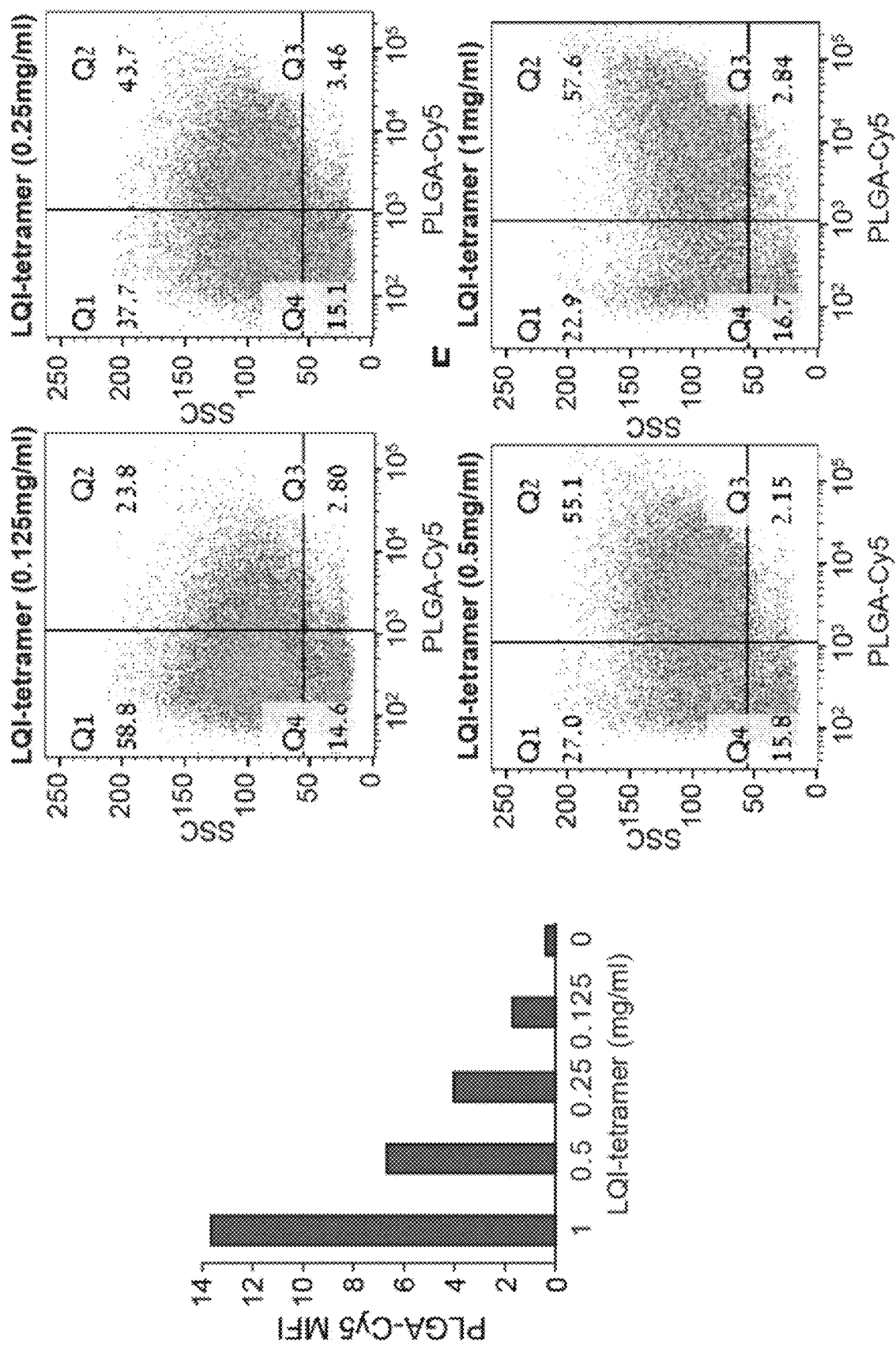

A biotinylated KFP-tetramer multiantigen (designated 16-KFP) was generated in the same manner as the 16-LQI. In whole blood, 16-KFP bound ~80% of human neutorophils and less than 10% of non-neutrophil WBC (FIG. 15A). The human 16-KFP had no significant effect on neutrophil activation (FIG. 15B), viability (FIG. 15C-D) or chemotactic properties (FIG. 15E-F).

Example 14

PLGA Nanoparticles Containing Therapeutics

Toward neutrophil specific drug delivery, it was postulated that decorating nanoparticles with the LQI-tetramer will render them neutrophil-specific. Two types of poly (lactic-co-glycolic acid) (PLGA) nanoparticles were generated:

1. SA-Coated PLGA Nanoparticles (NP):

NP synthesis was carried out by anchoring SA via a fatty acid tail to the PLGA particles, a strategy based on Park et al. (Journal of controlled release, 2011, 156(1), 109-115). Briefly, stearic acid (C-18 fatty acid) was activated in the carboxyl-group of the acid with EDC/NHS chemistry and was linked to the free amine groups present within SA. The fatty acid linked SA was added to the polymer mix during sonication when the polymer emulsion was created. The polymer emulsion was left overnight under stirring in a chemical hood to allow organic solvent evaporation and nanoparticle formation. SB-431542 (a TGFβ blocker) was encapsulated into PLGA nanoparticles during the synthesis process (see Methods). Due to its hydrophobic character, fatty acids anchor within the PLGA particles presenting the hydrophilic SA on their surface, thus enabling further conjugation with biotin-tagged peptide tetramer. The hydrodynamic diameter of the nanoparticles was 300 nm (+/−100) as measured by dynamic light scattering (DLS).

2. SA-Free PLGA Nanoparticles:

An additional LQI tetramer peptide, that is cysteine terminated at the C-terminus was designed as follows:

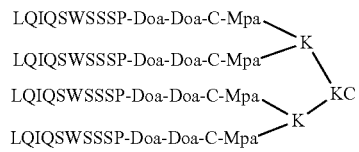

This tetrameric peptide can be conjugated to PLGA particles via the Cysteine (C) residue using a maleimide linker.

Figure 16F:
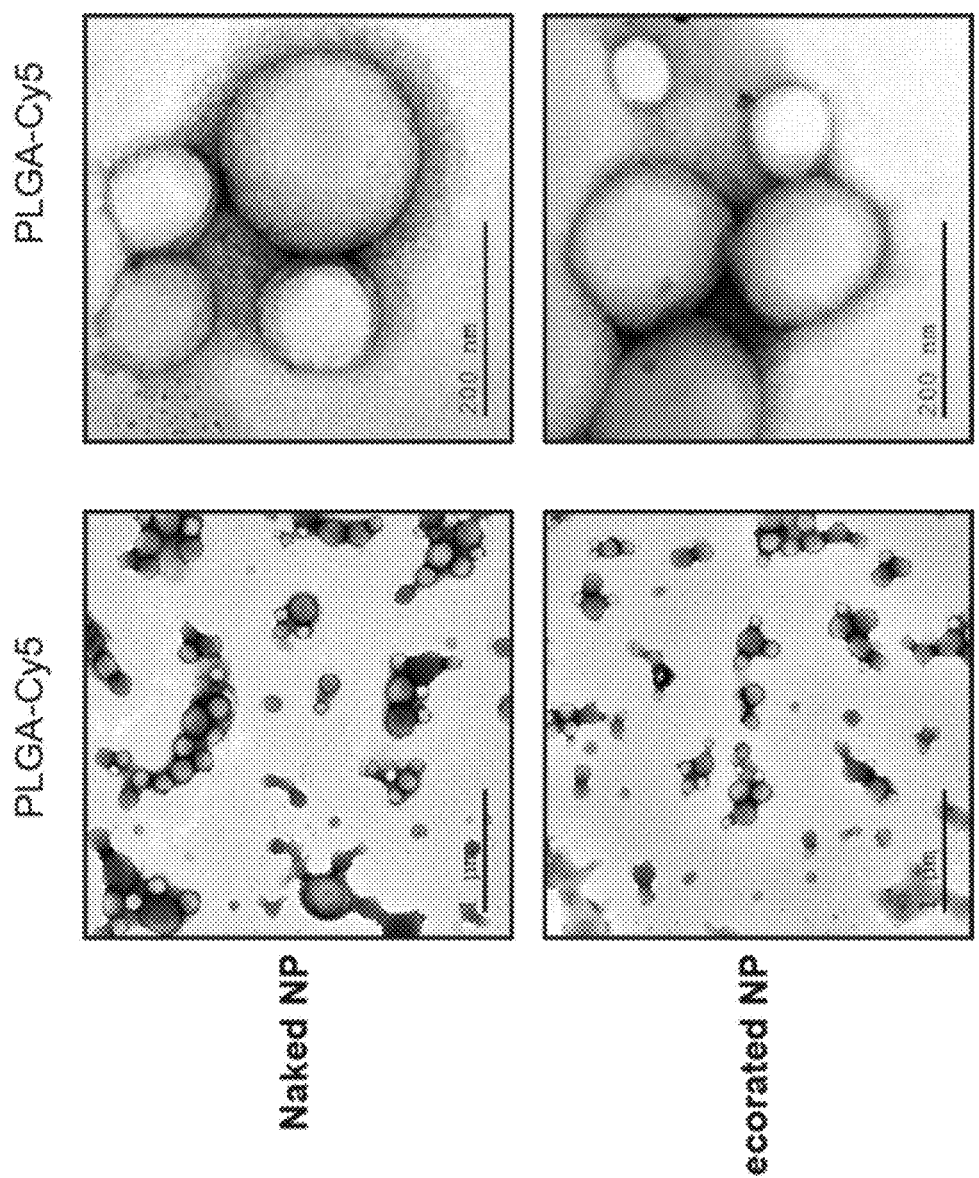

PLGA particles were prepared with polyethylene glycol (PEG) surface modification (see Methods) to increase in vivo circulation time and decrease uptake by macrophages. The fabricated PLGA nanoparticles (NP) contained PLGA-PEG-Maleimide (30%) and when PLGA-Cy5 (10%) was incorporated in the NP formulation detection of uptake nanoparticle could be monitored by flow cytometry. The most efficient NP formulation was found to be PLGA-PEG-Mal as it showed very high neutrophil uptake with minimal uptake by non-neutrophil WBCs (FIG. 16A-E). The hydrodynamic diameter of the nanoparticles was 300 nm (+/−100) as measured by dynamic light scattering (DLS) and importantly, using electron microscopy, there was no size difference observed between the LQI-tetramer coated and uncoated PLGA NP (FIG. 16F).

Figure 17A:
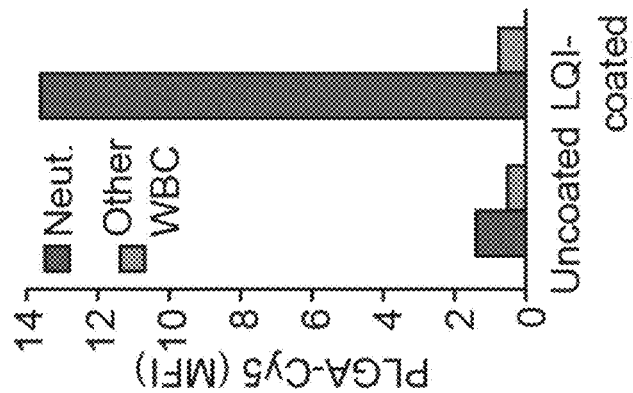
FIGS. 17A-E: NSNP Mediated Modulation of Neutrophil Function In Vitro and In vivo. (17A) Bar graph of representative quantification of uncoated or LQI-coated NP binding to neutrophils or other WBC. (17B) FACS dot plots showing uncoated (left) or LQI tetramer coated (right) Cy5-labelled PLGA NP binding to purified WBC. Cells with high side scatter (SSC) represent neutrophils. (17C) Bar chart showing % of neutrophils and other WBC binding to monomer-coated NP. (17D) Line graph showing PMA (50 nM) induced ROS production in control neutrophils (Cont.), neutrophils treated with empty (Empty NP) or DPI-containing NSNP (DPI NP) or with free DPI (Conc.). (17E) Bar graph summarizing FACS analysis of CD11b expression in neutrophils before (Cont.) or following PMA (100 nM) stimulation. Neutrophils were preincubated with vehicle, empty or Nexinhib-20 loaded LQI tetramer coated NP.
Figure 17B:
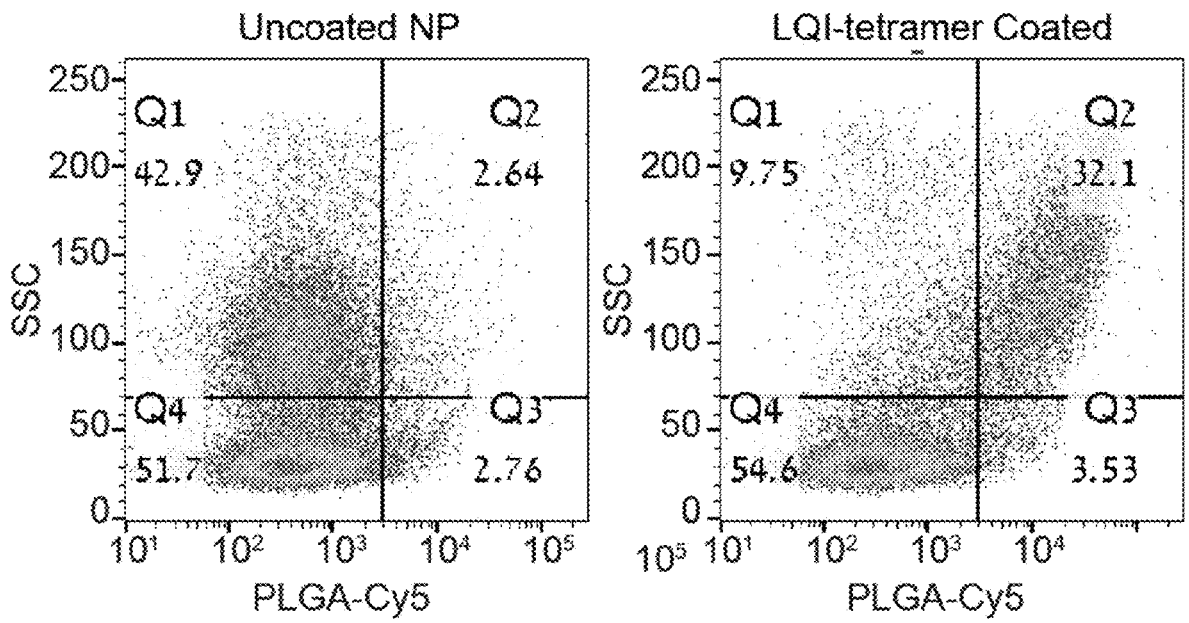
Figure 17C:
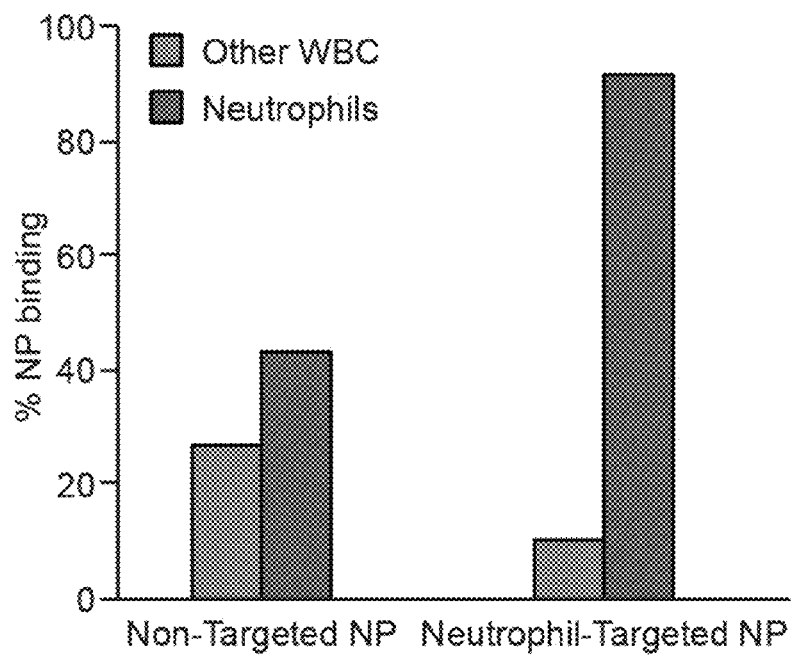

Indeed, decorating NPs with the LQI-tetramer conferred neutrophil specificity by simultaneously increasing the uptake by neutrophils and reducing the uptake by other cells (FIG. 17A-B). Similar results were observed when the nanosphere was coated with only LQI monomers (FIG. 17C). Using 3D reconstitution of confocal imagine, it was clearly shown that the LQI-tetramer decorated NPs are taken up by neutrophils.

Figure 17D:
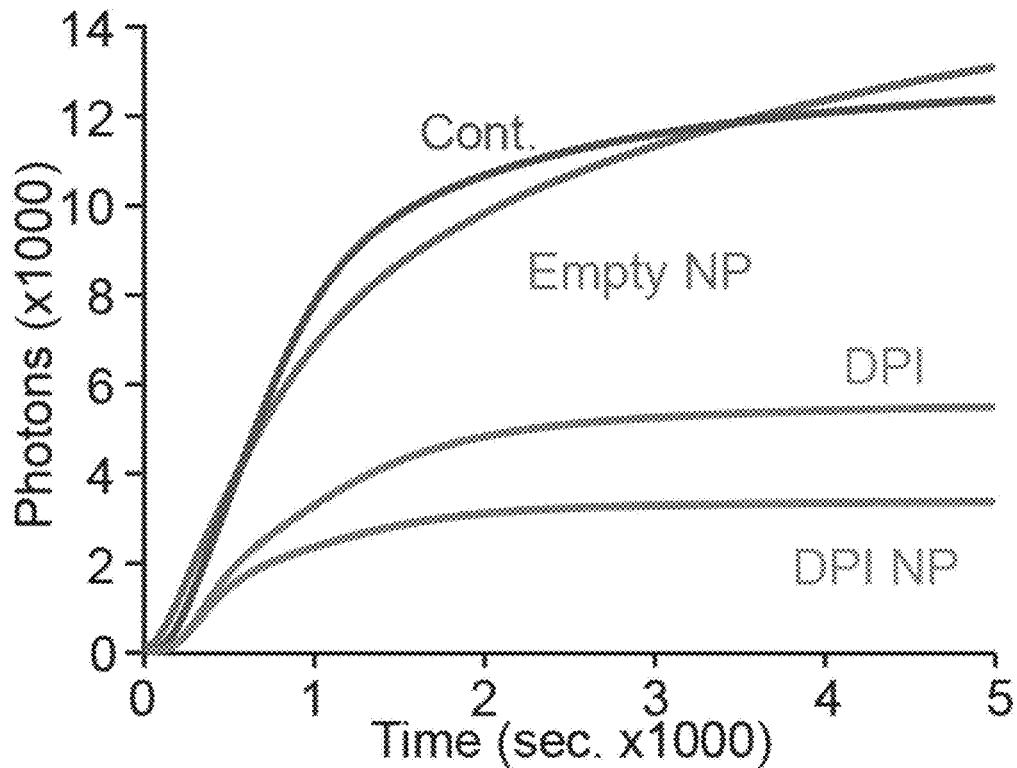

PLGA NPs are known to gradually degrade within the cell, releasing any encapsulated payload. Therefore, whether neutrophil degranulation ROS production could be modulated by encapsulating small molecule inhibitors within neutrophil specific NPs (NSNPs) was tested. Neutrophils generate ROS via the NADPH oxidase complex which is potently inhibited by Diphenyeneiodonium (DPI). DPI was loaded in the LQI-coated nanoparticles using a single emulsion encapsulation process. Then, neutrophils were pretreated for 3 hrs with 10 ul empty NP (Empty NP), 10 ul DPI-loaded NP (NP+DPI) or 1 uM free DPI. After one wash, neutrophils were stimulated with 50 nM PMA to induce ROS production. Positive control for PMA induction were neutrophils pretreated with vehicle (empty NP). Negative control (Cont.) were untreated neutrophils. Stimulating neutrophils with PMA dramatically increases ROS production (FIG. 17D). While addition of empty NSNPs had no effect on PMA stimulated ROS production, free DPI, and to a larger extend DPI-NSNPs, efficiently blocked the effect of PMA on ROS production (FIG. 17D).

Figure 17E:
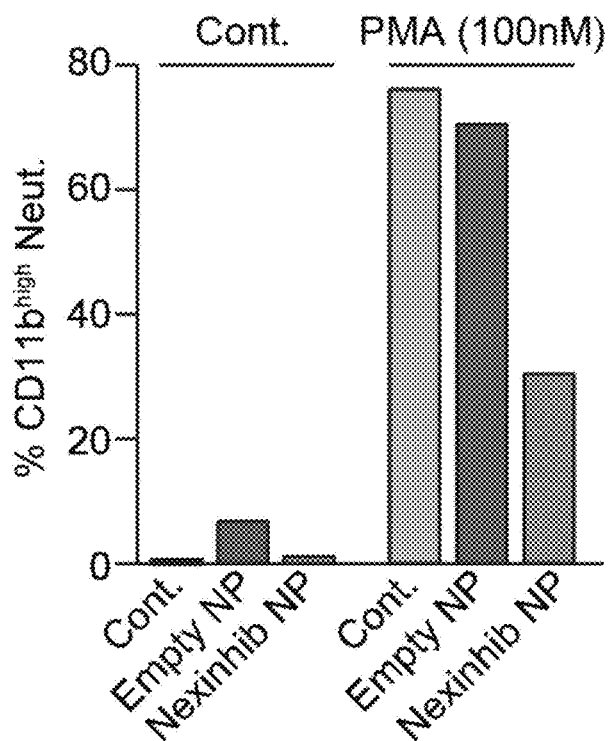

Using a similar strategy whether NSNPs may be used to block neutrophils' ability to degranulate was tested. This process can be inhibited by Nexinhib-20. Following PMA stimulation neutrophil degranulate, as measured by an increase in CD11b surface expression. This process is completely blocked when neutrophils are pre-treated with Nexinhib-20 containing NSNPs (FIG. 17E). Together, these observations demonstrate both the efficacy and specificity of using NSNPs to specifically manipulate ROS production and degranulation, processes critical for inflammation.

Figure 18A:
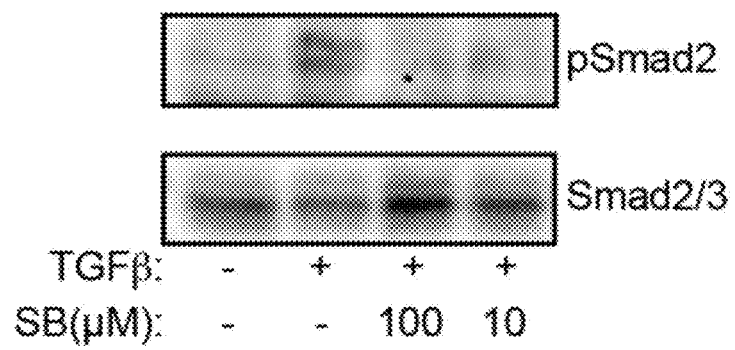
FIGS. 18A-G: (18A-B) Micrographs shows western blot analysis detecting total Smad2/3 and phopho-Smad2 in HDNs that were (18A) preincubated with empty NP+TGFβ, or SB431542 NP+TGFβ before adding TGFβ or (18B) incubated with TGFβ only (control), empty NP+TGFβ, or SB431542 NP+TGFβ. (18C) Bar graph showing SB431542-containing NSNP limit the propagation of circulating low density neutrophils in 4T1 tumor bearing mice, indicating effective blocking of TGFβ in vivo. Control mice (Cont.) were untreated and mice treated with empty NSNP (Empty NP) served as control for NSNP injection. (18D-E) Dot plots of (18D) neutrophils (Ly6G+) and (18E) non-neutrophil WBC (Ly6G−) isolated from 4T1-tumor bearing mice were incubated with empty NP, roscovitine-loaded NP or free Roscovitine. Subsequently cells were analysed for Annexin-V binding to quantify apoptotic cells. (18F) Bar graph of the effect of empty or roscovitine-containing NSNP on neutrophil numbers 4 hrs following NP administration. (18G) Line graph showing the effect on $H_2O_2$ production by PMA stimulated peritoneal neutrophils produced by of free DPI, empty NSNPs, or DPI containing NSNPs administered intravenously.
Figure 18B:
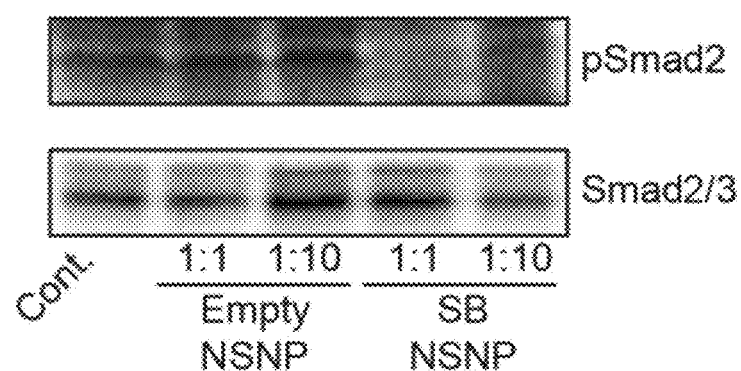
Figure 18C:
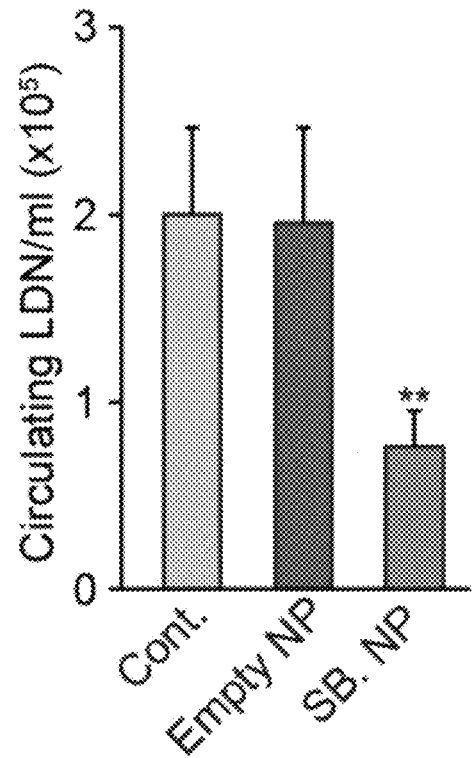

To examine the effect of SB-431542 containing PLGA nanoparticles on TGFβ signaling in murine neutrophils, $5 \times 10^6$ HDNs isolated form 4T1 tumor bearing mice were pre-incubated for 4 hours in 100 µl of 10% FCS/RPMI with 6 µg/l empty PEG-modified PLGA nanoparticles (NP), 0.6 µg/l empty NP (1:10), 6 µg/l SB431542 NP or 0.6 µg/l SB431542 NP (1:10). Following incubation, the neutrophils were thoroughly washed to remove any unbound nanoparticles, and then incubated for 30 min in the presence or absence of TGFβ (10 ng/l) in order to induce Smad2 phosphorylation. After treatment, cells were lysed in 40 µl lysis buffer and prepared for western blot to detect total Smad2/3 and phopho-Smad2. As presented in FIG. 18A, while empty nanoparticles had no effect on TGFβ-induced phosphorylation of Smad2, SB431542 containing nanoparticles completely blocked TGFβ signaling. Notably, 1:10 dilution of the SB431542 containing nanoparticles still blocked TGFβ signaling in neutrophil suggesting that lower nanoparticle concentrations may also be effective. A similar result was observed when neutrophils were simultaneously exposed to the SB431542 NPs and TGFβ (FIG. 18B). Mice bearing 4T1 tumors were also administered the SB431542-containing NSNPs and it was found that the propagation of circulating low density neutrophils was reduced (FIG. 18C).

Figure 18D:
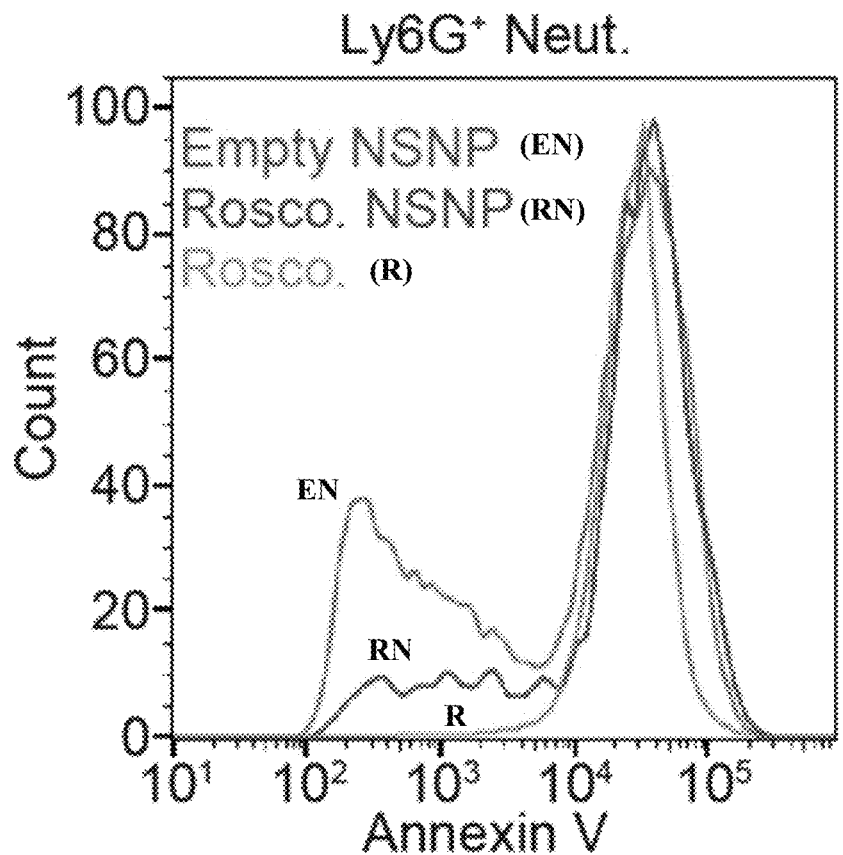
Figure 18E:
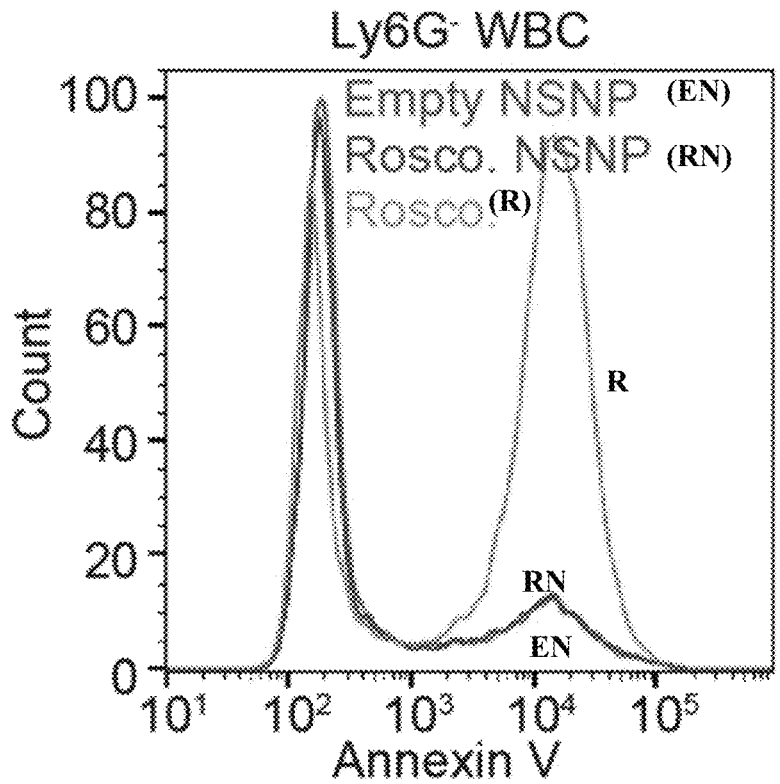
Figure 18F:
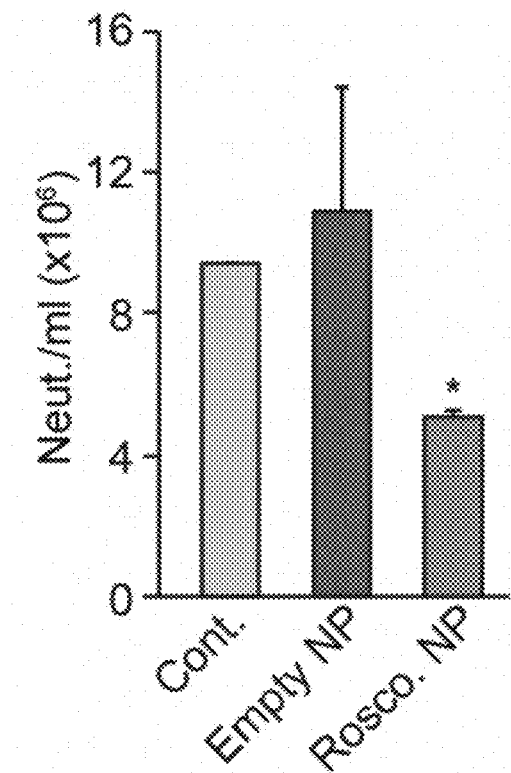

Roscovitine is another therapeutic molecule that works similarly to SB431542. It was found that NSNPs encapsulating Roscovitine also induced neutrophil specific cell death as measured both by flow cytometry (FIG. 18D-E) and microscopy (FIG. 18F).

Figure 18G:
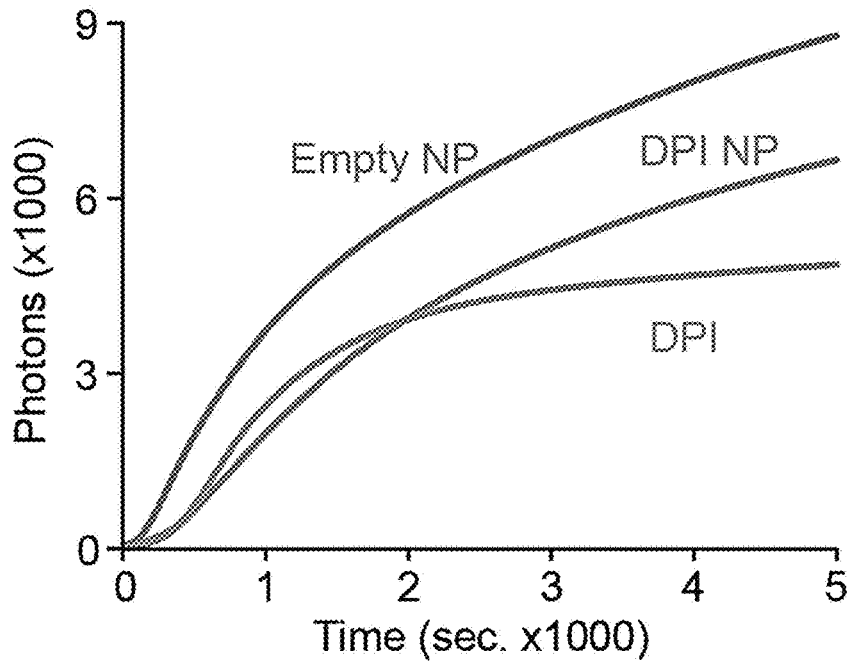

Next, it was tested whether NSNPs loaded with other small molecules can modify neutrophil function in vivo. It was found that DPI containing NSNPs administered in vivo significantly reduce PMA induced ROS production (FIG. 18G).

To examine the effect of SB-431542 containing PLGA nanoparticles on TGFβ signaling in human neutrophils, nanoparticles containing SB431542 are coated with the human peptide KFP (KFPDLDSRRLPHMSL, SEQ ID NO: 1) by coupling KFP-SH tetramer according to the structure below, to PEG-modified PLGA nanoparticles containing SB431542 (see Methods).

KFP-SH tetramer structure:

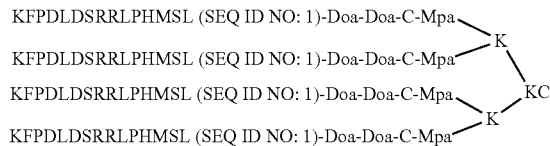

Human neutrophils are then treated according to the following treatment groups:
1. No treatment
2. Incubation with empty (without SB431542) peptide-coated nanoparticles
3. Incubation with SB431542-containing peptide-coated nanoparticles
4. Incubation with SB431542-containing nanoparticles without peptide
5. Incubation with empty nanoparticles without peptide Following incubation, the five treatment groups are thoroughly washed to remove any unbound nanoparticles, and then incubated for 30 min, 1 hour, 2 hours or 4 hours in the presence or absence of TGFβ (10 ng/l) in order to activate the TGFβ signaling pathway. After treatment, cells are lysed in 40 µl lysis buffer and prepared for western blot to detect total Smad2/3 and phopho-Smad2. The optimal time point and the amount of nanoparticles necessary to inhibit TGFβ signaling are determined.

Example 15

Biodistribution of LQI-PLGA Nanoparticles

Figure 19A:
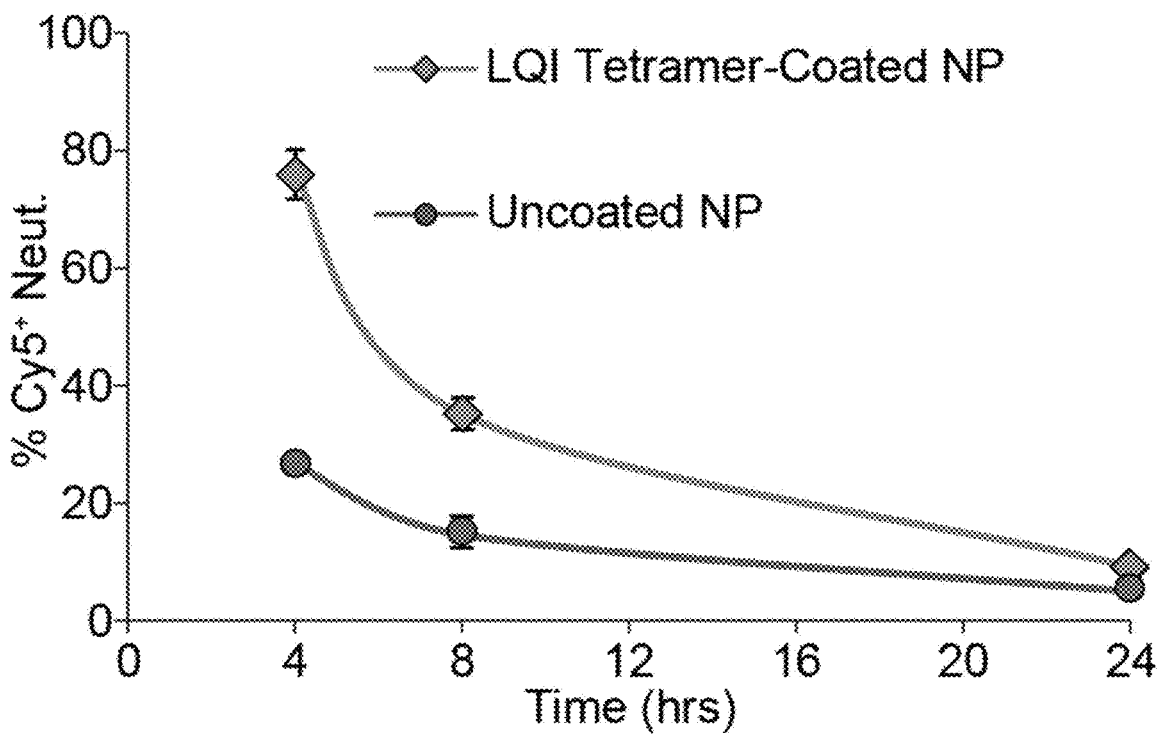
FIGS. 19A-E: NSNP distribution in vivo. (19A) Line graph quantifying NP containing neutrophils in healthy Balb/C mice intravenously injected with either uncoated or LQI-tetramer coated NP, 4, 8, and 24 hours after injection. (19B) Typhoon™ biodistribution imaging in healthy Balb/C mice 3 hours following i.v. injection of either LQI tetramer coated empty NP, uncoated empty NP or PBS as control. (19C) Fluorescent staining of a neutrophils (green) carrying fluorescent nanobeads (red) within a blood vessel (dashed lines). (19D) Representative Typhoon™ imaging of colons from healthy mice (left) and mice with DSS-induced colitis (right). (19E) Representative fluorescent imaging of NSNP accumulating in an inflamed focus in colon from mouse with DSS-induced colitis.
Figure 19B:
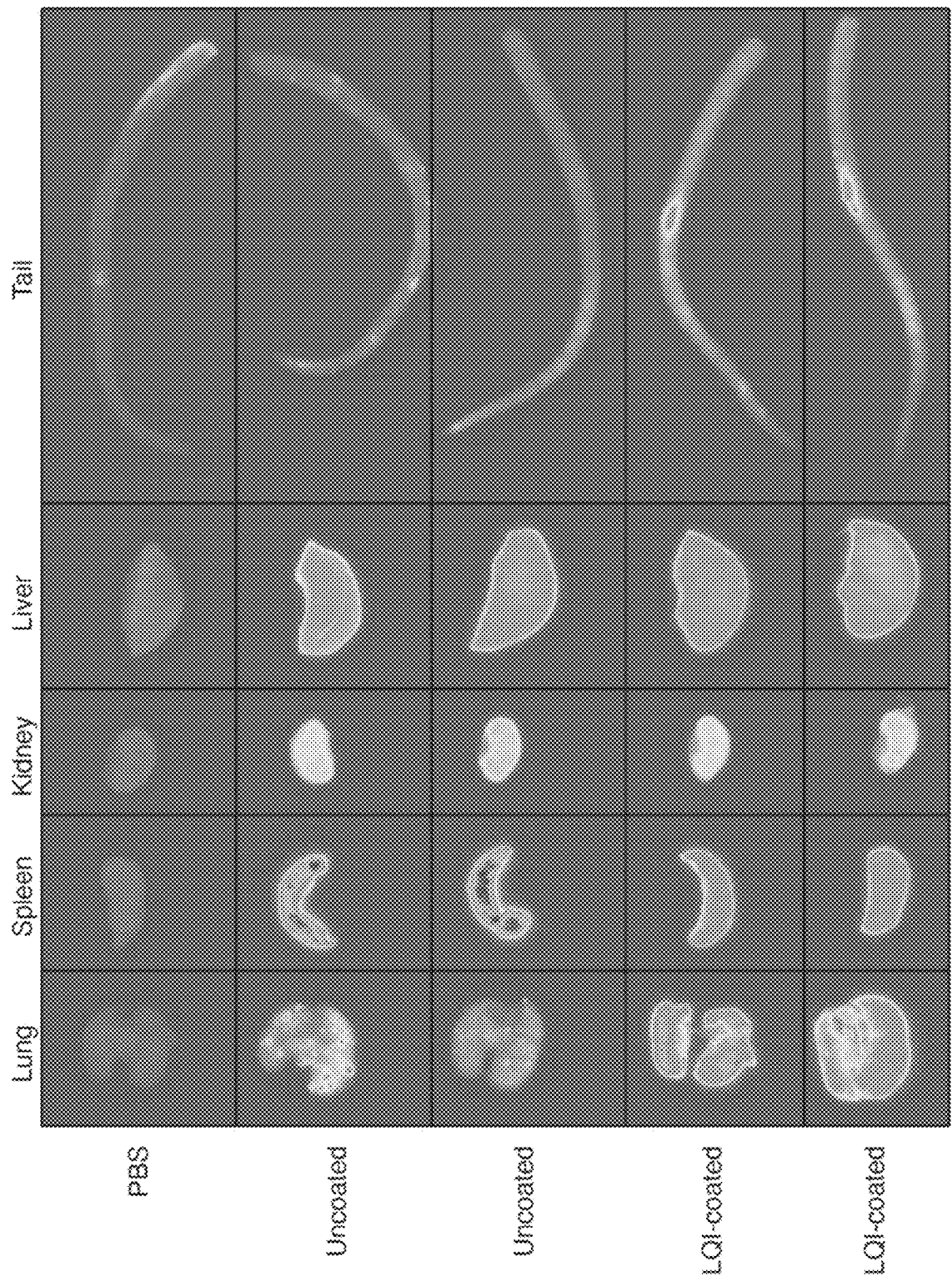
Figure 19D:
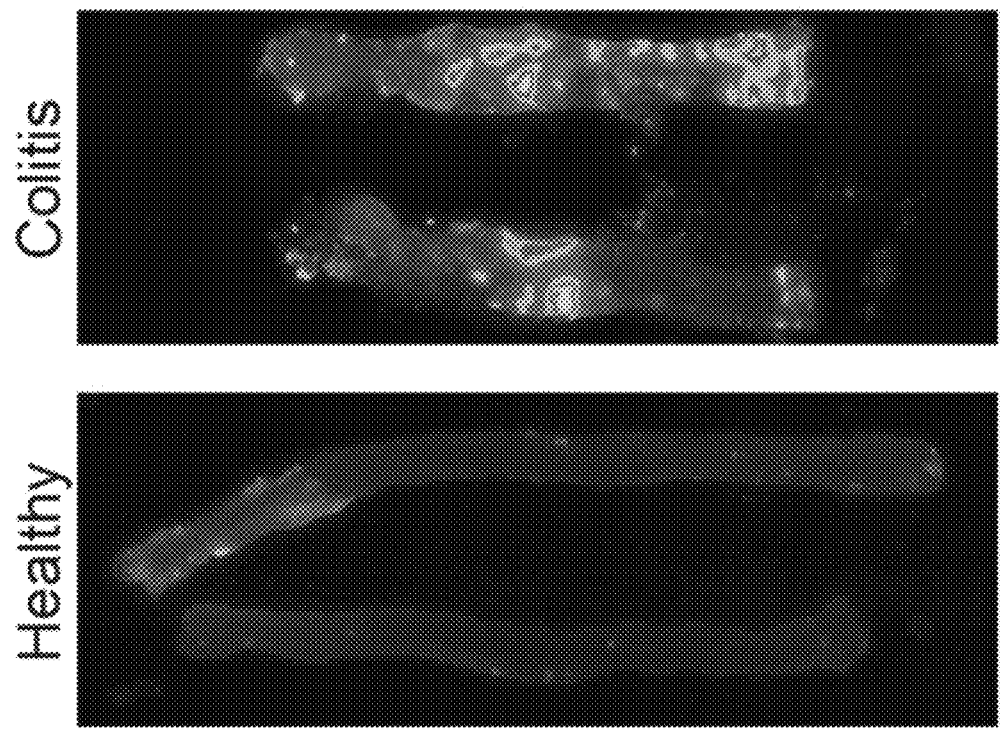
Figure 19C:
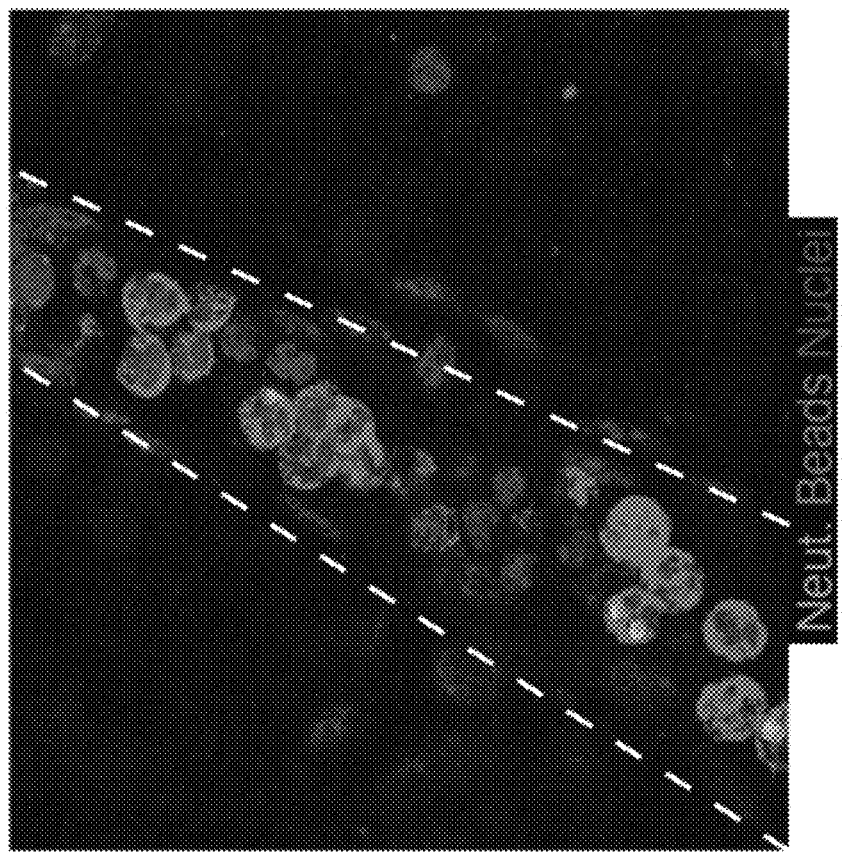
Figure 19E:
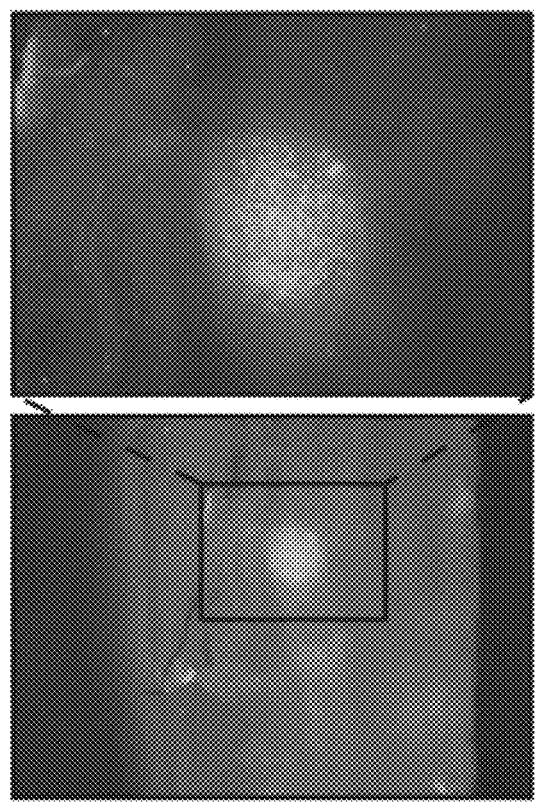

It was noticed that 4 hours following intravenous (i.v.) administration, 60-80% of circulating neutrophils carry the NSNPs whereas fewer than 30% of circulating neutrophils carry the naked NP (FIG. 19A). The NSNPs are rapidly cleared from the circulation with a half-life of approximately 4 hours (FIG. 19A). The biodistribution of NSNP was then analyzed using Typhoon™ and it was found that splenic accumulation was dramatically higher when using uncoated NP, whereas the accumulation of NPs in the lungs was significantly higher when using LQI-tetramer decorated NP (FIG. 19B). Strikingly we noticed that the site of i.v. injection in the tail shows accumulation of LQI-tetramer decorated NP but not of uncoated NP (FIG. 19B) suggesting that NSNPs are taken up by circulating neutrophils and carried with them to the site of inflammation. To further examine this possibility, the DSS-induced mouse model of colitis was used and found that NSNP are taken up by circulating neutrophils (FIG. 19C) and accumulate in inflammatory foci within the colon of mice with colitis but not in the colon of healthy mice (FIG. 19D-E).

Example 16

LQI-PLGA Nanoparticle Treatment of COPD

Figure 20A:
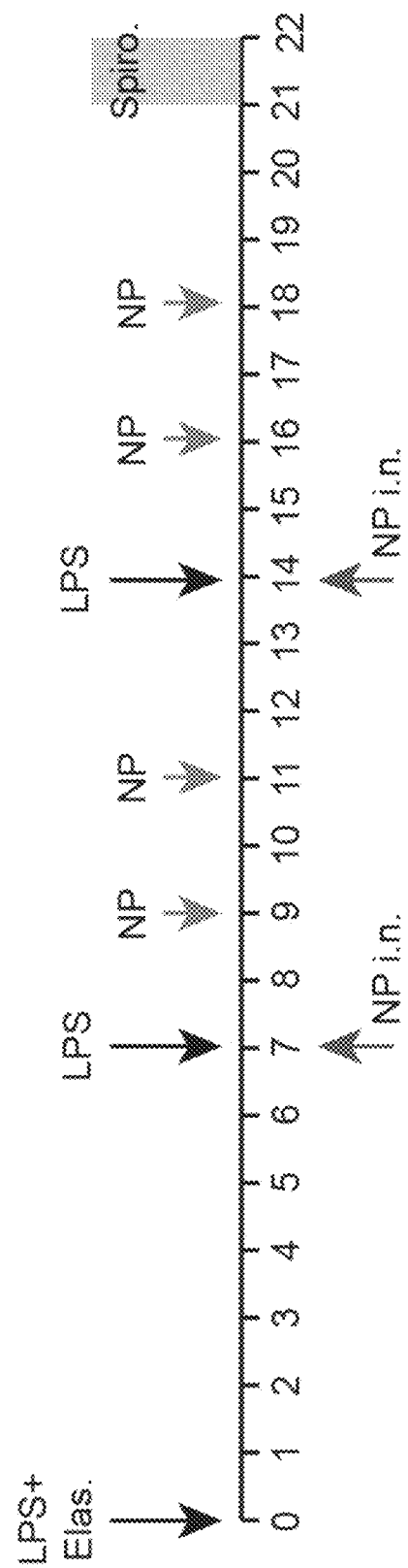
Figure 20B:
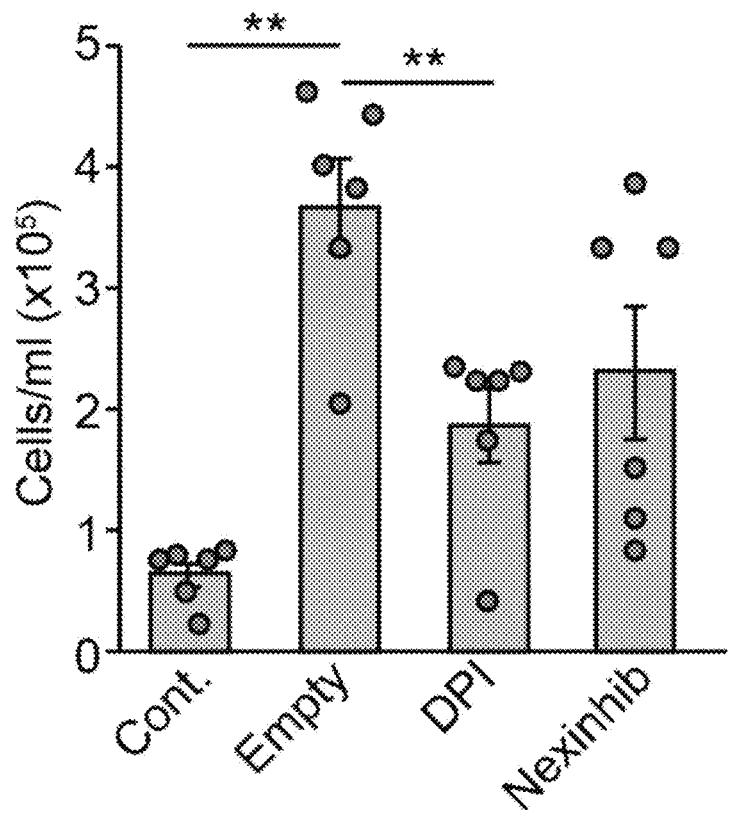
Figure 20C:
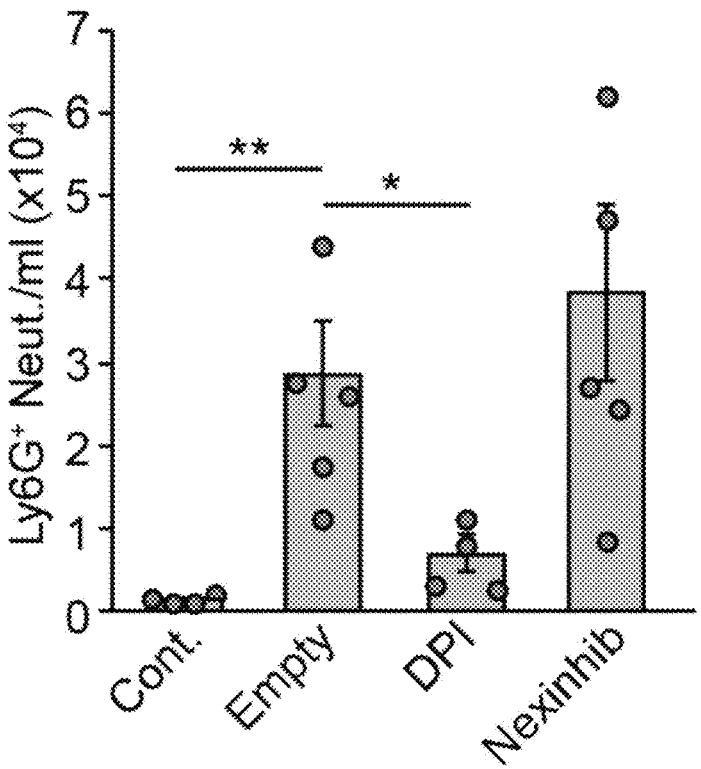
Figure 20D:
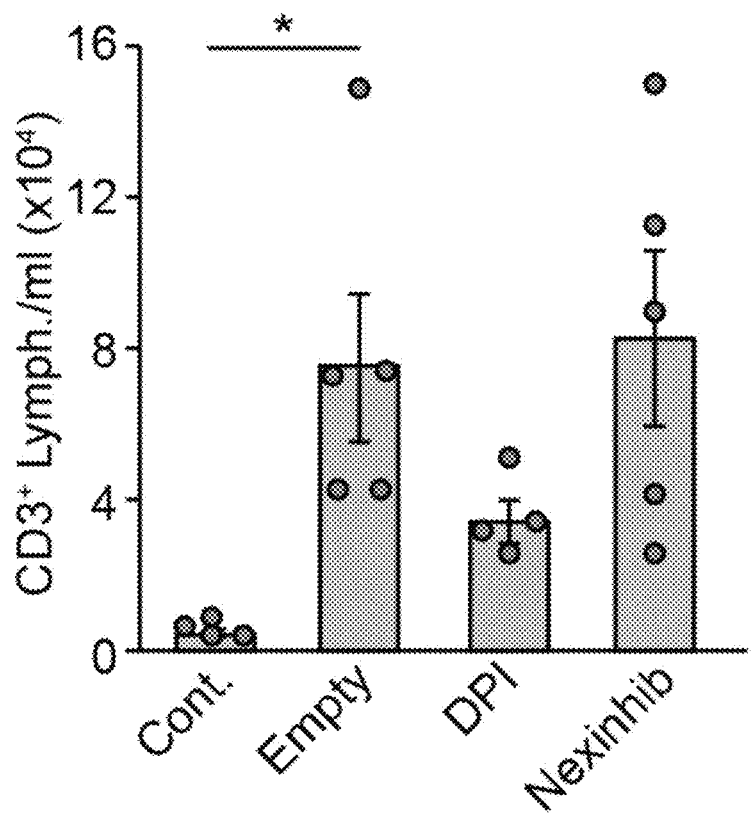
Figure 20E:
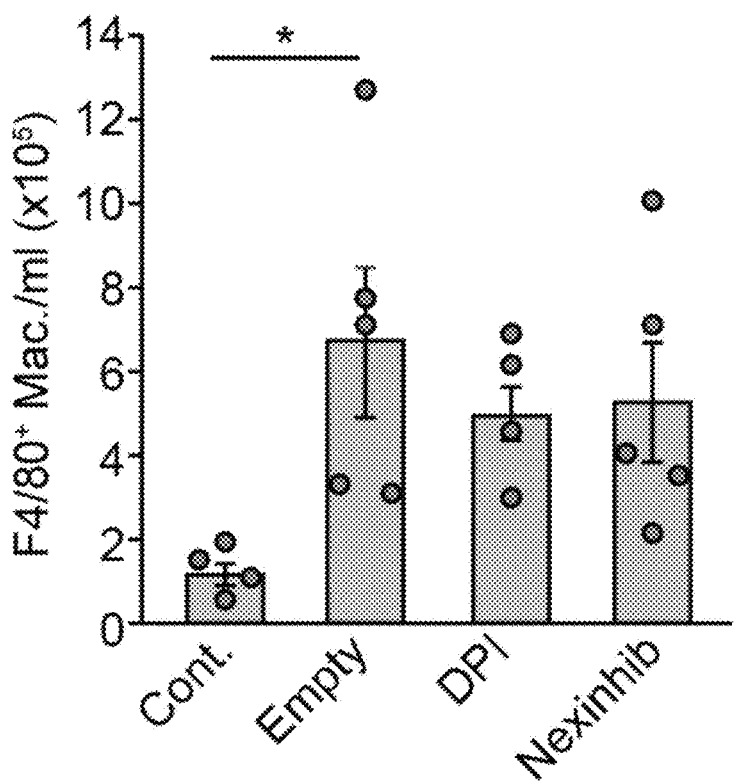
Figure 20F:
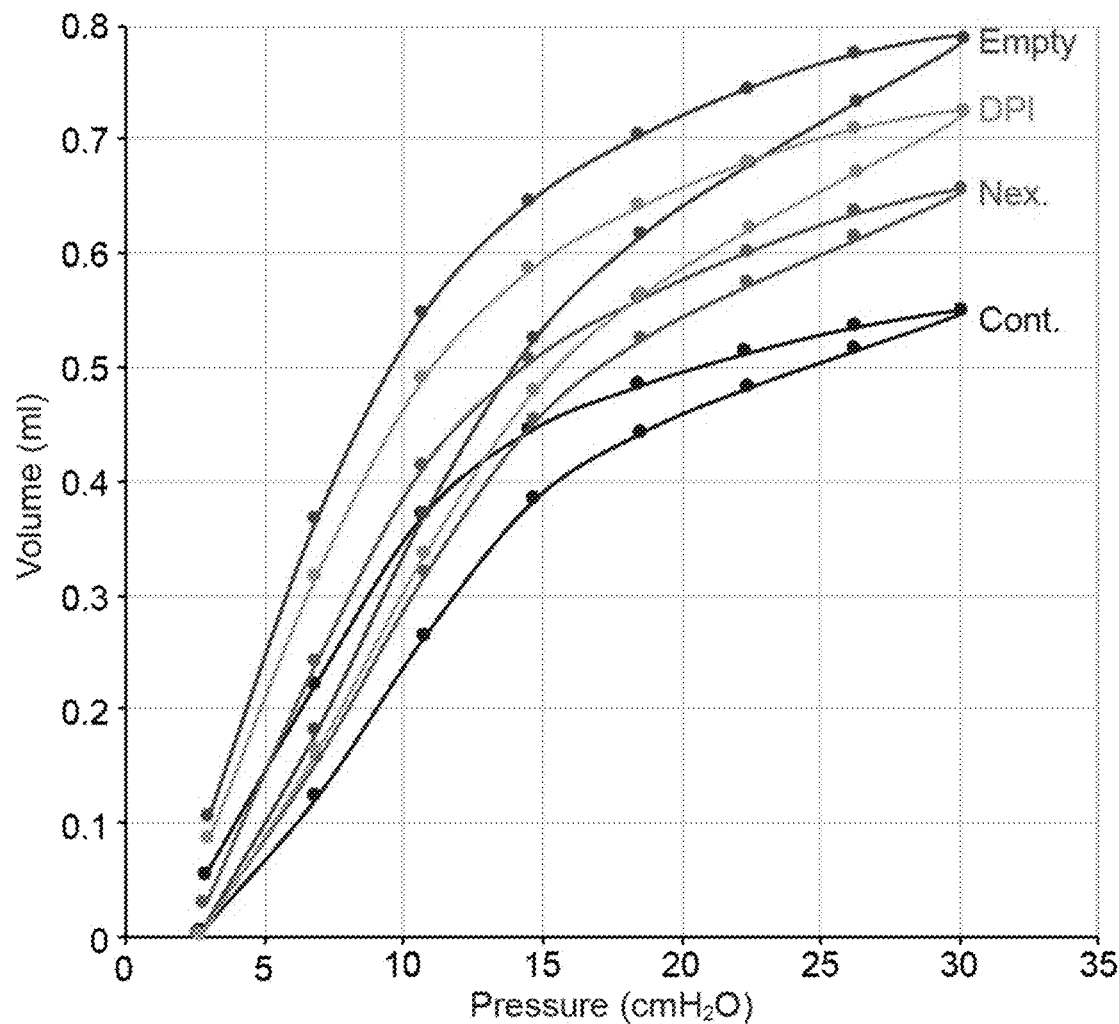
Figure 20G:
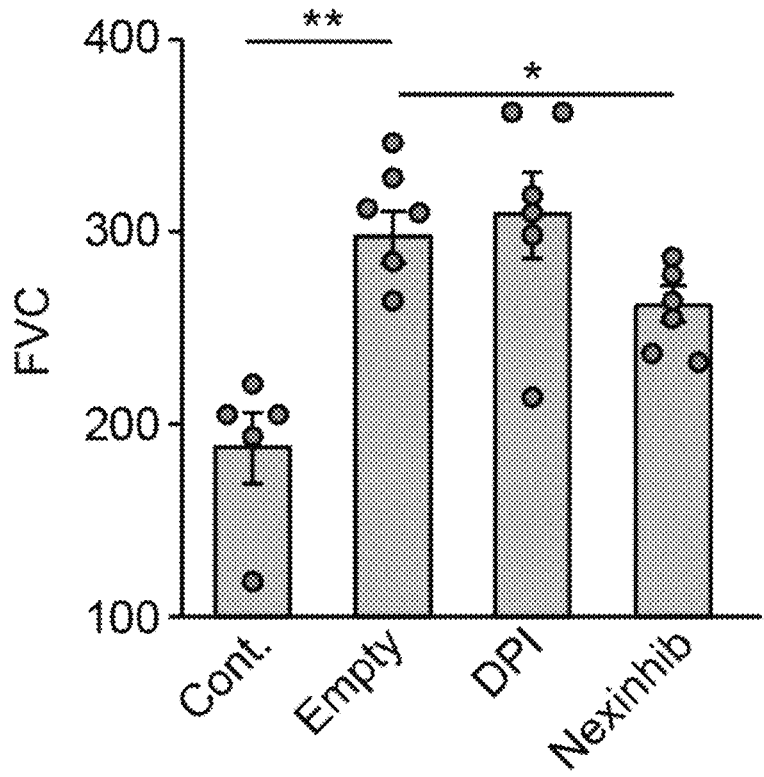
Figure 20H:
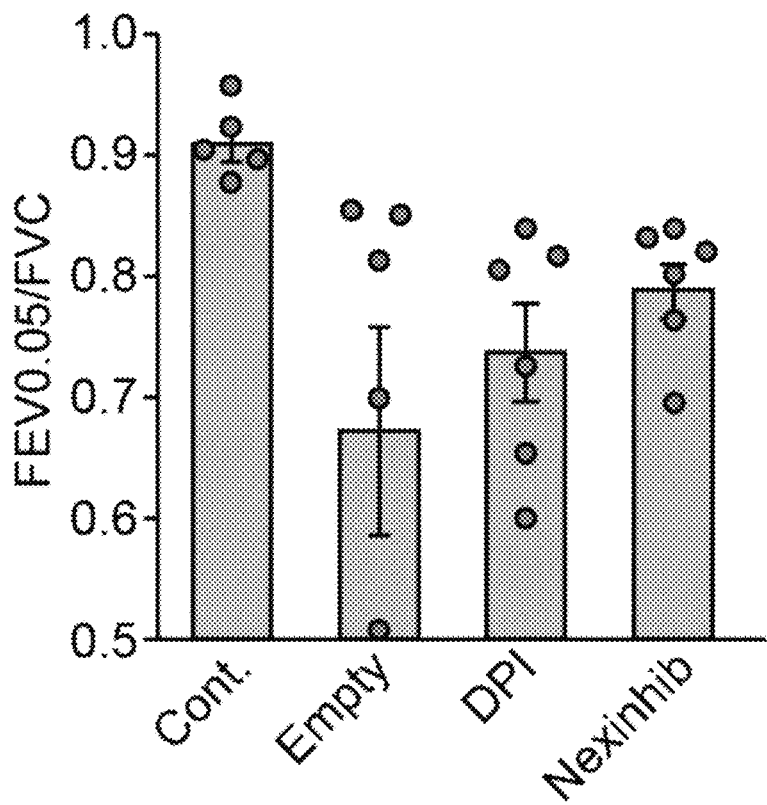
Figure 20I:
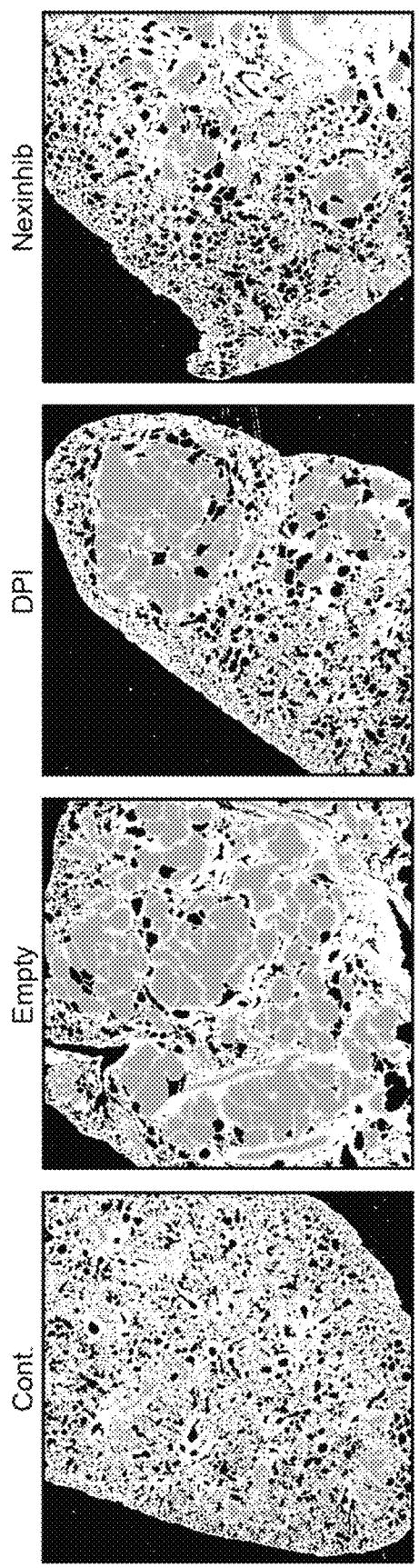
Figure 20K:
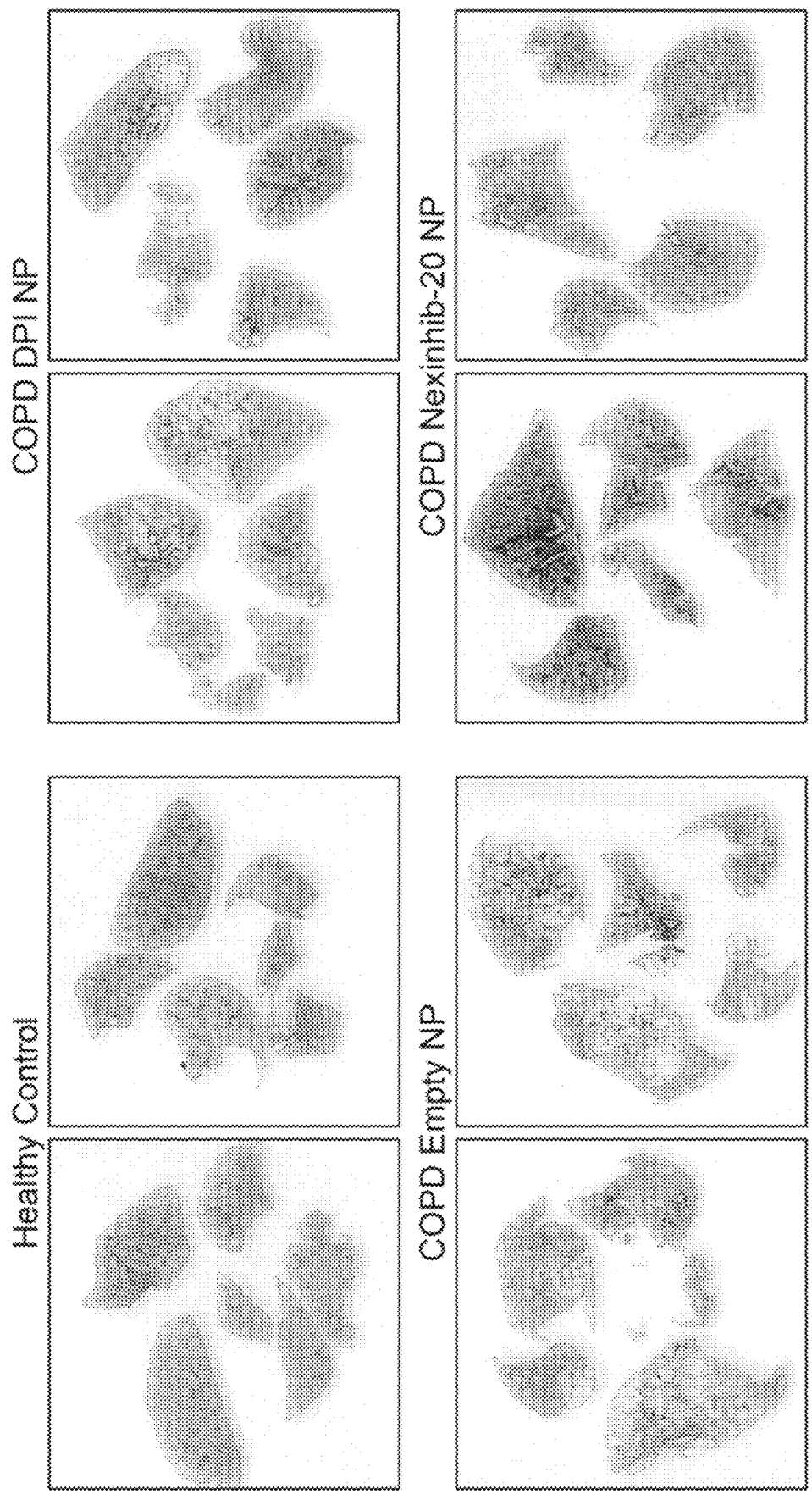

Finally, it was tested whether NSNPs targeting either ROS production (DPI) and degranulation (Nexinhib-20) may be used therapeutically in a mouse model of chronic obstructive pulmonary disease (COPD) (FIG. 20A). It was found that DPI-NSNPs, and to a lesser extent Nexinhib-20-NSNPs reduced the overall bronchoalveolar lavage fluid (BALF) cellularity indicating a reduced state of inflammation (FIG. 20B). DPI-NSNPs reduced BALF neutrophils and T-cells but had no significant effect on macrophage numbers. On the other hand, Nexinhib-20-NSNPs did not affect any of these cell populations (FIG. 20C-E). The most important physiological indication for COPD severity is expressed in spirometry, where a dramatic increase in P/V ratio is observed when comparing healthy mice (Cont.) to COPD mice treated with empty NSNP (FIG. 20F). Treating the mice with Nexinhib-20-NSNPs dramatically reduced the physiologic severity of COPD, whereas DPI-NSNPs had a significant albeit lesser effect (FIG. 20F). The effect of Nexinhib-20-NSNPs was observed to be more robust than that of DPI-NSNPs and this was also reflected in other respiratory parameters such as FVC (FIG. 20G) and FEV0.05/FVC (FIG. 20H) where Nexinhib-20 outperforms DPI. The robust beneficial effect of using DPI and Nexinhib-20-NSNPs to treat mice with COPD is clearly visible histologically. Lungs from mice treated with DPI and Nexinhib-20 show a dramatic reduction in emphysema (FIG. 20I-K).

Example 17

Uptake of KFP-PLGA Nanoparticles by Human Neutrophils $5 \times 10^6$ white blood cells (WBC) or 25 µl of whole blood are isolated from a blood healthy donor and are incubated with different volumes of KFP-PLGA NPs (see Example 14) at room temperature under motion. Different amounts of nanoparticles are added to the cells for 30 min. After 30 min, the cells are washed and stained with antibodies against CD45, CD66b and CD177 to identify WBC and neutrophils. By flow cytometry analysis the percentages of nanoparticle-positive populations are determined. The amount of nanoparticles that gives the best ratio of neutrophil to non-neutrophil targeting is determined. Furthermore, the incubated cells are fixed with 1.6% PFA and transferred to a microscope slide using cytospin. Cells are covered with DAPI-containing mounting medium and imaged using confocal microscopy.

The blood of several healthy donors is analyzed for the expression of CD177 and the extent of nanoparticles uptake, with the calibrated nanoparticle amount determined before.

Example 18

Effect of KFP-PLGA Nanoparticles on Neutrophil Survival and Function

In order to assess the functional consequences of exposing human neutrophils to the KFP-decorated nanoparticles (see example 13), human neutrophils are purified from the blood of several healthy donors by density gradient centrifugation. The consequences on neutrophil survival, migration, phagocytic activity, activation and ROS production are then assessed. In these assays, the following treatment groups are compared:
1. No treatment
2. Incubation with empty (without SB431542) peptide-coated nanoparticles
3. Incubation with SB431542-containing peptide-coated nanoparticles
4. Incubation with SB431542-containing nanoparticles without peptide
5. Incubation with empty nanoparticles without peptide To investigate the effect of PLGA-degradation within the cells, the following functional assays are conducted at least for two different time points—1 hour and 4 hours after incubation with the nanoparticles.

Survival

The five treatment groups of neutrophils are incubated in OptiMEM 0.5% FCS for 2 or 6 hours. Live neutrophils are then counted based on trypan dye exclusion.

Furthermore, a FACS analysis of Annexin V+ (apoptotic) and PI+ (dying/dead) neutrophils is conducted. Different incubation times (1 hour, 2 hours, 4 hours, 6 hours) are analyzed.

Migration

To test the impact of the different nanoparticles on neutrophil migration, the effect in a Boyden chamber was tested. Neutrophils incubated with nanoparticles (1 hour, 4 hours) are added to the upper compartment of the transwell whereas CXCL2, a known chemoattractant, is placed in the lower chamber. The migration of neutrophils is quantified after one hour by taking five pictures per well and counting of the migrated cells.

Phagocytosis

Neutrophil phagocytic activity is determined using the Phagocytosis Assay Kit (Cayman Chemical) according to the manufacturer's instructions. In brief, neutrophils of the different treatment groups are diluted in phagocytosis buffer to which FITC-labeled beads are added and incubated for 2 hours at 37° C. The extent of phagocytosis is determined using FACS analysis.

Neutrophil Activation

The expression of the integrin CD11b is a proxy for neutrophil activation. The five neutrophil treatment groups are analyzed for their CD11b surface expression after 1, 2, 4 and 6 hours of incubation with the nanoparticles.

ROS Production

Using a luminol-based assay the extent of ROS production in the five treatment groups is determined at 2 time-points (1 hour, 4 hours). Each treatment group is analyzed in its resting state and when stimulated with phorbol 12-myristate 13-acetate (PMA), a well-described molecule that stimulates production of reactive oxygen species (ROS).

Example 19

Identification of CD177 as a Peptide-Binding Partner of the Neutrophil-Binding Peptides Pulldown of Ligand Next, the binding partner of the LQI peptide on the neutrophil surface was identified. The biotinylated LQI-tetramer was bound to streptavidin-agarose beads and incubated with neutrophil lysate for 3 h. After washing, the bound proteins were eluted by incubating the beads for 10 min at 95° C. in protein sample buffer containing beta-mercaptoethanol. The gel was stained using silver staining. Lanes of the eluates of peptide- and control-beads were cut out and analyzed by mass spectrometry.

Ligand Identification

Figures 21A, 21B:
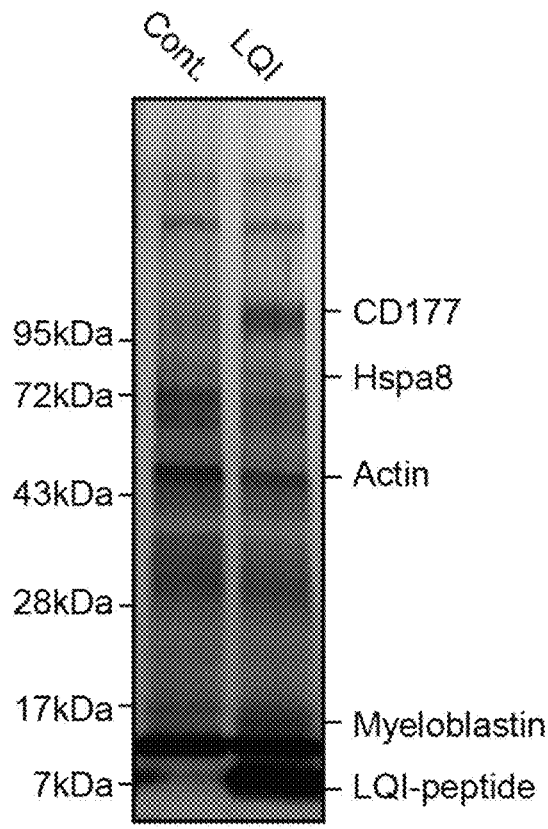
FIGS. 21A-G: (21A) Micrograph sliver staining of a protein gel showing pulldown of the LQI-peptide ligand CD177 using immobilized 16-LQI on neutrophil lysate. (21B) Table of top-ranking proteins enriched by 16-LQI pull-down. (21C-D) Representative dot plots of isolated WBC stained with (21C) Ly6G and CD177 or (21D) CD177 and 16-LQI. (21E) Dot plot of FACS analysis of 16-LQI binding to control HEK293T cells (Red), SA-Cy3 binding to HEK293T cells overexpressing the murine CD177 protein (Green) and CD177-overexpressing HEK293T cells were incubated with 16-LQI (blue). (21F) Representative STORM imaging of a single neutrophil with staining of CD177 (green) and 16-LQI (red), overlay with brightfield (left) or DAPI staining of nucleus (right). (21G) Quantification of CD177 and 16-LQI interaction for image depicted in (E) using the ImageJ Interaction Factor plugin.
Figure 21C:
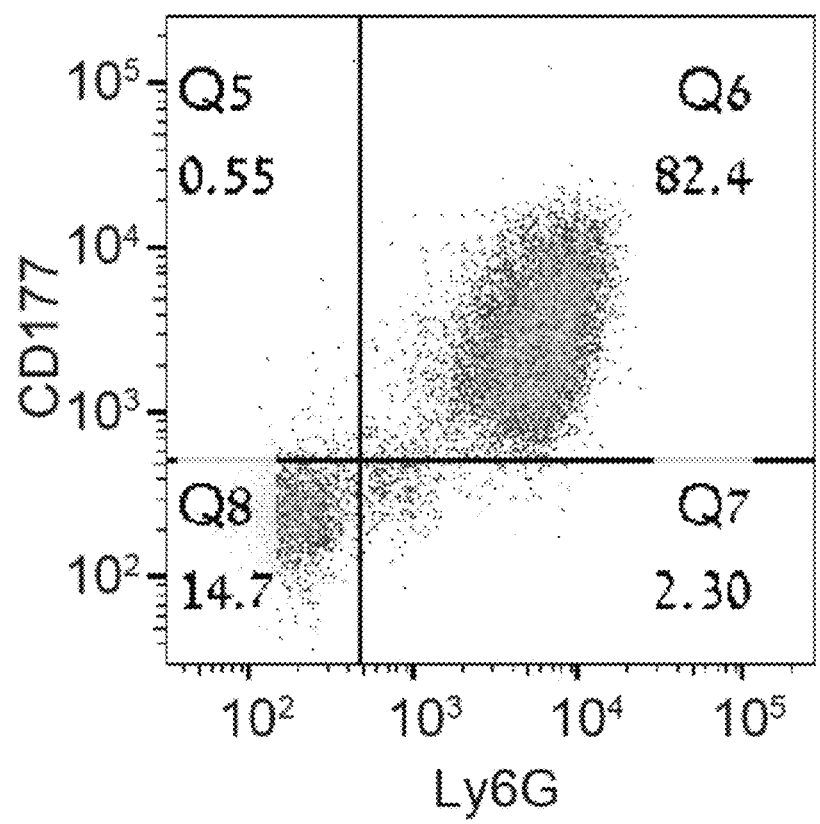
Figure 21D:
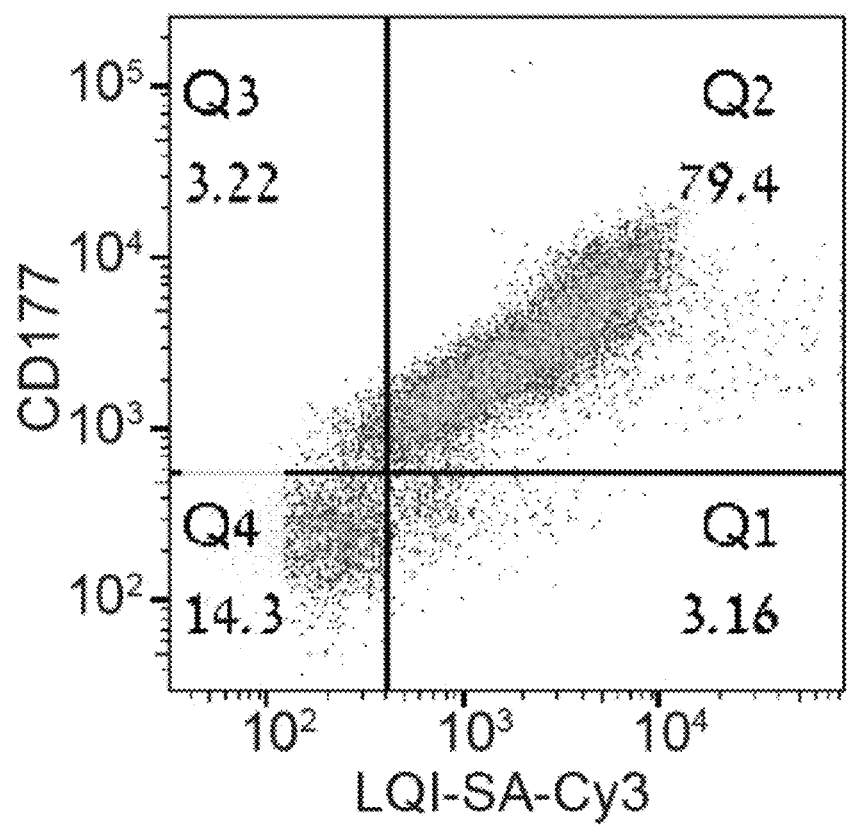
Figure 21E:
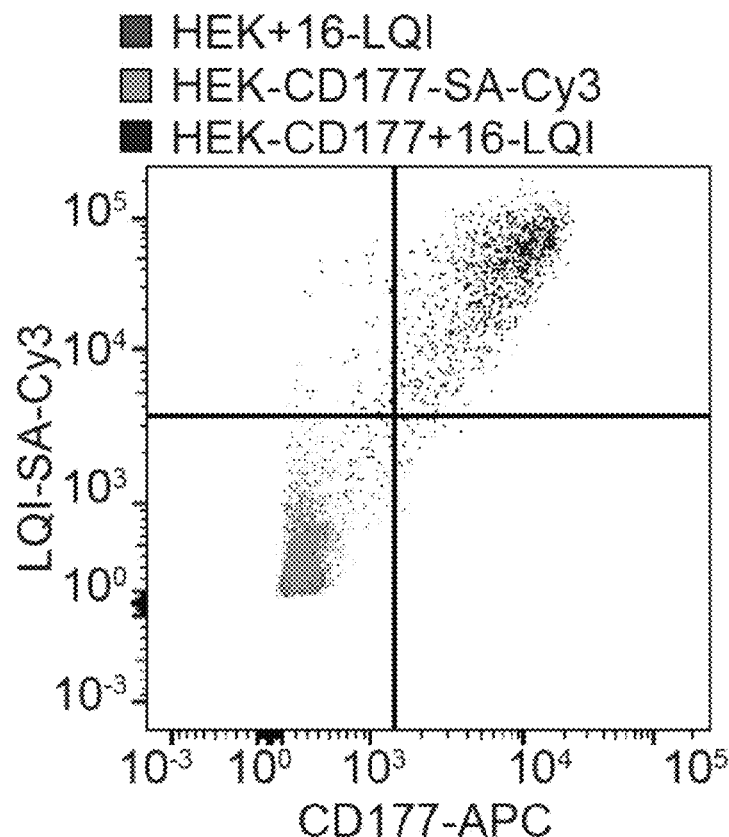
Figure 21F:
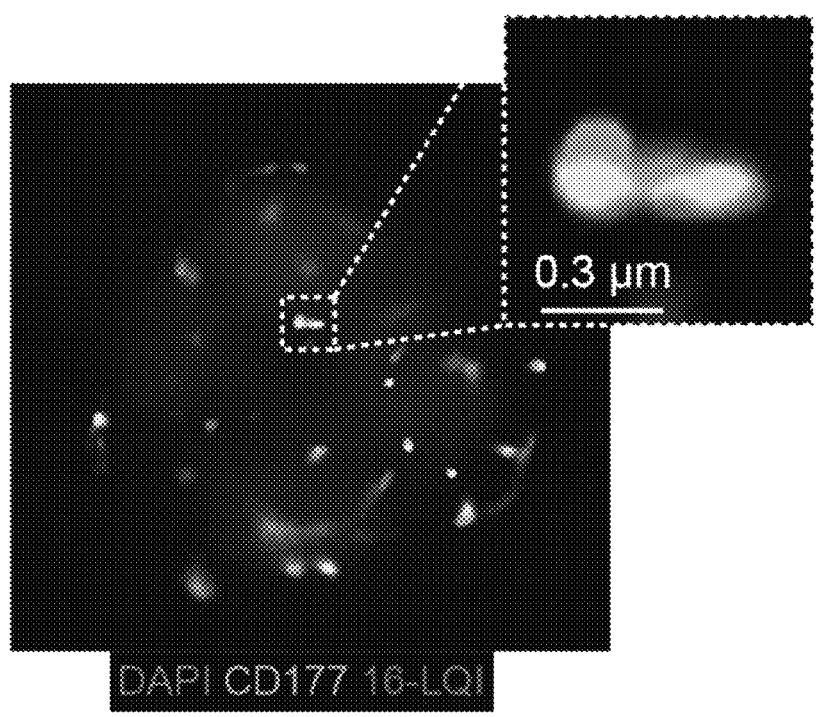
Figure 21G:
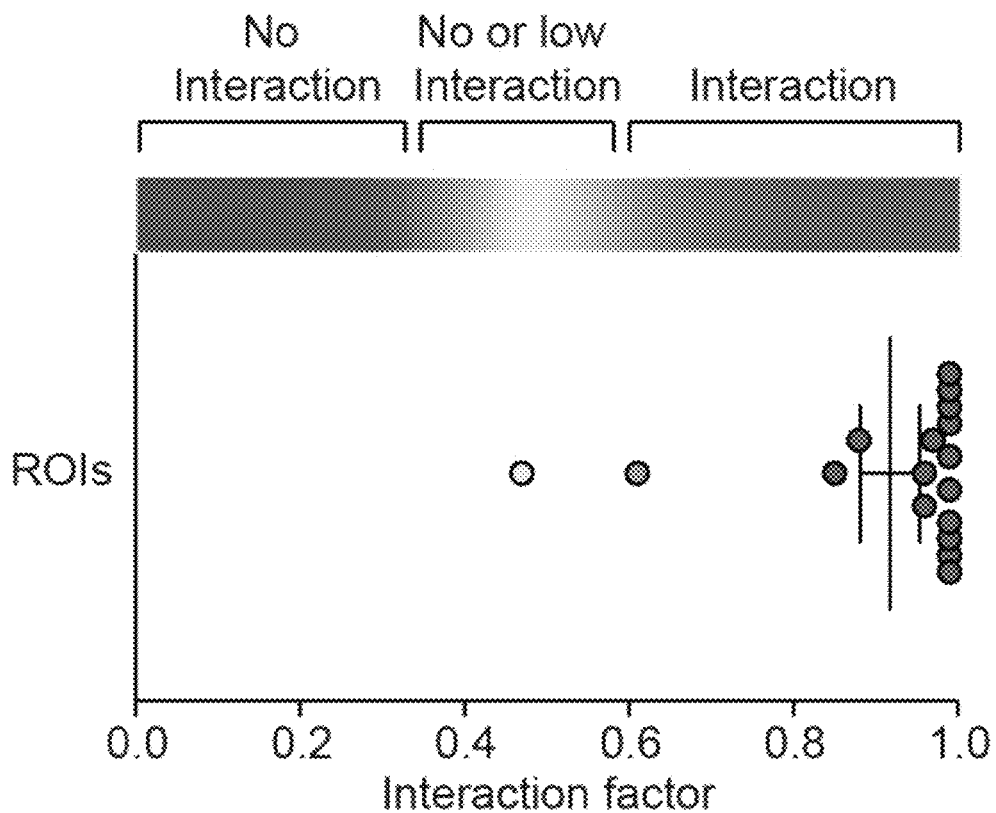

As presented in FIG. 21A, using the biotinylated LQI-tetramers, several potential peptide-binding ligands were identified in the neutrophil lysate. The neutrophil-specific surface protein CD177, having a molecular weight of 87 kDa was identified as the most significant peptide-binding ligand (FIG. 21B), resulting in a peptide/control ratio of 7.89 as indicated by peptide-pulldown enrichment of a 95 kD band in FIG. 21A. Flow cytometry showed that >99% of Ly6G+ circulating murine neutrophils are also CD177+ whereas Ly6G− cells are CD177− (FIG. 21C). Importantly, all circulating CD177+ cells (neutrophils) bind 16-LQI (FIG. 21D). The fact that the LQI-peptide binds only to HEK293T cells ectopically expressing the murine CD177 confirms that CD177 is both required and sufficient for LQI-peptide binding (FIG. 21E). Finally, using STORM it was found that the CD177 and 16-LQI signals overlap in >90% of the clusters, indicating that these molecules are in very close interaction (FIG. 21F-G).

Figure 22A:
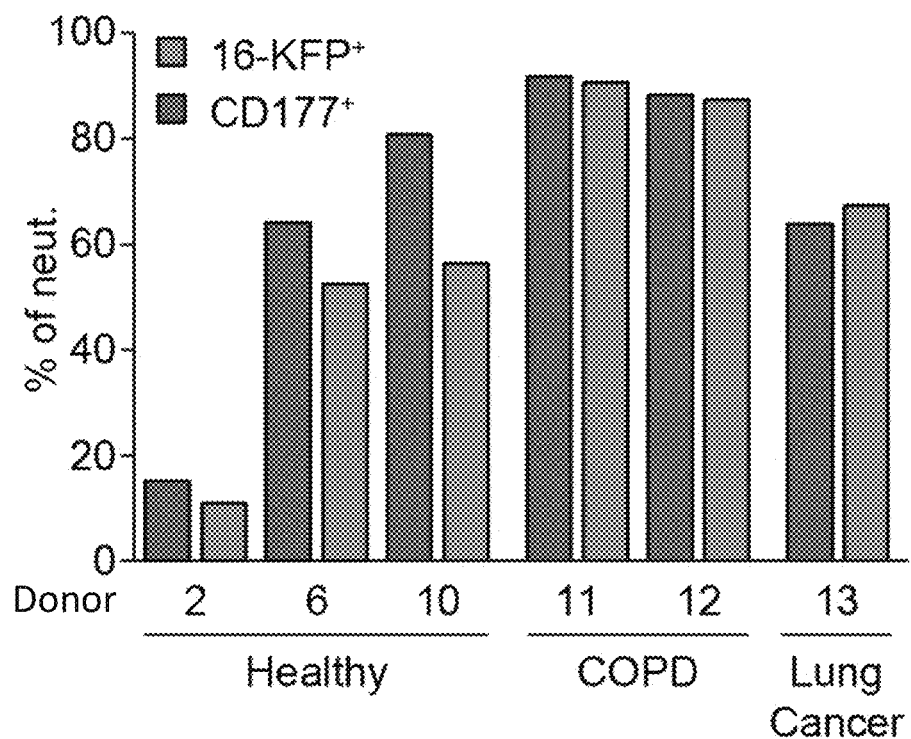
FIGS. 22A-C: (22A) Bar graph of 16-KFP binding and CD177 expression of neutrophils of healthy donors (2, 6, 10), COPD patients (11, 12) and lung cancer patients (13). (22B) Line graph of correlation between CD177 expression and 16-KFP binding in different donors. (22C) Bare graph of binding of 16-KFP to neutrophils with increasing amounts of CD177 blocking antibody.
Figure 22B:
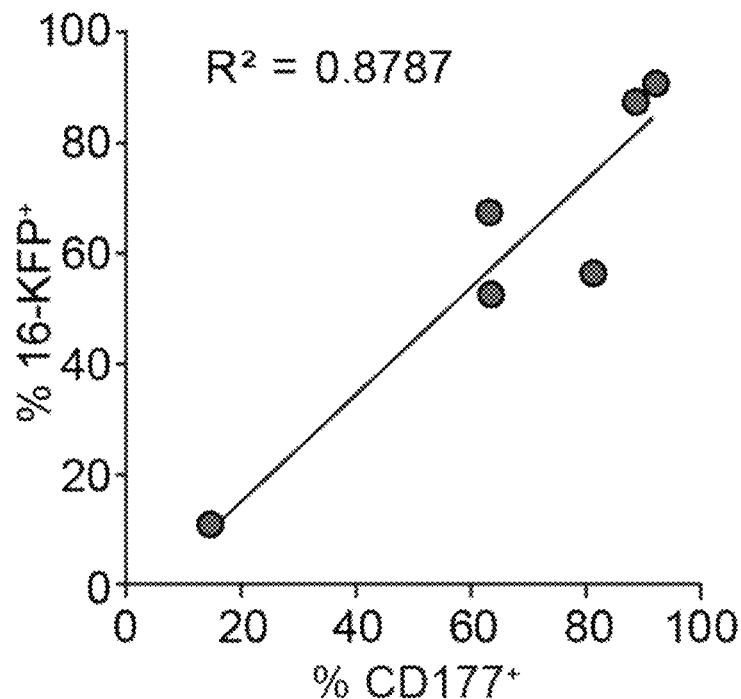
Figure 22C:
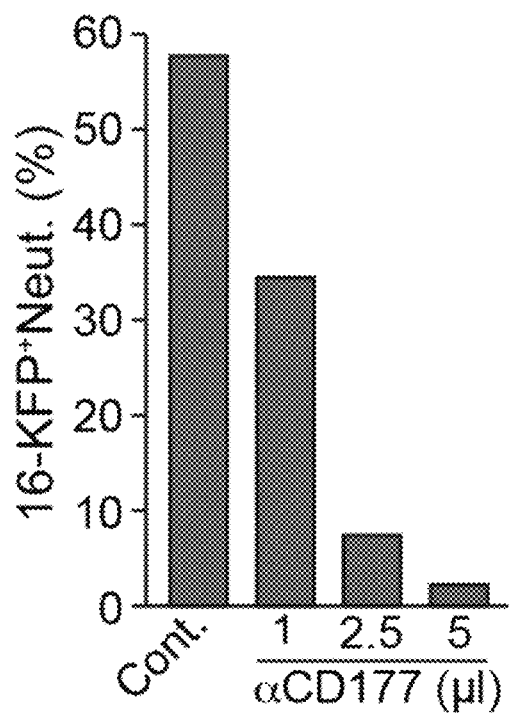

Similarly, the human CD177 was identified as a binding-partner of the peptides binding to human neutrophils (SEQ ID NOs: 1-8). Using the KFP-tetramer as bait in a pull-down experiment followed by mass spectrometry, CD177 was identified as the binding partner for 16-KFP. Indeed, a strong positive correlation between CD177 expression and KFP-tetramer binding to neutrophils of healthy donors, patients with COPD and lung cancer patients was observed (FIG. 22A-B). Interestingly, a single healthy donor was found whose neutrophils were bound only to a low percentage by the neutrophil-specific phages (see empty gray circles at the bottom of bars in FIG. 13I). This subject was found to in fact be a CD177 hypomorph (as are ~5% of the population) (FIG. 22A). Still, the extent of KFP-tetramer binding and CD177 levels fit well within the correlation plot and support the role of CD177 in mediating the binding of the KFP-tetramer to neutrophils (FIG. 22B). Further corroborating the role of CD177 in this process, it was demonstrated that increasing concentrations of a human CD177 antibody effectively compete with the binding or the 16-KFP (FIG. 22C). Intriguingly, the mouse and human CD177 proteins act as binding partners for neutrophil specific peptides although they differ in molecular weight (105 kDa and 54 kDa respectively) and the 16-LQI and the 16-KFP do not cross bind (see FIG. 2D, 16-Cont.).

As can be seen in FIG. 24, addition of free DPI completely blocked ROS production (compared to PMA alone). Treatment with empty nanoparticles had no significant effect on ROS production. In contract, treating neutrophils with DPI containing nanoparticles (NP+DPI) completely blocked ROS production. Similar observations were obtained using Sinomenine and *Ginko Biloba* as payload.

SEQUENCE LISTING

```
Sequence total quantity: 18
SEQ ID NO: 1                 moltype = AA  length = 15
FEATURE                      Location/Qualifiers
REGION                       1..15
                             note = Synthetic
source                       1..15
                             mol_type = protein
                             organism = synthetic construct
SEQUENCE: 1
KFPDLDSRRL PHMSL                                                          15

SEQ ID NO: 2                 moltype = AA  length = 12
FEATURE                      Location/Qualifiers
REGION                       1..12
                             note = Synthetic
source                       1..12
                             mol_type = protein
                             organism = synthetic construct
SEQUENCE: 2
LATTHMVFSP DH                                                             12

SEQ ID NO: 3                 moltype = AA  length = 13
FEATURE                      Location/Qualifiers
REGION                       1..13
                             note = Synthetic
source                       1..13
                             mol_type = protein
                             organism = synthetic construct
SEQUENCE: 3
PSSNLESTPL SLL                                                            13

SEQ ID NO: 4                 moltype = AA  length = 13
FEATURE                      Location/Qualifiers
REGION                       1..13
                             note = Synthetic
source                       1..13
                             mol_type = protein
                             organism = synthetic construct
SEQUENCE: 4
SSLMTTQLIA TSI                                                            13

SEQ ID NO: 5                 moltype = AA  length = 12
FEATURE                      Location/Qualifiers
REGION                       1..12
                             note = Synthetic
source                       1..12
                             mol_type = protein
                             organism = synthetic construct
SEQUENCE: 5
PELDSKPYFP PL                                                             12

SEQ ID NO: 6                 moltype = AA  length = 12
FEATURE                      Location/Qualifiers
REGION                       1..12
                             note = Synthetic
source                       1..12
                             mol_type = protein
                             organism = synthetic construct
SEQUENCE: 6
ELVTASMPRP NN                                                             12

SEQ ID NO: 7                 moltype = AA  length = 12
FEATURE                      Location/Qualifiers
REGION                       1..12
                             note = Synthetic
source                       1..12
                             mol_type = protein
                             organism = synthetic construct
SEQUENCE: 7
SLESSPMAQL PQ                                                             12

SEQ ID NO: 8                 moltype = AA  length = 12
FEATURE                      Location/Qualifiers
REGION                       1..12
                             note = Synthetic
source                       1..12
                             mol_type = protein
                             organism = synthetic construct
```

```
SEQUENCE: 8
SELRSTPLLV PS                                                                      12

SEQ ID NO: 9            moltype = AA  length = 10
FEATURE                 Location/Qualifiers
REGION                  1..10
                        note = Synthetic
source                  1..10
                        mol_type = protein
                        organism = synthetic construct
SEQUENCE: 9
LQIQSWSSSP                                                                         10

SEQ ID NO: 10           moltype = AA  length = 10
FEATURE                 Location/Qualifiers
REGION                  1..10
                        note = Synthetic
source                  1..10
                        mol_type = protein
                        organism = synthetic construct
SEQUENCE: 10
STMTILGTGS                                                                         10

SEQ ID NO: 11           moltype = AA  length = 12
FEATURE                 Location/Qualifiers
REGION                  1..12
                        note = Synthetic
source                  1..12
                        mol_type = protein
                        organism = synthetic construct
SEQUENCE: 11
TETSLRIVST NP                                                                      12

SEQ ID NO: 12           moltype = AA  length = 12
FEATURE                 Location/Qualifiers
REGION                  1..12
                        note = Synthetic
source                  1..12
                        mol_type = protein
                        organism = synthetic construct
SEQUENCE: 12
LSIVSGSALN HL                                                                      12

SEQ ID NO: 13           moltype = AA  length = 10
FEATURE                 Location/Qualifiers
REGION                  1..10
                        note = Synthetic
source                  1..10
                        mol_type = protein
                        organism = synthetic construct
SEQUENCE: 13
LTLVSERPMI                                                                         10

SEQ ID NO: 14           moltype = AA  length = 32
FEATURE                 Location/Qualifiers
REGION                  1..32
                        note = Synthetic
source                  1..32
                        mol_type = protein
                        organism = synthetic construct
SEQUENCE: 14
MLSFAAEGGQ RGLQIQSWSS SPAAGADPAK AA                                                32

SEQ ID NO: 15           moltype = AA  length = 19
FEATURE                 Location/Qualifiers
REGION                  1..19
                        note = Synthetic
source                  1..19
                        mol_type = protein
                        organism = synthetic construct
SEQUENCE: 15
GGGSRGLQIQ SWSSSPAAG                                                               19

SEQ ID NO: 16           moltype = AA  length = 4
FEATURE                 Location/Qualifiers
REGION                  1..4
                        note = Synthetic
source                  1..4
                        mol_type = protein
```

```
                    organism = synthetic construct
SEQUENCE: 16
KAKA                                                                            4

SEQ ID NO: 17      moltype = AA   length = 4
FEATURE            Location/Qualifiers
REGION             1..4
                   note = Synthetic
source             1..4
                   mol_type = protein
                   organism = synthetic construct
SEQUENCE: 17
GGGS                                                                            4

SEQ ID NO: 18      moltype = AA   length = 5
FEATURE            Location/Qualifiers
REGION             1..5
                   note = Synthetic
source             1..5
                   mol_type = protein
                   organism = synthetic construct
SEQUENCE: 18
GGGGS                                                                           5
```

The invention claimed is:

1. A peptide comprising an amino acid sequence selected from the group consisting of:

KFPDLDSRRLPHMSL; (SEQ ID NO: 1)

LATTHMVFSPDH; (SEQ ID NO: 2)

PSSNLESTPLSLL; (SEQ ID NO: 3)

SSLMTTQLIATSI; (SEQ ID NO: 4)

PELDSKPYFPPL; (SEQ ID NO: 5)

ELVTASMPRPNN; (SEQ ID NO: 6)

SLESSPMAQLPQ; (SEQ ID NO: 7)

SELRSTPLLVPS; (SEQ ID NO: 8)

STMTILGTGS; (SEQ ID NO: 10)

TETSLRIVSTNP; (SEQ ID NO: 11)

LSIVSGSALNHL; (SEQ ID NO: 12) and

LTLVSERPMI. (SEQ ID NO: 13)

2. The peptide of claim 1, consisting of 10-30 amino acids.

3. The peptide of claim 1, consisting of an amino acid sequence selected from the group consisting of: SEQ ID NO: 1-8 and 10-13.

4. The peptide of claim 1, comprising at least one cyclization.

5. The peptide of claim 1, wherein the peptide is conjugated to an 8-amino-3,6-dioxaoctanoic acid (Doa) residue.

6. The peptide of claim 1, wherein the peptide is conjugated to a 3-maleimidopropionic acid (Mpa) residue.

7. The peptide of claim 1, further comprising a C-terminal cysteine (C) residue.

8. A composition comprising a peptide of claim 1 attached to a therapeutic or diagnostic agent directly or through a carrier or linker.

9. A composition comprising a nanoparticle comprising a core particle and a peptide of claim 1 attached to the router surface of said core particle.

10. The composition of claim 9, further comprising a therapeutic or diagnostic agent.

11. The composition of claim 10, wherein said therapeutic agent is selected from the group consisting of a TGF-β inhibitor, an exocytosis inhibitor and a flavoenzyme inhibitor.

12. The composition of claim 11, wherein said TGF-β inhibitor is SB431542, said exocytosis inhibitor is Nexinhib-20 and said flavoenzyme inhibitor is diphenyleneiodonium chloride (DPI).

13. A method of targeting an agent to a human neutrophil, the method comprising administering to a human subject a composition comprising a peptide comprising any one of SEQ ID NO: 1-8 attached directly or through a carrier or linker to an agent, thereby targeting said agent to a human neutrophil.

14. A method of targeting an agent to a murine neutrophil, the method comprising administering to a murine subject a composition comprising a peptide comprising any one of SEQ ID NO: 10-13 attached directly or through a carrier or linker to an agent, thereby targeting said agent to a murine neutrophil.

15. A method of treating chronic obstructive pulmonary disease (COPD) in a subject in need thereof, the A method comprising administering to said subject the composition of claim 9, wherein said peptide comprises any one of SEQ ID NO: 1-8 and said nanoparticle comprises diphenyleneiodonium chloride (DPI) or Nexinhib-20, thereby treating COPD.

16. A peptide comprising the amino acid sequence LQIQSWSSP (SEQ ID NO: 9).

17. The peptide of claim 16,
a. consisting of 10-30 amino acids;
b. comprising at least one cyclization;
c. wherein the peptide is conjugated to an 8-amino-3,6-dioxaoctanoic acid (Doa) residue;
d. wherein the peptide is conjugated to a 3-maleimido-propionic acid (Mpa) residue; or
e. comprising a C-terminal cysteine (C) residue.

18. A composition comprising the peptide of claim 16, wherein said peptide is attached to a therapeutic or diagnostic agent directly or through a carrier or linker or wherein said composition comprises a nanoparticle comprising a core particle and said peptide is attached to the outer surface of said core particle.

19. The composition of claim 18, wherein said nanoparticle comprises a therapeutic or diagnostic agent.

20. A method of targeting an agent to a murine neutrophil, the method comprising administering to a murine subject a composition comprising the peptide of claim 16 attached directly or through a carrier or linker to an agent, thereby targeting said agent to a murine neutrophil.

* * * * *